United States Patent
Miao et al.

(10) Patent No.: US 9,884,127 B2
(45) Date of Patent: Feb. 6, 2018

(54) DRUG-CONJUGATES, CONJUGATION METHODS, AND USES THEREOF

(71) Applicant: CONCORTIS BIOSYSTEMS, CORP, San Diego, CA (US)

(72) Inventors: Zhenwei Miao, San Diego, CA (US); Yufeng Hong, San Diego, CA (US); Tong Zhu, San Diego, CA (US); Alexander Wilhelm Chucholowski, Poway, CA (US)

(73) Assignee: Concortis Biosystems, Corp., San Diego, CA (US)

( * ) Notice: Subject to any disclaimer, the term of this patent is extended or adjusted under 35 U.S.C. 154(b) by 21 days.

(21) Appl. No.: 14/401,114

(22) PCT Filed: May 14, 2013

(86) PCT No.: PCT/US2013/041026
§ 371 (c)(1),
(2) Date: Nov. 13, 2014

(87) PCT Pub. No.: WO2013/173391
PCT Pub. Date: Nov. 21, 2013

(65) Prior Publication Data
US 2015/0105539 A1 Apr. 16, 2015

Related U.S. Application Data

(60) Provisional application No. 61/647,300, filed on May 15, 2012, provisional application No. 61/648,406, filed on May 17, 2012, provisional application No. 61/648,532, filed on May 17, 2012, provisional application No. 61/652,512, filed on May 29, 2012.

(51) Int. Cl.
| | | |
|---|---|---|
| A61K 39/00 | (2006.01) |
| A61K 47/48 | (2006.01) |
| C07D 207/02 | (2006.01) |
| C07D 241/12 | (2006.01) |
| C07D 241/14 | (2006.01) |
| C07D 249/04 | (2006.01) |
| C07D 251/12 | (2006.01) |
| C07D 261/08 | (2006.01) |
| C07D 261/10 | (2006.01) |
| C07D 207/08 | (2006.01) |
| C07D 207/09 | (2006.01) |
| C07D 277/593 | (2006.01) |
| C07D 401/12 | (2006.01) |
| C07D 403/12 | (2006.01) |
| C07F 5/02 | (2006.01) |
| C07K 5/06 | (2006.01) |
| A61K 38/07 | (2006.01) |
| A61K 47/68 | (2017.01) |

(52) U.S. Cl.
CPC ........ *A61K 47/48584* (2013.01); *A61K 38/07* (2013.01); *A61K 47/6803* (2017.08); *A61K 47/6811* (2017.08); *A61K 47/6849* (2017.08); *A61K 47/6855* (2017.08); *A61K 47/6889* (2017.08); *C07D 207/08* (2013.01); *C07D 207/09* (2013.01); *C07D 277/593* (2013.01); *C07D 401/12* (2013.01); *C07D 403/12* (2013.01); *C07F 5/025* (2013.01); *C07K 5/06008* (2013.01)

(58) Field of Classification Search
None
See application file for complete search history.

(56) References Cited

U.S. PATENT DOCUMENTS

| | | |
|---|---|---|
| 5,780,588 A | 7/1998 | Pettit et al. |
| 6,124,431 A | 9/2000 | Sakakibara et al. |
| 6,569,834 B1 | 5/2003 | Pettit et al. |
| 7,531,162 B2 | 5/2009 | Collins et al. |
| 7,767,205 B2 | 8/2010 | Mao et al. |
| 7,829,531 B2 | 11/2010 | Senter et al. |
| 7,994,135 B2 | 8/2011 | Doronina et al. |
| 8,088,387 B2 | 1/2012 | Steeves et al. |
| 8,470,984 B2 | 6/2013 | Caruso et al. |
| 2005/0238649 A1 | 10/2005 | Doronina et al. |
| 2006/0128754 A1 | 6/2006 | Hoefle et al. |
| 2007/0092940 A1* | 4/2007 | Eigenbrot ........ A61K 47/48538 435/69.1 |
| 2007/0134243 A1 | 6/2007 | Gazzard et al. |
| 2011/0206658 A1 | 8/2011 | Crowley et al. |
| 2011/0217321 A1 | 9/2011 | Torgov et al. |
| 2011/0245295 A1 | 10/2011 | Chai et al. |
| 2011/0263650 A1 | 10/2011 | Ellman et al. |
| 2011/0268751 A1 | 11/2011 | Sievers et al. |
| 2011/0301334 A1 | 12/2011 | Bhakta et al. |
| 2012/0148610 A1 | 6/2012 | Doronina et al. |

(Continued)

FOREIGN PATENT DOCUMENTS

| | | |
|---|---|---|
| CA | 2813056 A1 | 4/2012 |
| EP | 0624377 A2 | 11/1994 |

(Continued)

OTHER PUBLICATIONS

Dosio et al (II Farmaco, 1996, vol. 51, pp. 477-482).*

(Continued)

*Primary Examiner* — Karen Canella
(74) *Attorney, Agent, or Firm* — Womble Bond Dickinson (US) LLP; Danielle L. Herritt

(57) ABSTRACT

In one aspect, an active agent-conjugate, methods of preparing the active agent-conjugate, and uses thereof is provided.

10 Claims, 12 Drawing Sheets

(56) References Cited

U.S. PATENT DOCUMENTS

| | | | |
|---|---|---|---|
| 2013/0029900 A1 | 1/2013 | Widdison | |
| 2013/0101546 A1 | 4/2013 | Yurkovetskiy et al. | |
| 2013/0224228 A1* | 8/2013 | Jackson ........... | A61K 39/39558 424/179.1 |
| 2014/0030282 A1 | 1/2014 | Polakis et al. | |
| 2015/0105539 A1 | 4/2015 | Miao et al. | |
| 2015/0105540 A1 | 4/2015 | Miao et al. | |
| 2015/0141646 A1 | 5/2015 | Miao et al. | |
| 2016/0067350 A1 | 3/2016 | Miao et al. | |

FOREIGN PATENT DOCUMENTS

| | | |
|---|---|---|
| WO | 2005/081711 A2 | 9/2005 |
| WO | 2007/109567 A1 | 9/2007 |
| WO | 2008/112873 A2 | 9/2008 |
| WO | 2010/009124 A2 | 1/2010 |
| WO | 2012/010287 A1 | 1/2012 |
| WO | 2012/166559 A1 | 12/2012 |
| WO | 2012/166560 A1 | 12/2012 |
| WO | 2013/085925 A1 | 6/2013 |
| WO | 2013/173391 A1 | 11/2013 |
| WO | 2013/173392 A1 | 11/2013 |
| WO | 2013/173393 A1 | 11/2013 |
| WO | 2013/185117 A1 | 12/2013 |
| WO | 2013/192360 A1 | 12/2013 |
| WO | 2015/057876 A1 | 4/2015 |
| WO | 2016/123412 A1 | 8/2016 |
| WO | 2016/127081 A1 | 8/2016 |

OTHER PUBLICATIONS

The abstract of Geroni et al (Proc. Amer. Assoc. Cancer Res., 2006, vol. 47, abstract No. 3845).*

Cella, R., et al., "Steroselective Synthesis of the Dolastatin Units by Organotriflouroborates Additions to Alpha-Amino Aldehydes", Tetrahedron Letters, 49 (2008) 16-19.
Ducry, L et al., "Antibody-Drug Conjugates: Linking Cytotoxic Payloads to Monoclonal Antibodies" Bioconjugate Chemistry, 2010, vol. 21, No. 1, pp. 5-13.
Kingston, David "Tubulin Interactive Natural Products as Anticancer Agents" J Nat Prod. Mar. 2009; 72(3): 507-515.
Petit, et al., "Specific Activities of Dolastatin 10 and Peptide Derivatives Against Crypococcus neoformans" Antimicrobial Agents and Chemotherapy, Nov. 1998, p. 2961-2965.
PubChemCompound datasheet (online compound summary) CID 56841603; Create Date: Mar. 21, 2012; http://pubchem.ncbi.nlm.nih.gov/summary/summary.cgi?cid =56841603.
Younes, A. et al., "Brentuximab Vedotin (SGN-35) for Relapsed CD30-Positive Lymphomas"The New England Journal of Medicine, 363; 19, 2010, 1812-1821.
Copending U.S. Appl. No. 14/401,115, filed Oct. 13, 2014.
Copending U.S. Appl. No. 14/401,318, filed Nov. 14, 2014.
Copending U.S. Appl. No. 14/515,352, filed Nov. 15, 2014.
Copending U.S. Appl. No. 15/009,775, filed Jan. 28, 2016.
Copending U.S. Appl. No. 15/017,174, filed Feb. 5, 2016.
U.S. Appl. No. 15/009,775, filed Jan. 29, 2016.
U.S. Appl. No. 14/401,115, filed Nov. 13, 2014.
U.S. Appl. No. 14/401,318, filed Nov. 14, 2014.
U.S. Appl. No. 14/515,352, filed Oct. 15, 2014.
U.S. Appl. No. 15/009,775, filed Jan. 28, 2016.
U.S. Appl. No. 15/017,174, filed Feb. 5, 2016.
Pettit, G. et al., "Antineoplastic Agents. 592. Highly Effective Cancer Cell Growth Inhibitory Structural Modifications of Dolastatin 10" Jouranl of Natual Products, 2011, 74, 962-968.
Tannock et al., The Basic Science of Oncology, Ch. 19—Experimental Chemotherapy, p. 338 and p. 352-359, New York, 1992.

* cited by examiner

DRUG-CONJUGATES, CONJUGATION METHODS, AND USES THEREOF

BACKGROUND

Recently, it has been found that an antibody (or antibody fragment such as a single-chain variable fragment) can be linked to a payload drug to form an immunoconjugate that has been termed antibody-drug conjugate, or ADC. The antibody causes the ADC to bind to the target cells. Often the ADC is then internalized by the cell and the drug is released to treat the cell. Because of the targeting, the side effects may be lower than the side effects of systemically administering the drug.

SUMMARY

Some embodiments provide active agent-conjugates, methods of preparing active agent-conjugates, and uses thereof.

Some embodiments provide an active agent-conjugate having the structure of Formula I:

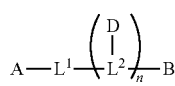

(I)

or a pharmaceutically acceptable salt thereof,
wherein:
A may be a targeting moiety;
B may be an auxiliary moiety that optionally is a second targeting moiety, or B may be null;
$L^1$ includes a 2- to 5-carbon bridge and at least one sulfur atom;
each D may be independently selected, where each D includes an active agent;
each $L^2$ may be independently a linker, wherein at least one $L^2$ links to $L^1$; and
n may be 1, 2, 3, 4, 5, 6, 7, 8, 9, or 10.

Some embodiments provide an active agent-conjugate having the structure of Formula Ia:

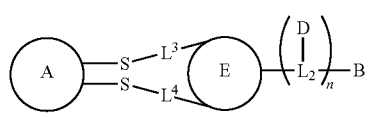

(Ia)

or a pharmaceutically acceptable salt thereof,
wherein:
the A-component may be a targeting moiety;
the E-component may be an optionally substituted heteroaryl or an optionally substituted heterocyclyl;
B may be an auxiliary moiety that optionally is a second targeting moiety, or B may be null;
each D may be independently selected, where each D includes an active agent;
each $L^2$ may be independently a linker, wherein at least one $L^2$ links to $L^1$; and
n may be 1, 2, 3, 4, 5, 6, 7, 8, 9, or 10;
$L^3$ may be an optionally substituted $C_1$-$C_6$ alkyl, or $L^3$ may be null, when $L^3$ is null the sulfur is directly connected to the E-component; and
$L^4$ may be an optionally substituted $C_1$-$C_6$ alkyl, or $L^4$ may be null, when $L^4$ is null the sulfur is directly connected to the E-component.

In some embodiments, the E-component includes a fragment selected from the group consisting of:

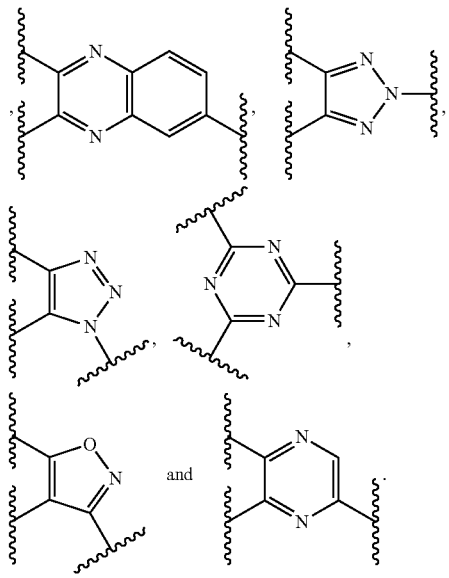

In some embodiments, $L^3$ may be —(CH$_2$)—; and $L^4$ may be —(CH$_2$)—. In some embodiments, $L^3$ may be null; and $L^4$ may be null.

In some embodiments,

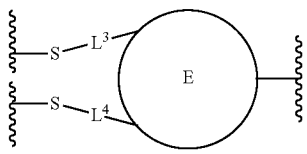

may be:

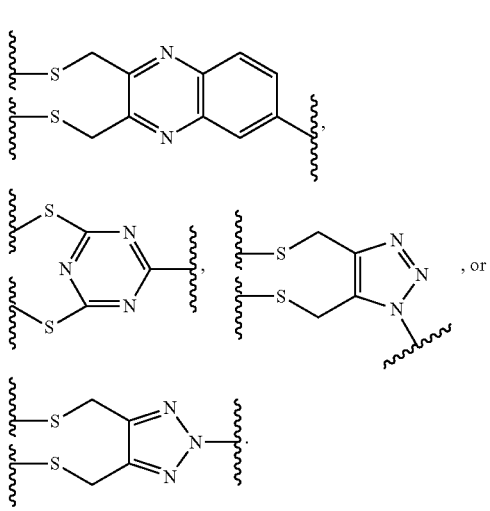

In some embodiments, $L^2$ includes —$(CH_2)_n$— where n may be 1, 2, 3, 4, 5, 6, 7, 8, 9, or 10. In some embodiments, $L^2$ includes —$(CH_2CH_2O)_n$— where n may be 1, 2, 3, 4, 5, 6, 7, 8, 9, or 10. In some embodiments, $L^2$ includes Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, $L^2$ includes peptide, oligosaccharide, —$(CH_2)_n$—, —$(CH_2CH_2O)_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, or combinations thereof. In some embodiments, $L^2$ includes a noncleavable unit. In some embodiments, the noncleavable unit includes —$(CH_2)_n$— where n may be 1, 2, 3, 4, 5, 6, 7, 8, 9, or 10. In some embodiments, the noncleavable unit includes —$(CH_2CH_2O)_n$— where n may be 1, 2, 3, 4, 5, 6, 7, 8, 9, or 10. In some embodiments, $L^2$ includes a cleavable unit. In some embodiments, the cleavable unit comprises a peptide.

In some embodiments, the A component comprises a monoclonal antibody (mAB). In some embodiments, the A component comprises an antibody fragment, surrogate, or variant. In some embodiments, the A component comprises a protein ligand. In some embodiments, the A component comprises a protein scaffold. In some embodiments, the A component comprises a peptide. In some embodiments, the A component comprises a small molecule ligand. In some embodiments, the A component comprises at least one modified L-Alanine residue. In some embodiments, the A component comprises at least two modified L-Alanine residues. In some embodiments, at least one $L^2$ includes —$(CH_2)_n$— where n may be 1, 2, 3, 4, 5, 6, 7, 8, 9, or 10. In some embodiments, at least one $L^2$ includes —$(CH_2CH_2O)_n$— where n may be 1, 2, 3, 4, 5, 6, 7, 8, 9, or 10. In some embodiments, at least one $L^2$ includes Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, at least one $L^2$ includes a peptide, an oligosaccharide, —$(CH_2)_n$—, —$(CH_2CH_2O)_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB or combinations thereof.

DETAILED DESCRIPTION

Figure 1:
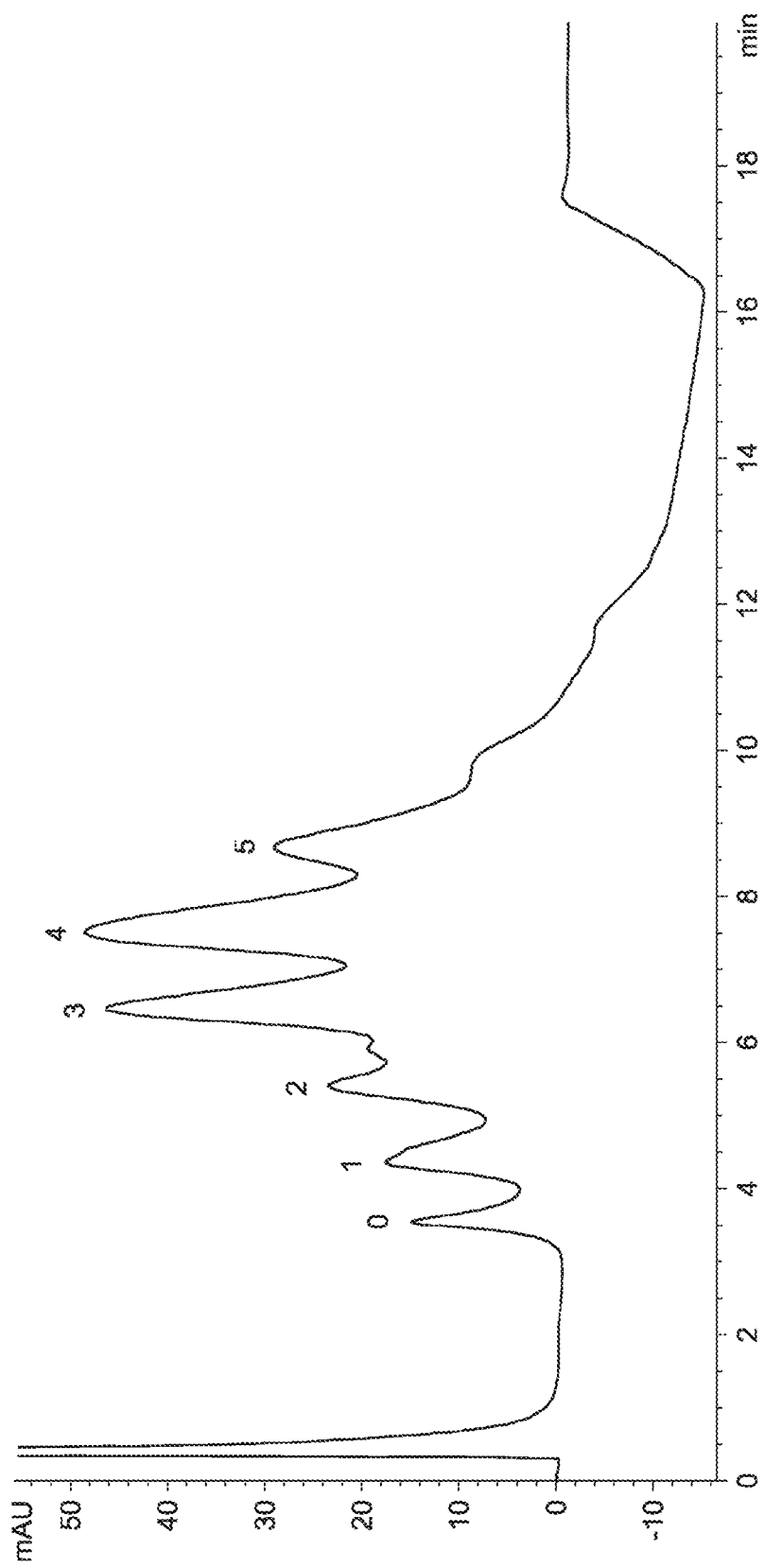
FIG. 1 shows the HIC-HPLC chromatogram product of reacting drug and antibody at a drug/antibody ratio of 5.5:1.

Some embodiments provide an active agent-conjugate. In some embodiments, the active agent-conjugate is a drug-conjugate. In some embodiments, the drug-conjugate includes a targeting molecule. In some embodiments, the targeting molecule includes a monoclonal antibody (mAB). In some embodiments, the drug-conjugate includes a spacer or a multifunctional linker. In some embodiments, the spacer connects to the mAB by a sulfide bond. In some embodiments, the multifunctional linker connects to the mAB by a sulfide bond. In some embodiments, the spacer or multifunctional linker may be optionally connected to an auxiliary moiety. In some embodiments, the auxiliary moiety may be a second targeting molecule such as mAB and peptide. In some embodiments, the auxiliary moiety may be a hydrophilic polymer such as polyethylene glycol (PEG), and the like. In some embodiments, the spacer or multifunctional linker may include a 2- to 5-atom bridge. In some embodiments, the spacer or multifunctional linker may include a 4C (four carbon) bridge.

Conjugation methods to derivatize a polypeptide with a payload can be accomplished using a maleimido or vinyl moiety which can react with individual sulfhydryl group on an antibody via Michael addition reaction. The free sulfhydryl group can be formed by reducing a disulfide bond in an antibody. However, the structural integrity of an antibody can be compromised after opening disulfide bonds and attaching payloads to the exposed free thiols. The compositions and methods provided herein provide conjugation through cysteine without decreased structural stability.

Definitions

As used herein, common organic abbreviations are defined as follows:

Ac Acetyl
aq. Aqueous
BOC or Boc tert-Butoxycarbonyl
BrOP bromo tris(dimethylamino) phosphonium hexafluorophosphate
Bu n-Butyl
° C. Temperature in degrees Centigrade
DCM methylene chloride
DEPC Diethylcyanophosphonate
DIC diisopropylcarbodiimide
DIEA Diisopropylethylamine
DMA N,N'-Dimethylacetamide
DMF N,N'-Dimethylformamide
DTT Dithiothreitol
EDC 1-Ethyl-3-(3-dimethylaminopropyl)carbodiimide
Et Ethyl
EtOAc Ethyl acetate
Eq Equivalents
Fmoc 9-Fluorenylmethoxycarbonyl
g Gram(s)
h Hour (hours)
HATU 2-(1H-7-azabenzotriazol-1-yl)-1,1,3,3-tetramethyl uronium hexafluorophosphate
HOAt 1-Hydroxy-7-azabenzotriazole
HOBT N-Hydroxybenzotriazole
HPLC High-performance liquid chromatography LC/MS Liquid chromatography-mass spectrometry
Me Methyl
MeOH Methanol
MeCN Acetonitrile
mL Milliliter(s)
MS mass spectrometry
PAB p-aminobenzyl
RP-HPLC reverse phase HPLC
t-Bu tert-Butyl
TCEP Tris(2-carboxyethyl)phosphine
TEA Triethylamine
Tert, t tertiary
TFA Trifluoracetic acid
THF Tetrahydrofuran
THP Tetrahydropyranyl
TLC Thin-layer chromatography
μL Microliter(s)

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O (oxygen), N (nitrogen) or S (sulfur), and in preferred five membered monocyclic heterocyclyls, the heteroatom(s) are selected from one or two heteroatoms selected from O (oxygen), N (nitrogen), or S (sulfur). Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)C(=O)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "urea" group refers to a "—N(R$_A$)C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)C(=S)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

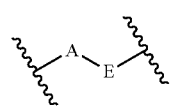

includes the substituent being oriented such that the A is attached at the leftmost attachment point of the molecule as well as the case in which A is attached at the rightmost attachment point of the molecule.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

Conjugation Methods, Spacers and Linkers Involved

Some embodiments provide a method of conjugating of a targeting molecule through a spacer or a multifunctional linker. In some embodiments, the spacer or multifunctional linker may include a 2- to 5-atom bridge. In some embodiments, the method includes a single-step or sequential conjugation approach. In some embodiments, the drug-conjugates include a spacer or a multifunctional linker. In some embodiments, the spacer or multifunctional linker may include a noncleavable or cleavable unit such as peptides.

Utilities and Applications

Some embodiments provide a method of treating a patient in need thereof comprising administering an active agent-conjugate as disclosed and described herein to said patient. In some embodiments, the patient may have cancer, immune diseases or diabetes.

Some embodiments provide a method of diagnosis or imaging comprising administering an active agent-conjugate as disclosed and described herein to an individual.

Certain Structures

Some embodiments provide an active agent-conjugate having the structure of Formula I

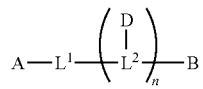

(I)

or a pharmaceutically acceptable salt thereof,
wherein:
A may be a targeting molecule;
B is an auxiliary moiety that optionally is a second targeting molecule, or B is null;
$L^1$ includes a 2- to 5-carbon bridge and at least one sulfur atom;
each D is independently selected, where each D includes an active agent;
each $L^2$ is independently a linker, wherein at least one $L^2$ links to $L^1$;
and
n is 1, 2, 3, 4, 5, 6, 7, 8, 9, or 10.

In some embodiments, A may be a monoclonal antibody (mAB).

In some embodiments, A may be an antibody fragment, surrogate, or variant.

In some embodiments, A may be a protein ligand.
In some embodiments, A may be a protein scaffold.
In some embodiments, A may be a peptide.
In some embodiments, A may be a small molecule ligand.
In some embodiments, B may be a hydrophilic polymer. In some embodiments, the hydrophilic polymer may polyethylene glycol (PEG), and the like. In some embodiments, B may be a biodegradable polymer. In some embodiments, the biodegradable polymer may be unstructured proteins polyamino acids, polypeptides polysaccharides and combinations thereof.

In some embodiments, B may be a monoclonal antibody (mAB).

In some embodiments, B may be an antibody fragment, surrogate, or variant.

In some embodiments, B may be a protein ligand.
In some embodiments, B may be a protein scaffold.
In some embodiments, B may be a peptide.
In some embodiments, B may be RNA or DNA.
In some embodiments, B may be a RNA or DNA fragment.
In some embodiments, B may be a small molecule ligand.
In some embodiments, D may be a biologically active compound.
In some embodiments, D may be a drug.
In some embodiments, D may be a chemotherapy drug.
In some embodiments, D may be a natural product.
In some embodiments, D may be an immune modulator.
In some embodiments, D may be a tubulin-binder.
In some embodiments, D may be a DNA-alkylating agent.
In some embodiments, D may be an HSP90 inhibitor.
In some embodiments, D may be a DNA topoisomerase inhibitor.
In some embodiments, D may be an anti-epigenetic agent.
In some embodiments, D may be an HDAC inhibitor.
In some embodiments, D may be an anti-metabolism agent.
In some embodiments, D may be a proteasome inhibitor.
In some embodiments, D may be a peptide.
In some embodiments, D may be a peptidomimetic.
In some embodiments, D may be an siRNA.
In some embodiments, D may be an antisense DNA.
In some embodiments, D may be epothilone A, epothilone B, or paclitaxel.

In some embodiments, $L^2$ may include a spacer or a multifunctional linker. In some embodiments, $L^2$ may include a spacer and a multifunctional linker. In some embodiments, $L^2$ may include a multifunctional linker. In some embodiments, each $L^2$ may be a linker, wherein the linker may be cleavable or non-cleavable under biological conditions. In some embodiments, the linker may be cleavable by an enzyme. In some embodiments, $L^2$ may include Linker.

In some embodiments, $L^1$ includes a 2- to 5-carbon bridge and at least one sulfur atom. In some embodiments, $L^1$ includes a 2- to 5-carbon bridge and at least two sulfur atoms. In some embodiments, $L^1$ includes a 2- to 5-carbon bridge and a spacer. In some embodiments, $L^1$ includes a 2- to 5-carbon bridge, at least two sulfur atoms and a spacer. In some embodiments, $L^1$ may include one or more sulfurs. In some embodiments, the $L^1$ may include two or more sulfurs. In some embodiments, the $L^1$ may include exactly two sulfurs. In some embodiments, may include a 4-carbon bridge and/or a spacer. In some embodiments, $L^1$ include a 4-carbon bridge or a spacer. In some embodiments, $L^1$ may include a 4-carbon bridge and a spacer. In some embodiments, $L^1$ includes a 4-carbon bridge and at least two sulfur atoms. In some embodiments, the spacer connects to the mAB by a sulfide bond. In some embodiments, the spacer connects to the mAB through a thioether.

In some embodiments, A comprises at least one modified L-Alanine residue. In some embodiments, A comprises at least two modified L-Alanine residues. In some embodiments, $L^1$ comprises at least one sulfur. In some embodiments, $L^1$ comprises at least two sulfurs. In some embodiments, A comprises at least one modified L-Alanine residue that is connected to at least one sulfur of $L^1$. In some embodiments, at least one modified L-Alanine residue is from an L-Cysteine residue of a peptide before conjugation.

In some embodiments, at least one sulfur of $L^1$ is from an

L-Cysteine of a peptide before conjugation. In some embodiments, A and $L^1$ together comprise at least one thioether.

In some embodiments, Linker may be a peptide.

In some embodiments, Linker may include an oligosaccharide. For example, Linker may include chitosan. In some embodiments, $L^2$ may include Linker and —$(CH_2)_n$— where n is 1, 2, 3, 4, 5, 6, 7, 8, 9, or 10. In some embodiments, $L^2$ may include Linker and —$(CH_2CH_2O)_n$— where n is 1, 2, 3, 4, 5, 6, 7, 8, 9, or 10.

In some embodiments, Linker may include —$(CH_2)_n$— where n is 1, 2, 3, 4, 5, 6, 7, 8, 9, or 10.

In some embodiments, Linker may include —$(CH_2CH_2O)_n$— where n is 1, 2, 3, 4, 5, 6, 7, 8, 9, or 10.

In some embodiments, Linker may include Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, or the like.

In some embodiments, Linker may include any combination of peptide, oligosaccharide, —$(CH_2)_n$—, —$(CH_2CH_2O)_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, and the like.

In some embodiments, the spacer may include a peptide.

In some embodiments, the spacer may include an oligosaccharide. For example, the spacer may include chitosan.

In some embodiments, the spacer may include —$(CH_2)_n$— where n is 1, 2, 3, 4, 5, 6, 7, 8, 9, or 10. In some embodiments, $L^1$ may include a component including a 4-carbon bridge and —$(CH_2)_n$— where n is 1, 2, 3, 4, 5, 6, 7, 8, 9, or 10.

In some embodiments, the spacer may include —$(CH_2CH_2O)_n$— where n is 1, 2, 3, 4, 5, 6, 7, 8, 9, or 10. In some embodiments, $L^1$ may include a component including a 4-carbon bridge and —$(CH_2CH_2O)_n$— where n is 1, 2, 3, 4, 5, 6, 7, 8, 9, or 10.

In some embodiments, the spacer may include Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, or the like.

In some embodiments, the spacer may be any combination of peptide, oligosaccharide, —$(CH_2)_n$—, —$(CH_2CH_2O)_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, and the like.

In some embodiments, $L^1$ may include a 4-carbon bridge. In some embodiments, $L^1$ may include a 4-carbon bridge through a fused aromatic ring. In some embodiments, $L^1$ may include a spacer and component including a 4-carbon bridge through a fused aromatic ring. In some embodiments, $L^1$ may include, but is not limited

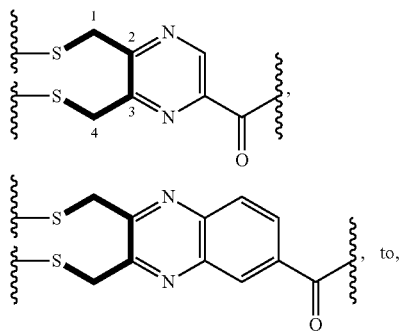
, to,

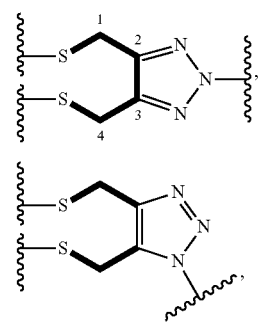

and the like.

In some embodiments, the agent-conjugate having the structure of Formula I has the structure of Formula Ia:

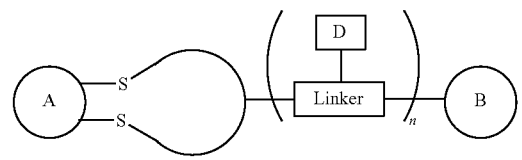

(Ia)

or a pharmaceutically acceptable salt thereof, wherein the S-linked portion of A comprises a modified L-Alanine residue, wherein

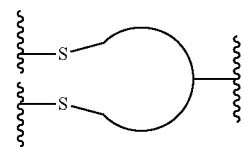

may connect to a sulfur of a reduced disulfide bond through a bridge containing 2 to 5 atoms. For example, the structure indicated by

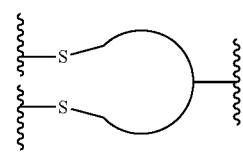

may include a fragment selected from the group consisting of:

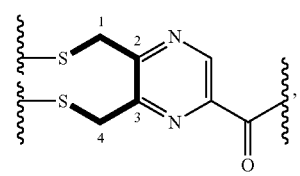

-continued

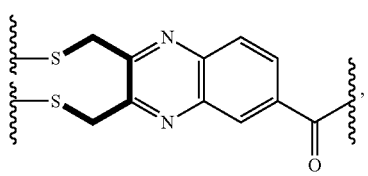

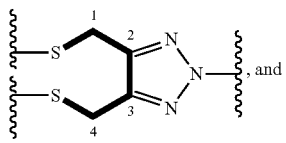, and

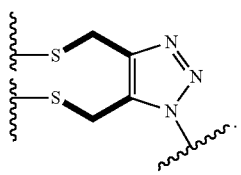.

In some embodiments, the S-linked (sulfur-linked) portion of A comprises a modified L-Alanine residue. In some embodiments, the S-linked (sulfur-linked) portion of A comprises a modified L-Alanine residue that is connected to the sulfur of $L^1$. In some embodiments, the S-linked (sulfur-linked) portion of A comprises a modified L-Alanine residue wherein the modified L-Alanine component of A is from an L-Cysteine residue of a peptide before conjugation. In some embodiments, the sulfur of $L^1$ is from an L-Cysteine of a peptide before conjugation. In some embodiments, A and $L^1$ comprise a thioether. In some embodiments, the compound having the structure of Formula Ia may be formed from a peptide that includes at least one L-Cysteine where the L-Cysteine provides a modified L-Alanine of A and a sulfur of

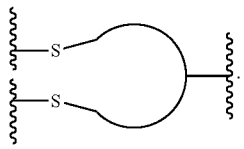

In some embodiments, the compound having the structure of Formula Ia may be formed from a peptide that includes at least two L-Cysteine where the two L-Cysteine provide two modified L-Alanines of A and two sulfur of

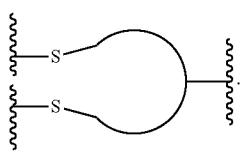

In some embodiments, the agent-conjugate having the structure of Formula I has the structure of Formula Ib:

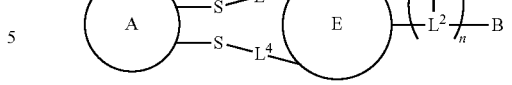

or a pharmaceutically acceptable salt thereof, wherein the A-component may be a targeting moiety, the E-component may be a heteroaryl or heterocyclyl, $L^3$ may be an optionally substituted $C_1$-$C_6$ alkyl, or $L^3$ may be null, when $L^3$ is null the sulfur is directly connected to the E-component; and $L^4$ may be an optionally substituted $C_1$-$C_6$ alkyl, or $L^4$ may be null, when $L^4$ is null the sulfur is directly connected to the E-component. In some embodiments, $L^3$ may be —(CH$_2$)—; and $L^4$ may be —(CH$_2$)—. In some embodiments, $L^3$ may be null; and $L^4$ may be null.

In some embodiments of the structure of Formula Ib, the structural component

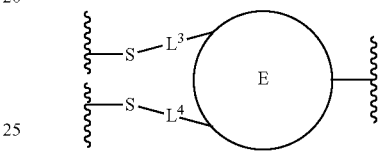

may be:

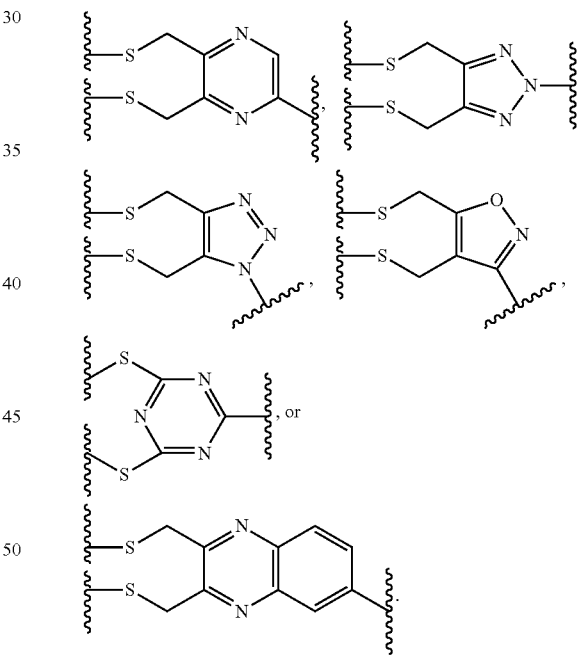

In some embodiments, the E-component includes a fragment selected from the group consisting of:

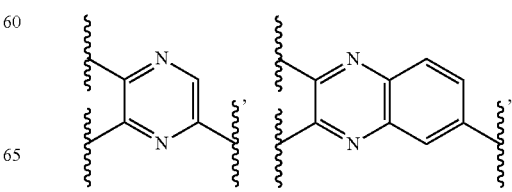

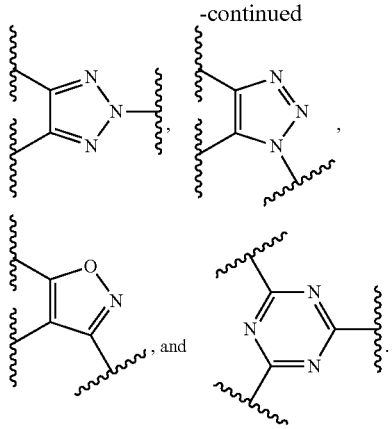

In some embodiments, the active agent may be selected from the group consisting of tubulin binders, DNA alkylators, DNA intercalator, enzyme inhibitors, immune modulators, peptides, and nucleotides.

In some embodiments, at least one $L^2$ includes —$(CH_2)_n$— where n is 1, 2, 3, 4, 5, 6, 7, 8, 9, or 10. In some embodiments, at least one $L^2$ includes —$(CH_2CH_2O)_n$— where n is 1, 2, 3, 4, 5, 6, 7, 8, 9, or 10. In some embodiments, at least one $L^2$ includes Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, at least one $L^2$ includes a peptide, an oligosaccharide, —$(CH_2)_n$—, —$(CH_2CH_2O)_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, at least one $L^2$ may comprise, consist of, or consist essentially of:

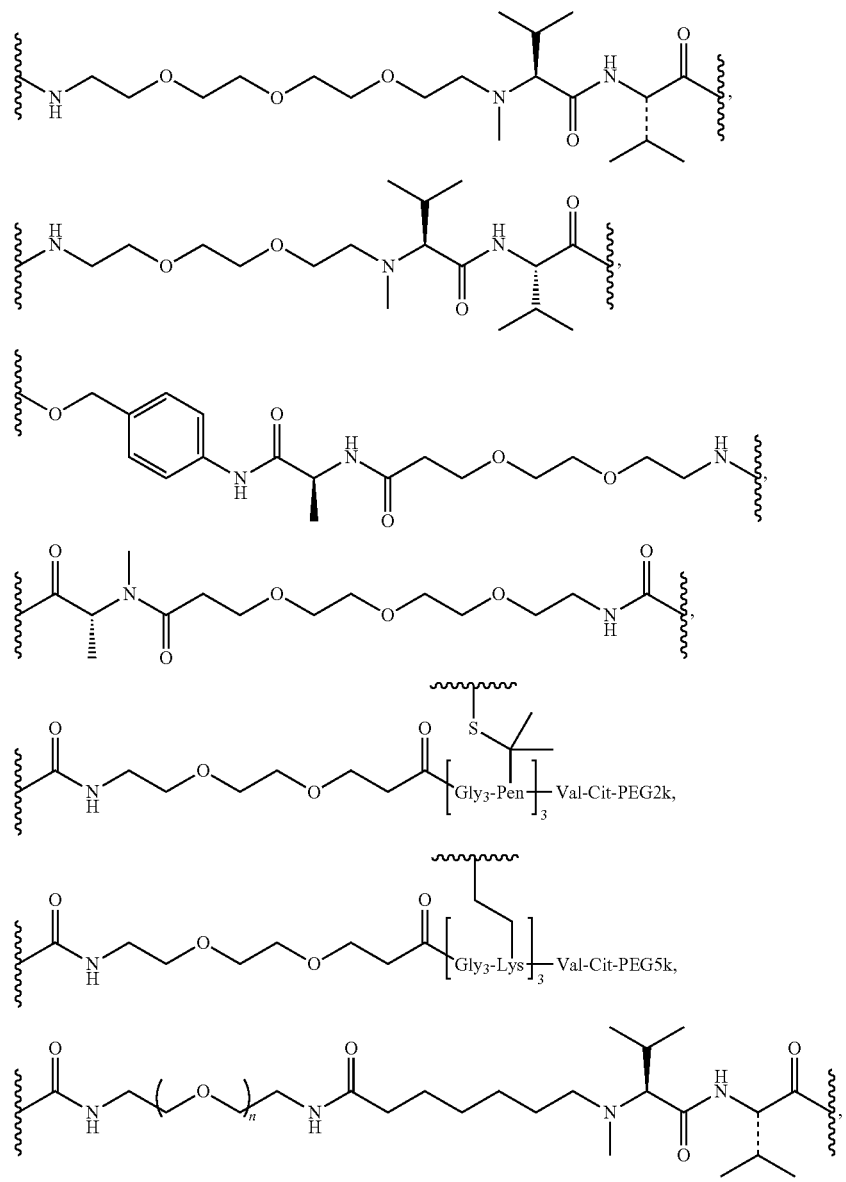

-continued
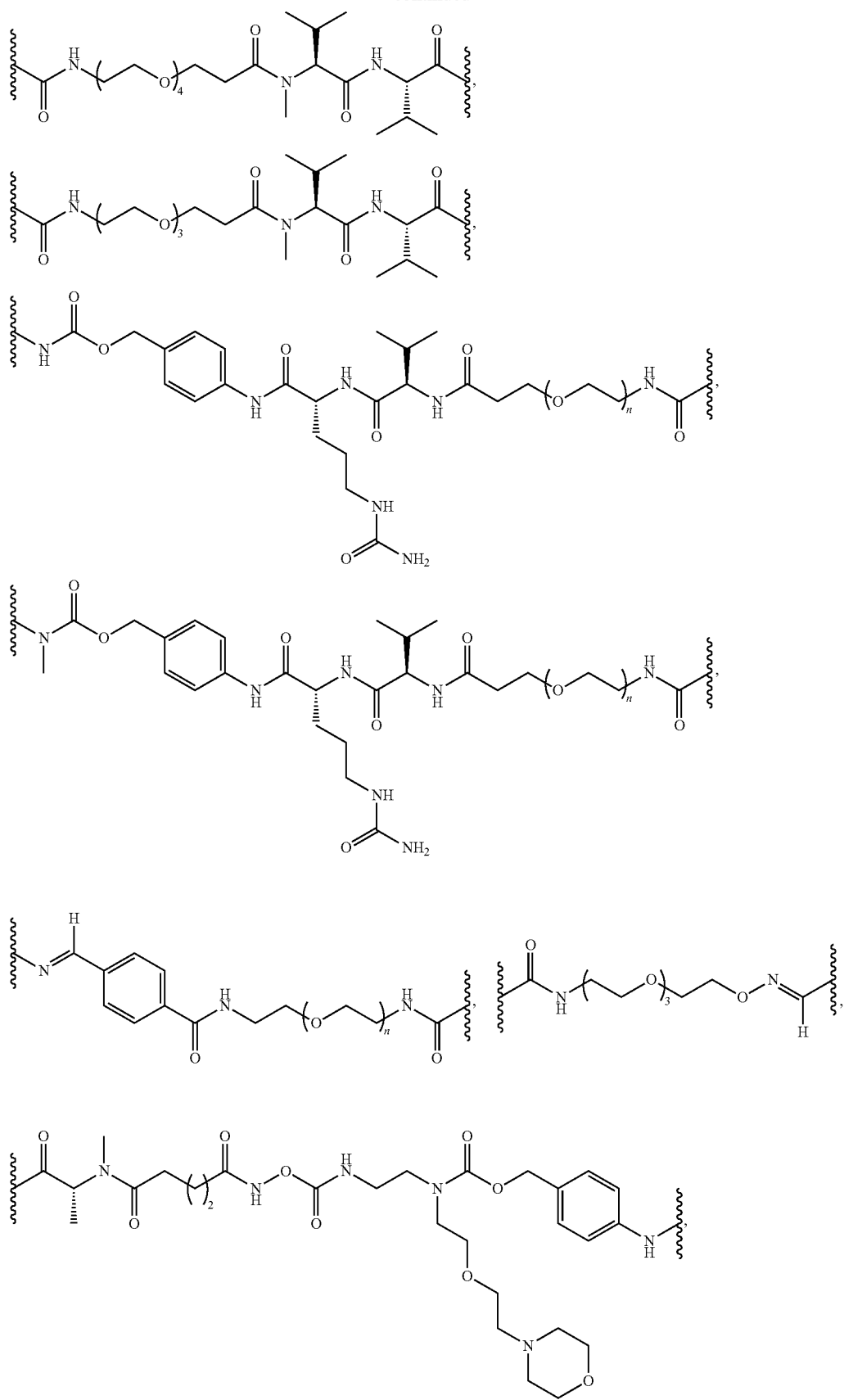

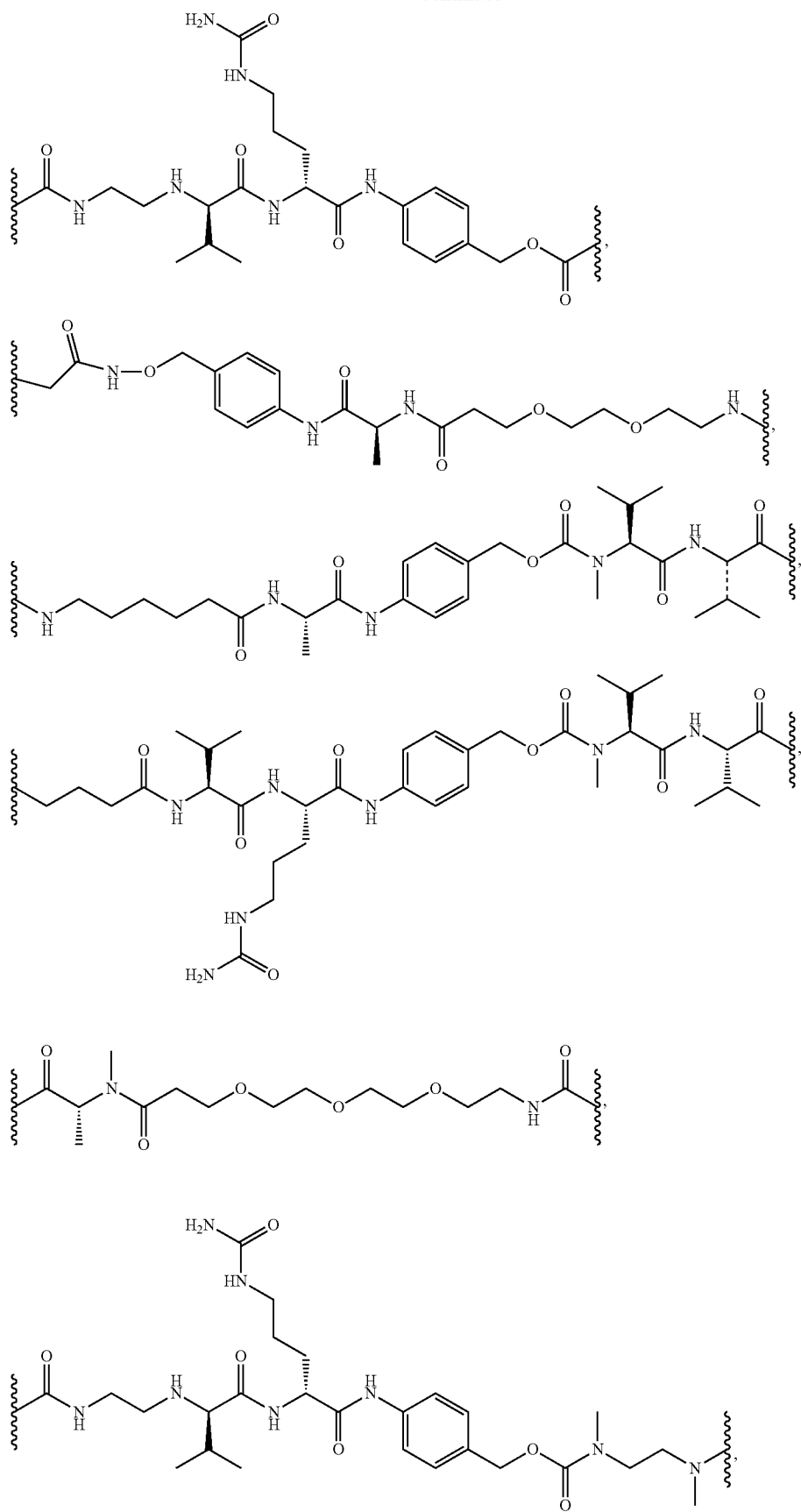

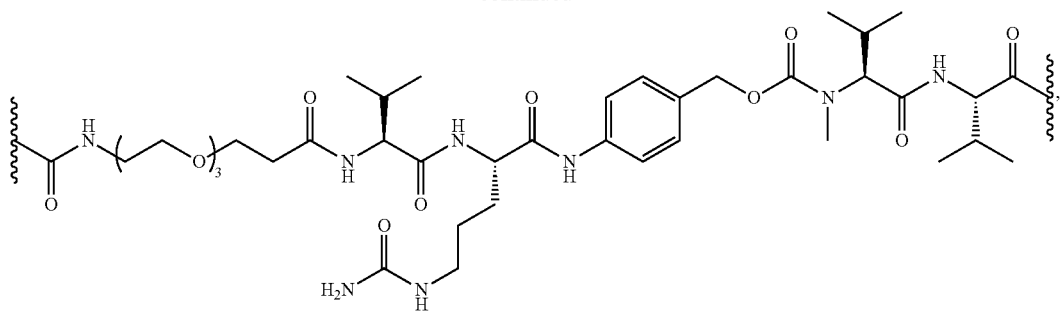
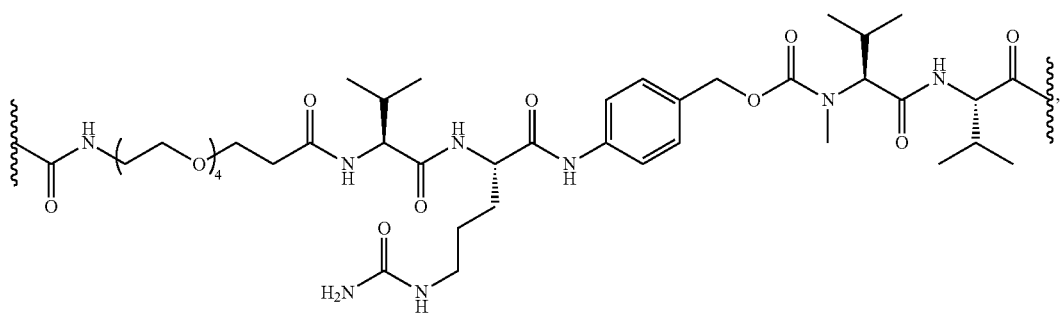
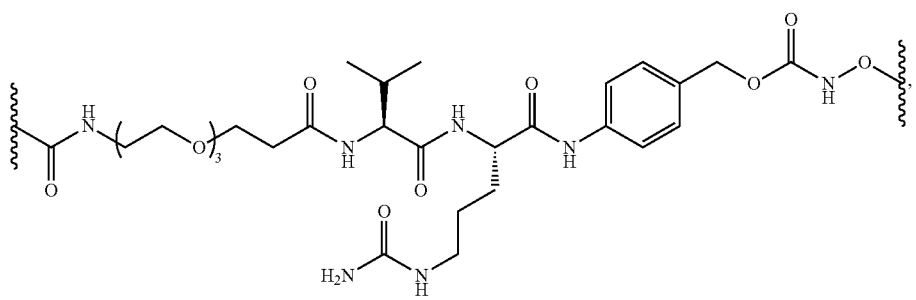
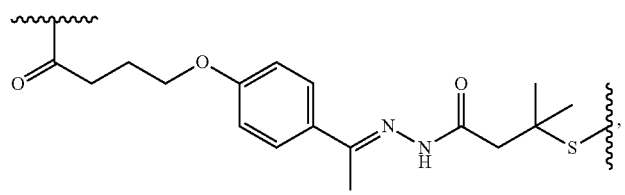
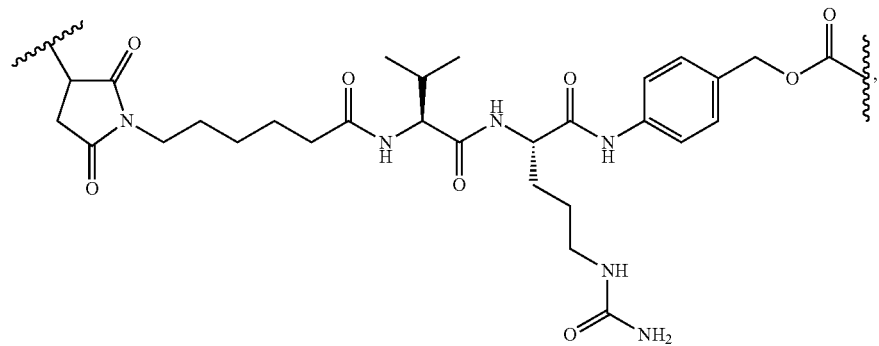

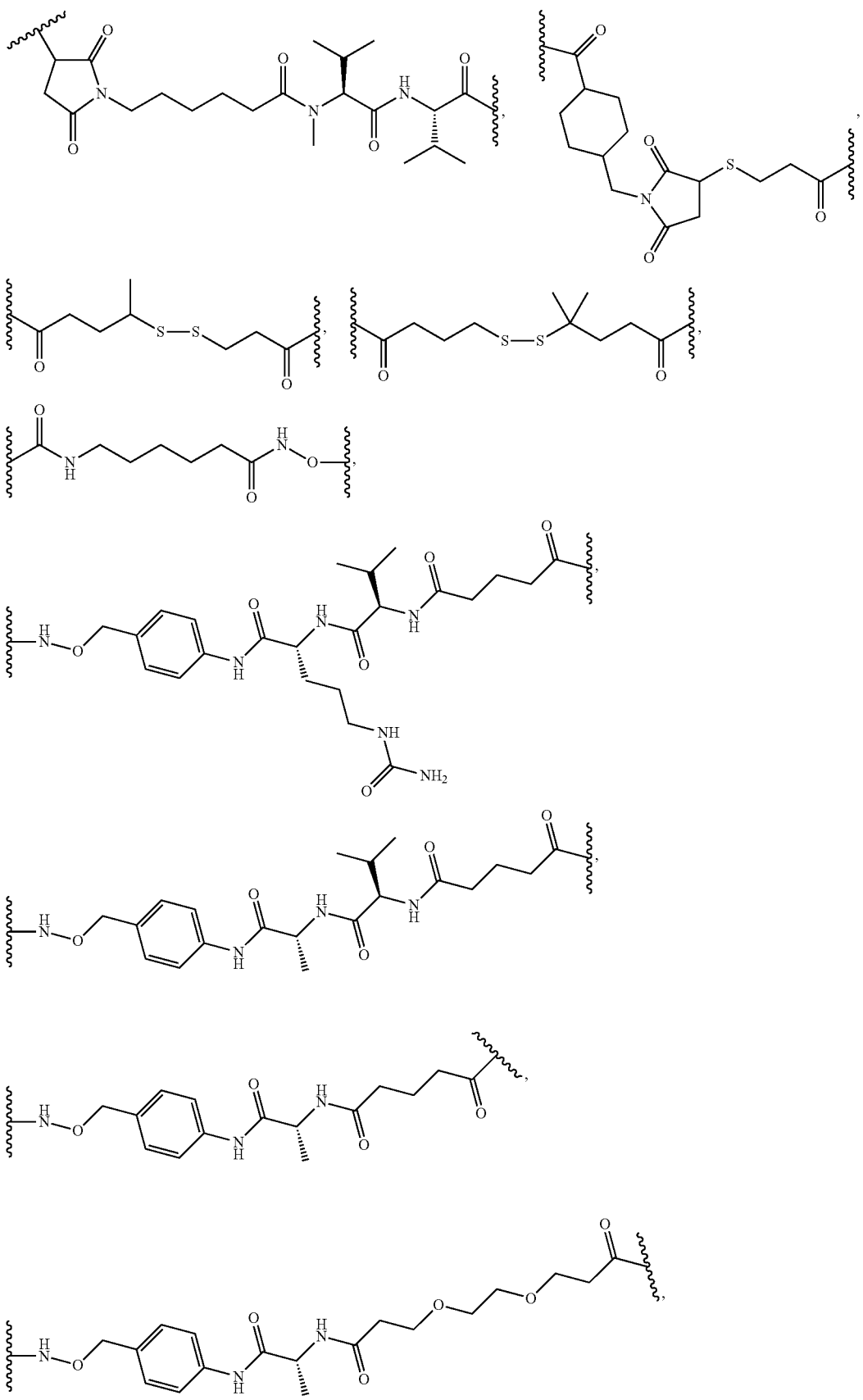

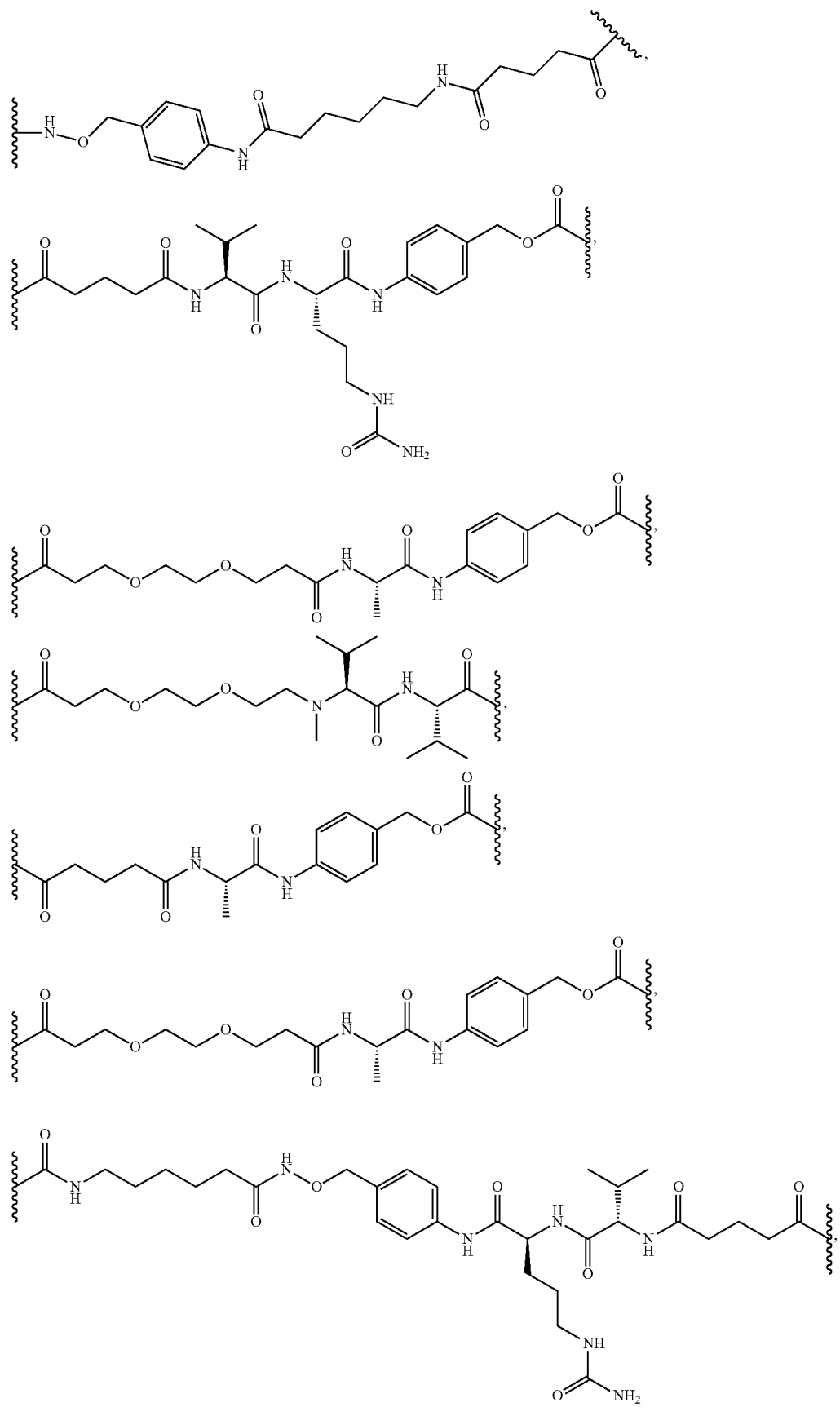

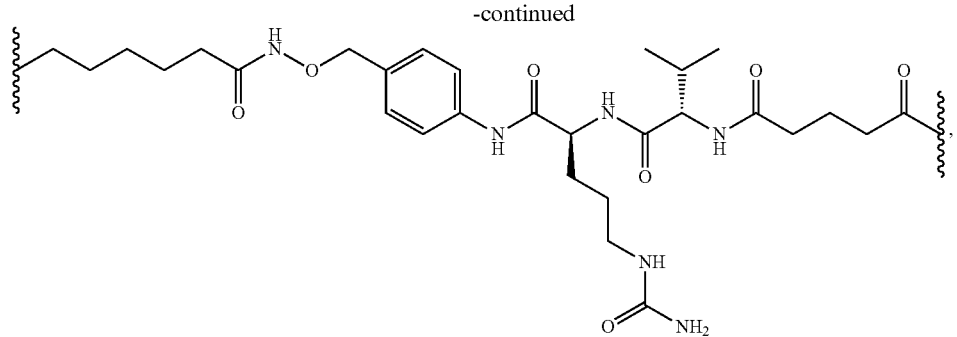
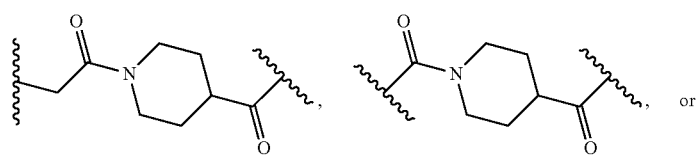
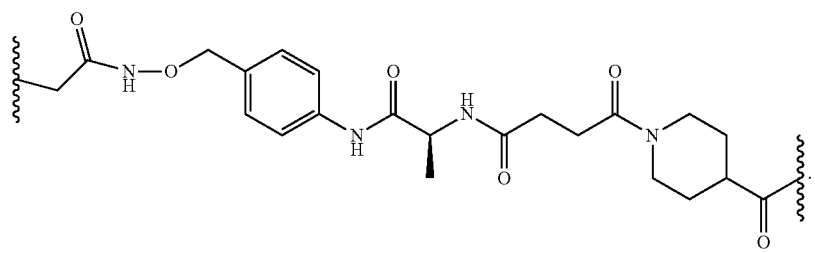
In some embodiments, the agent-conjugate having the structure of Formula I has the structure of
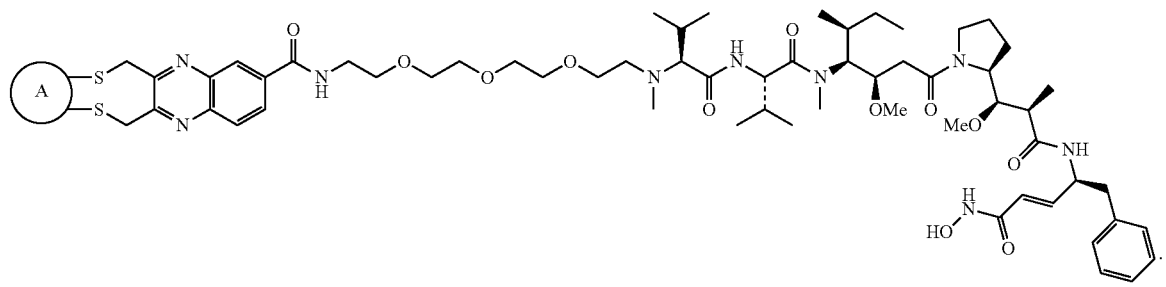
In some embodiments, the agent-conjugate having the structure of Formula I has the structure of
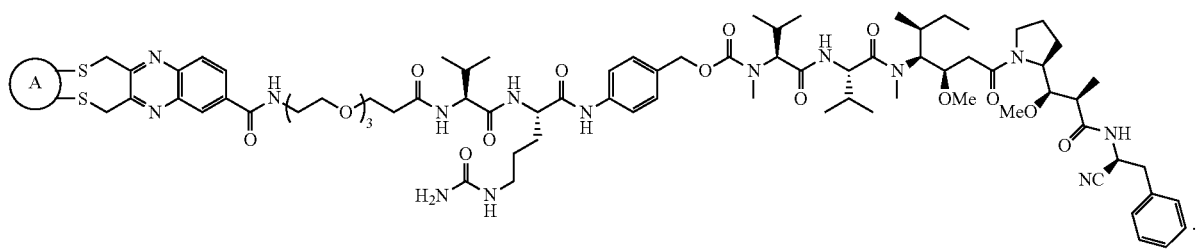

In some embodiments, the agent-conjugate having the structure of Formula I has the structure of
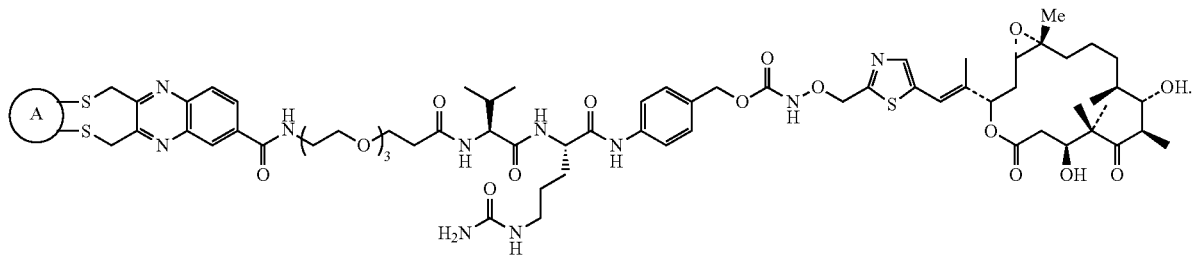
In some embodiments, the agent-conjugate having the structure of Formula I has the structure of
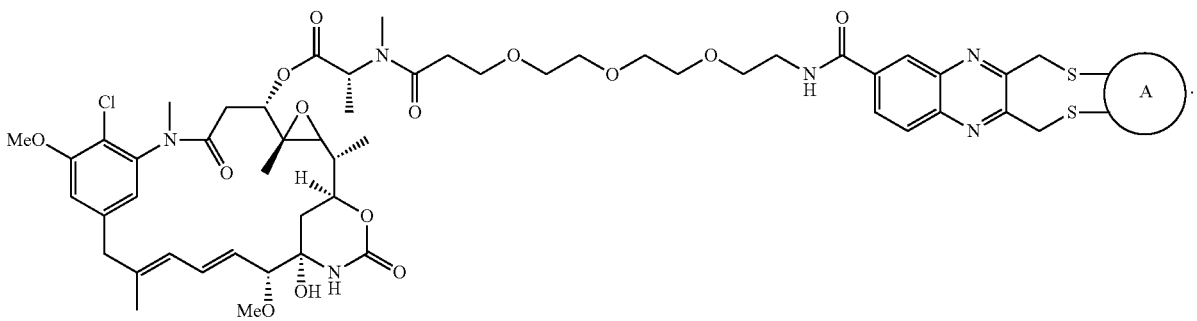
In some embodiments, the agent-conjugate having the structure of Formula I has the structure of
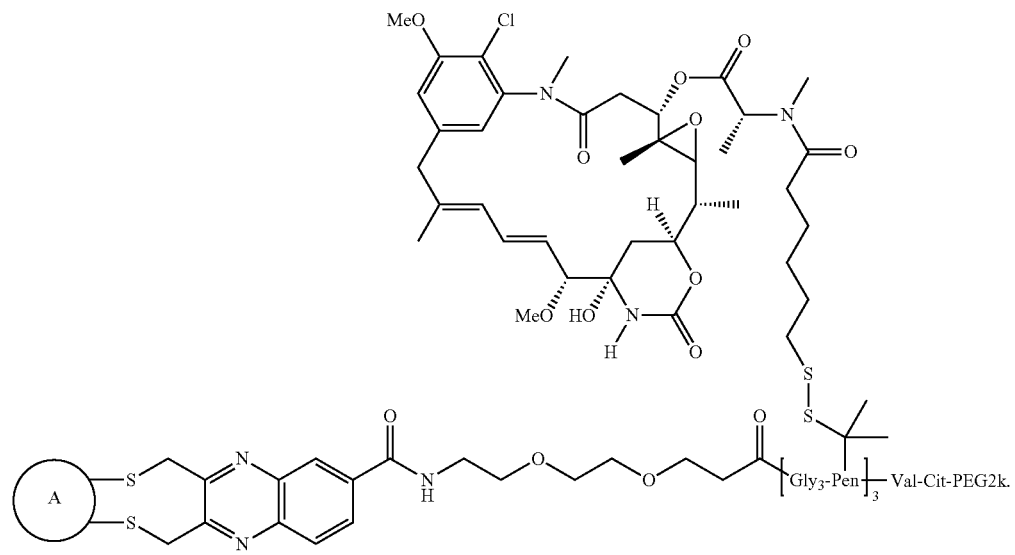

In some embodiments, the agent-conjugate having the structure of Formula I has the structure of
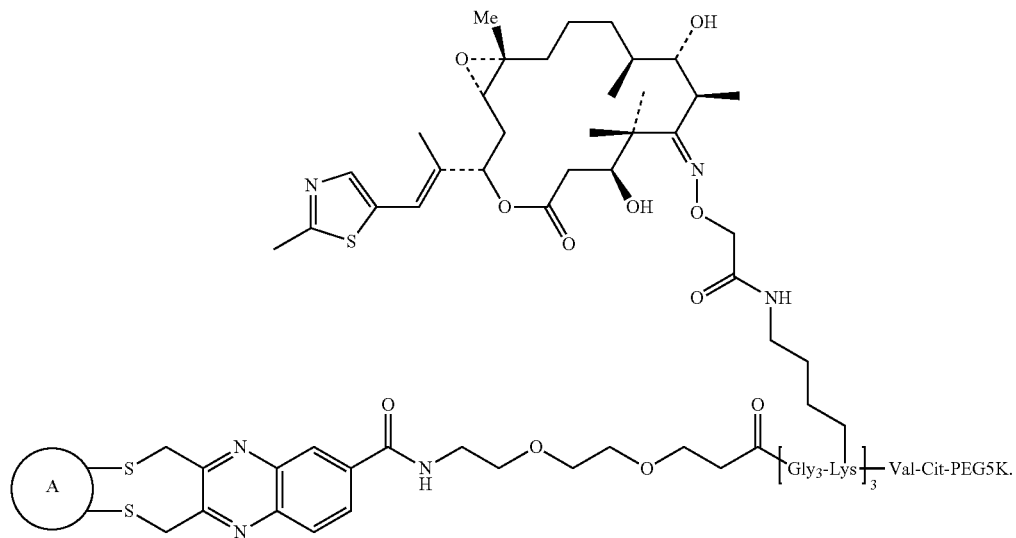
In some embodiments, the agent-conjugate having the structure of Formula I has the structure of
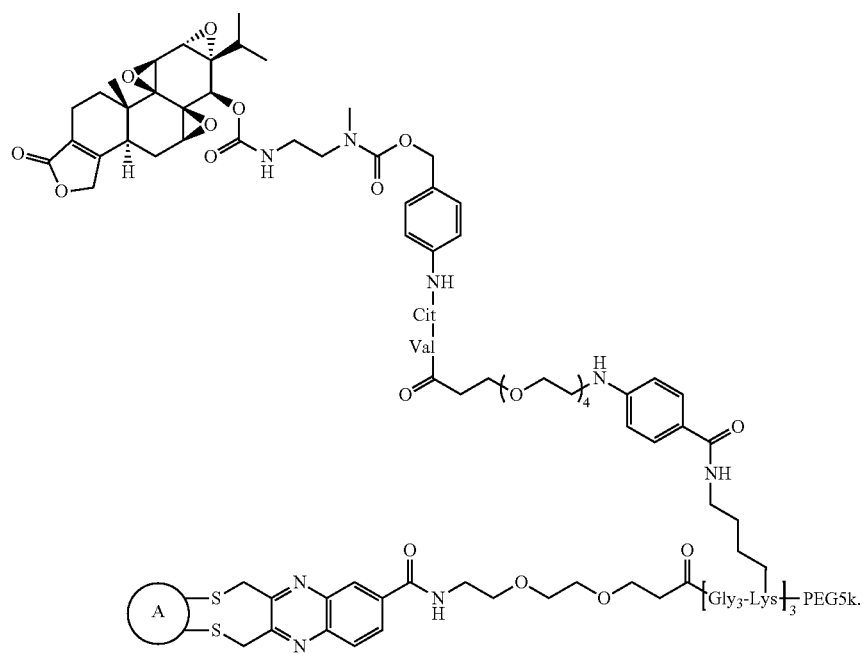
In some embodiments, the agent-conjugate having the structure of Formula I has the structure of

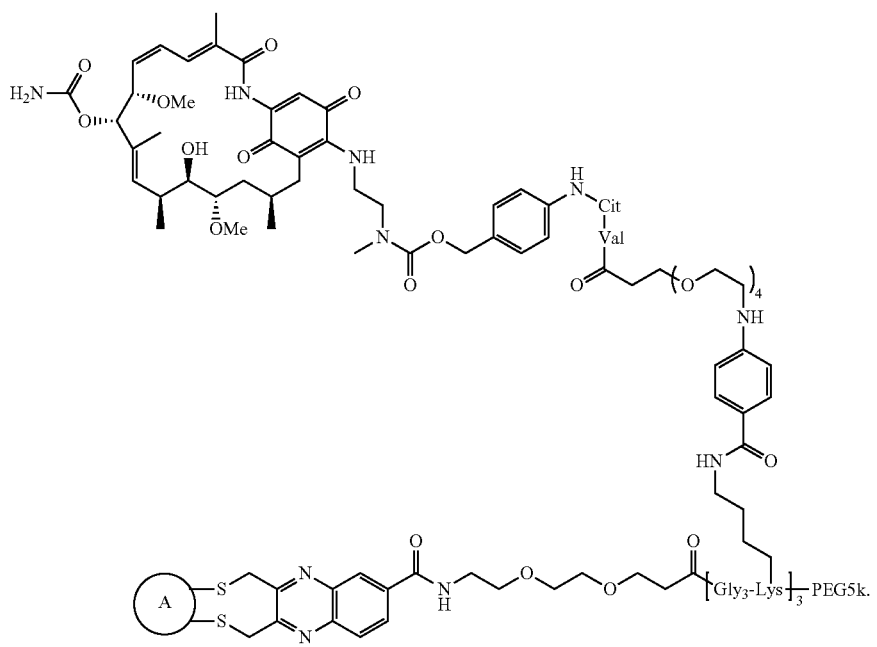

In some embodiments, the agent-conjugate having the structure of Formula I has the structure of

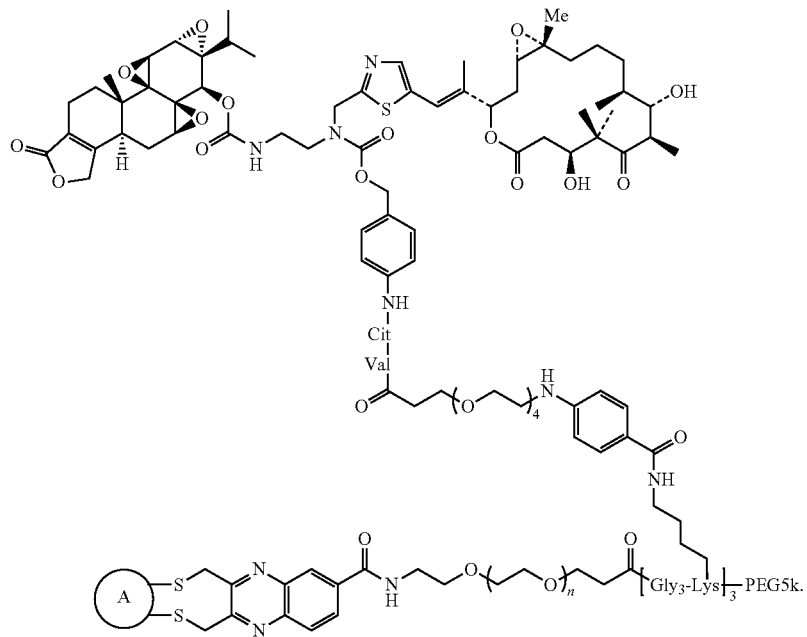

In some embodiments, the agent-conjugates may include one or more components selected from the group consisting of an amino acid, an amino acid residue, an amino acid analog, and a modified amino acid.

As used herein, the term "targeting moiety" refers to a structure that binds or associates with a biological moiety or fragment thereof.

In some embodiments, the targeting moiety may be an antibody. In some embodiments, the targeting moiety may be a monoclonal antibody (mAB). In some embodiments, the targeting moiety may be an antibody fragment, surrogate, or variant. In some embodiments, the targeting moiety may be a protein ligand. In some embodiments, the targeting moiety may be a protein scaffold. In some embodiments, the targeting moiety may be a peptide. In some embodiments, the targeting moiety may be RNA or DNA. In some embodiments, the targeting moiety may be a RNA or DNA fragment. In some embodiments, the targeting moiety may be a small molecule ligand.

In some embodiments, the targeting moiety may be an antibody fragment described in Janthur et al., "Drug Conjugates Such as Antibody Drug Conjugates (ADCs), Immunotoxins and Immunoliposomes Challenge Daily Clinical Practice," *Int. J. Mol. Sci.* 2012, 13, 16020-16045, the disclosure of which is incorporated herein by reference in its entirety. In some embodiments, the targeting moiety may be an antibody fragment described in Trail, P A, "Antibody Drug Conjugates as Cancer Therapeutics," *Antibodies* 2013, 2, 113-129, the disclosure of which is incorporated herein by reference in its entirety.

In some embodiments, the targeting moiety may be HuM195-Ac-225, HuM195-Bi-213, Anyara (naptumomab estafenatox; ABR-217620), AS1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544. In some embodiments, the targeting moiety may comprise, consist of, or consist essentially of the antibody portion of HuM195-Ac-225, HuM195-Bi-213, Anyara (naptumomab estafenatox; ABR-217620), AS 1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544.

In some embodiments, the targeting moiety may be Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

In some embodiments, the targeting moiety may comprise, consist of, or consist essentially of the antibody portion of Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

In some embodiments, the targeting moiety may comprise, consist of, or consist essentially of Brentuximab, Inotuzumab, Gemtuzumab, Milatuzumab, Trastuzumab, Glembatumomab, Lorvotuzumab, or Labestuzumab.

As used herein, the term "peptide" refers to a structure including one or more components each individually selected from the group consisting of an amino acid, an amino acid residue, an amino acid analog, and a modified amino acid. The components are typically joined to each other through an amide bond.

In some embodiments, the peptide, such as the antibody, is PEGylated. PEGylation can provide, for example, increased stability and/or efficacy of the polypeptide. Methods for PEGylation known in the art can be used in the methods and compositions provided herein. Such methods include, but are not limited to, those provided in "Comparative Binding of Disulfide-Bridged PEG-Fabs" Khalili et al., Bioconjugate Chemistry (2012), 23(11), 2262-2277; "Site-Specific PEGylation at Histidine Tags" Cong et al., Bioconjugate Chemistry (2012), 23(2), 248-263; "Disulfide bridge based PEGylation of proteins" Brocchini et al., Advanced Drug Delivery Reviews (2008), 60(1), 3-12; "Site-Specific PEGylation of Protein Disulfide Bonds Using a Three-Carbon Bridge" Balan et al., Bioconjugate Chemistry (2007), 18(1), 61-76; "Site-specific PEGylation of native disulfide bonds in therapeutic proteins" Shaunak et al., Nature Chemical Biology (2006), 2(6), 312-313; "PEG derivative conjugated proteins and peptides for use in pharmaceuticals" Godwin et al., WO 2010/100430. All of the aforementioned PEGylation references are incorporated by references in their entireties.

As used herein, the term "amino acid" includes naturally occurring amino acids, a molecule having a nitrogen available for forming an amide bond and a carboxylic acid, a molecule of the general formula $NH_2$—CHR—COOH or the residue within a peptide bearing the parent amino acid, where "R" is one of a number of different side chains. "R" can be a substituent found in naturally occurring amino acids. "R" can also be a substituent referring to one that is not of the naturally occurring amino acids.

As used herein, the term "amino acid residue" refers to the portion of the amino acid which remains after losing a water molecule when it is joined to another amino acid.

As used herein, the term "amino acid analog" refers to a structural derivative of an amino acid parent compound that often differs from it by a single element.

As used herein, the term "modified amino acid" refers to an amino acid bearing an "R" substituent that does not correspond to one of the twenty genetically coded amino acids.

As used herein, the abbreviations for the genetically encoded L-enantiomeric amino acids are conventional and are as follows: The D-amino acids are designated by lower case, e.g. D-proline=p, etc.

TABLE 1

| Amino Acids | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Certain amino acid residues in the active agent-conjugate can be replaced with other amino acid residues without significantly deleteriously affecting, and in many cases even enhancing, the activity of the peptides. Thus, also contemplated by the preferred embodiments are altered or mutated forms of the active agent-conjugate wherein at least one defined amino acid residue in the structure is substituted with another amino acid residue or derivative and/or analog thereof. It will be recognized that in preferred embodiments, the amino acid substitutions are conservative, i.e., the replacing amino acid residue has physical and chemical properties that are similar to the amino acid residue being replaced.

For purposes of determining conservative amino acid substitutions, the amino acids can be conveniently classified into two main categories—hydrophilic and hydrophobic—depending primarily on the physical-chemical characteristics of the amino acid side chain. These two main categories can be further classified into subcategories that more distinctly define the characteristics of the amino acid side chains. For example, the class of hydrophilic amino acids can be further subdivided into acidic, basic and polar amino acids. The class of hydrophobic amino acids can be further subdivided into nonpolar and aromatic amino acids. The definitions of the various categories of amino acids are as follows:

The term "hydrophilic amino acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Thr (T), Ser (S), His (H), Glu (E), Asn (N), Gln (Q), Asp (D), Lys (K) and Arg (R).

The term "hydrophobic amino acid" refers to an amino acid exhibiting a hydrophobicity of greater than zero according to the normalized consensus hydrophobicity scale of Eisenberg, 1984, J. Mol. Biol. 179:1.25-142. Genetically encoded hydrophobic amino acids include Pro (P), Ile (I), Phe (F), Val (V), Leu (L), Trp (W), Met (M), Ala (A), Gly (G) and Tyr (Y).

The term "acidic amino acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

The term "basic amino acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

The term "polar amino acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

The term "nonpolar amino acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Leu (L), Val (V), Ile (I), Met (M), Gly (G) and Ala (A).

The term "aromatic amino acid" refers to a hydrophobic amino acid with a side chain having at least one aromatic or heteroaromatic ring. In some embodiments, the aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

The term "aliphatic amino acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfanyl-containing amino acids. The ability of Cys (C) residues (and other amino acids with —SH containing side chains) to exist in a peptide in either the reduced free —SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes of the preferred embodiments Cys (C) is categorized as a polar hydrophilic amino acid, notwithstanding the general classifications defined above.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

While the above-defined categories have been exemplified in terms of the genetically encoded amino acids, the amino acid substitutions need not be, and in certain embodiments preferably are not, restricted to the genetically encoded amino acids. In some embodiments, the active agent-conjugate may contain genetically non-encoded amino acids. Thus, in addition to the naturally occurring genetically encoded amino acids, amino acid residues in the active agent-conjugate may be substituted with naturally occurring non-encoded amino acids and synthetic amino acids.

Certain commonly encountered amino acids which provide useful substitutions for the active agent-conjugates include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-phenylphenylalanine, 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe (pNH$_2$)); N-methyl valine (MeVal); homocysteine (hCys), homophenylalanine (hPhe) and homoserine (hSer); hydroxyproline (Hyp), homoproline (hPro), N-methylated amino acids and peptoids (N-substituted glycines).

Other amino acid residues not specifically mentioned herein can be readily categorized based on their observed physical and chemical properties in light of the definitions provided herein.

The classifications of the genetically encoded and common non-encoded amino acids according to the categories defined above are summarized in Table 2, below. It is to be understood that Table 2 is for illustrative purposes only and does not purport to be an exhaustive list of amino acid residues and derivatives that can be used to substitute the active agent-conjugate described herein.

TABLE 2

CLASSIFICATIONS OF COMMONLY ENCOUNTERED AMINO ACIDS

| Classification | Genetically Encoded | Non-Genetically Encoded |
| --- | --- | --- |
| Hydrophobic | | |
| Aromatic | F, Y, W | Phg, Nal, Thi, Tic, Phe (4-Cl), Phe (2-F), Phe (3-F), Phe (4-F), hPhe |
| Nonpolar | L, V, I, M, G, A, P | t-BuA, t-BuG, MeIle, Nle, MeVal, Cha, McGly, Aib |
| Aliphatic | A, V, L, I | b-Ala, Dpr, Aib, Aha, MeGly, t-BuA, t-BuG, MeIle, Cha, Nle, MeVal |
| Hydrophilic | | |
| Acidic | D, E | |
| Basic | H, K, R | Dpr, Orn, hArg, Phe(p-NH$_2$), Dbu, Dab |
| Polar | C, Q, N, S, T | Cit, AcLys, MSO, bAla, hSer |
| Helix-Breaking | P, G | D-Pro and other D-amino acids (in L-peptides) |

Other amino acid residues not specifically mentioned herein can be readily categorized based on their observed physical and chemical properties in light of the definitions provided herein.

While in most instances, the amino acids of the active agent-conjugate will be substituted with L-enantiomeric amino acids, the substitutions are not limited to L-enantiomeric amino acids. In some embodiments, the peptides may advantageously be composed of at least one D-enantiomeric amino acid. Peptides containing such D-amino acids are thought to be more stable to degradation in the oral cavity, gut or serum than are peptides composed exclusively of L-amino acids.

Conjugation Methods
One-Step Conjugation

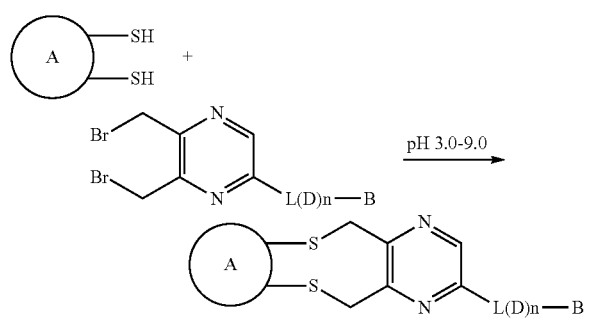

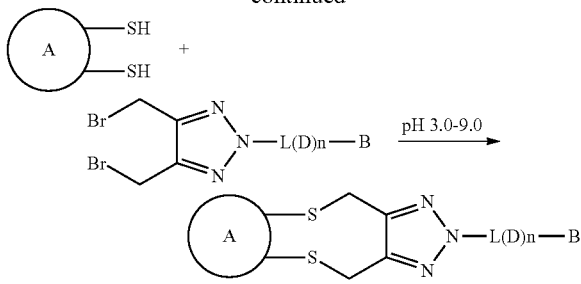

Two-Step Conjugation, Drug Preloaded

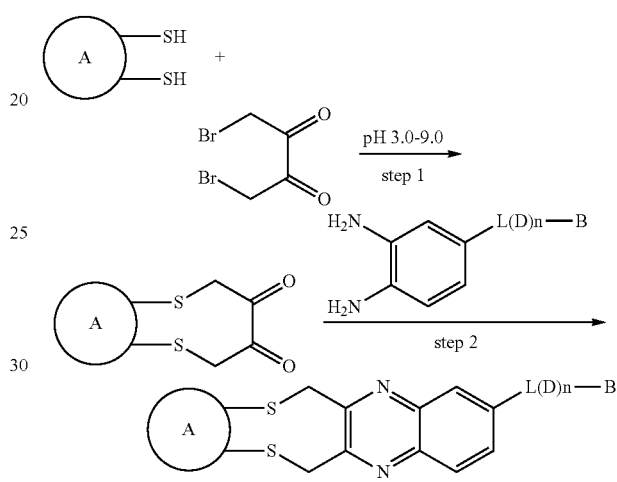

Two-Step Conjugation, Drug Added at the Last Step

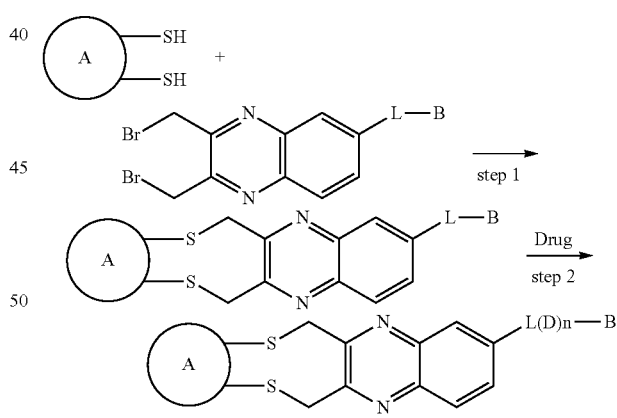

Examples of One-Step Conjugation

General procedure I

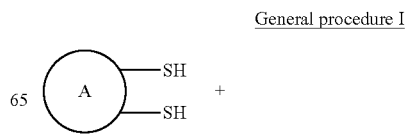

43
-continued
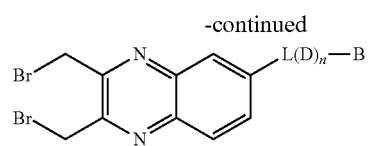
44
-continued
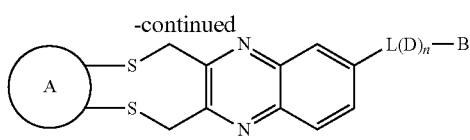
Examples Include, but are not Limited
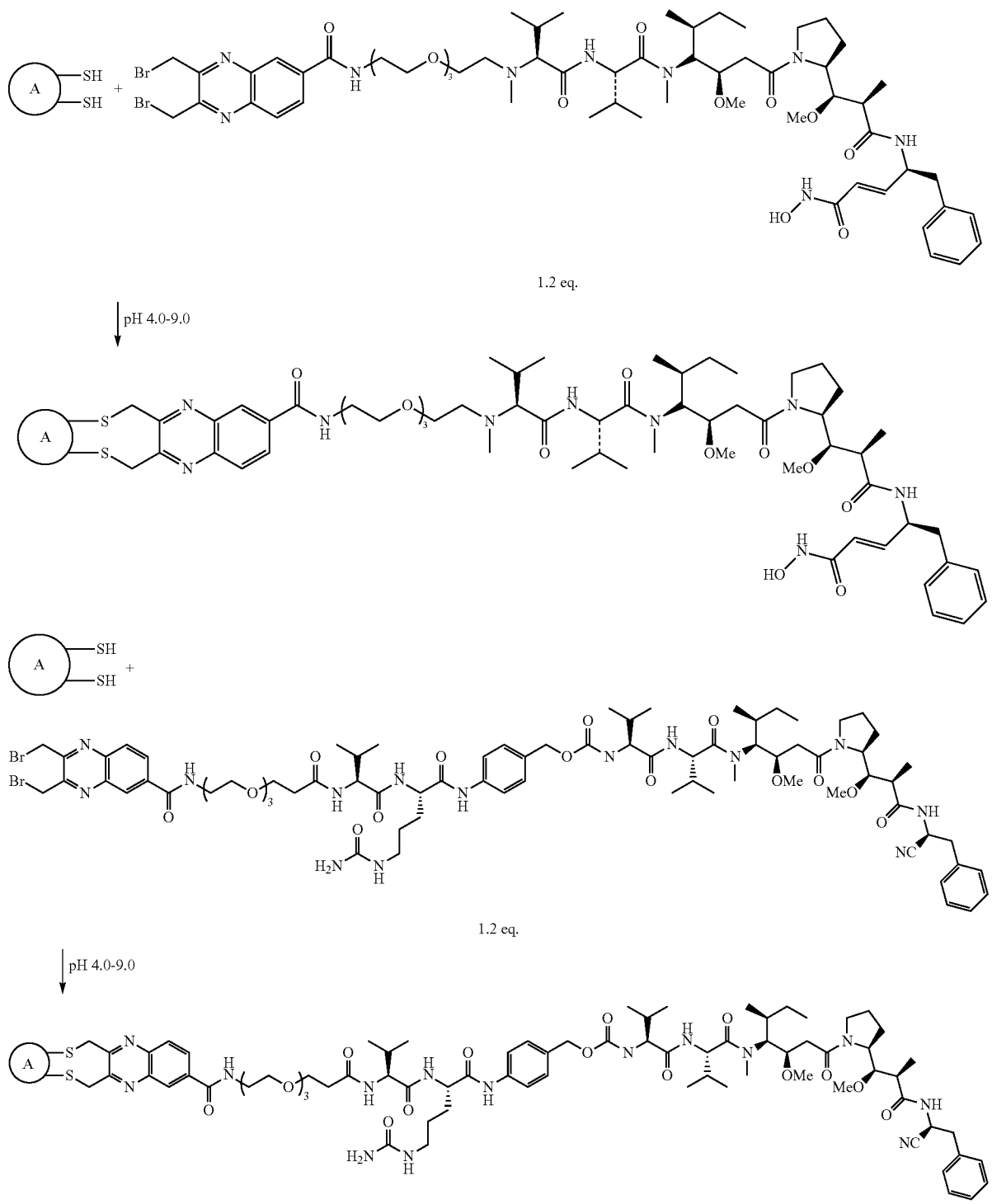

Additional compounds that can be made according to the General procedures include, but are not limited to, the following:
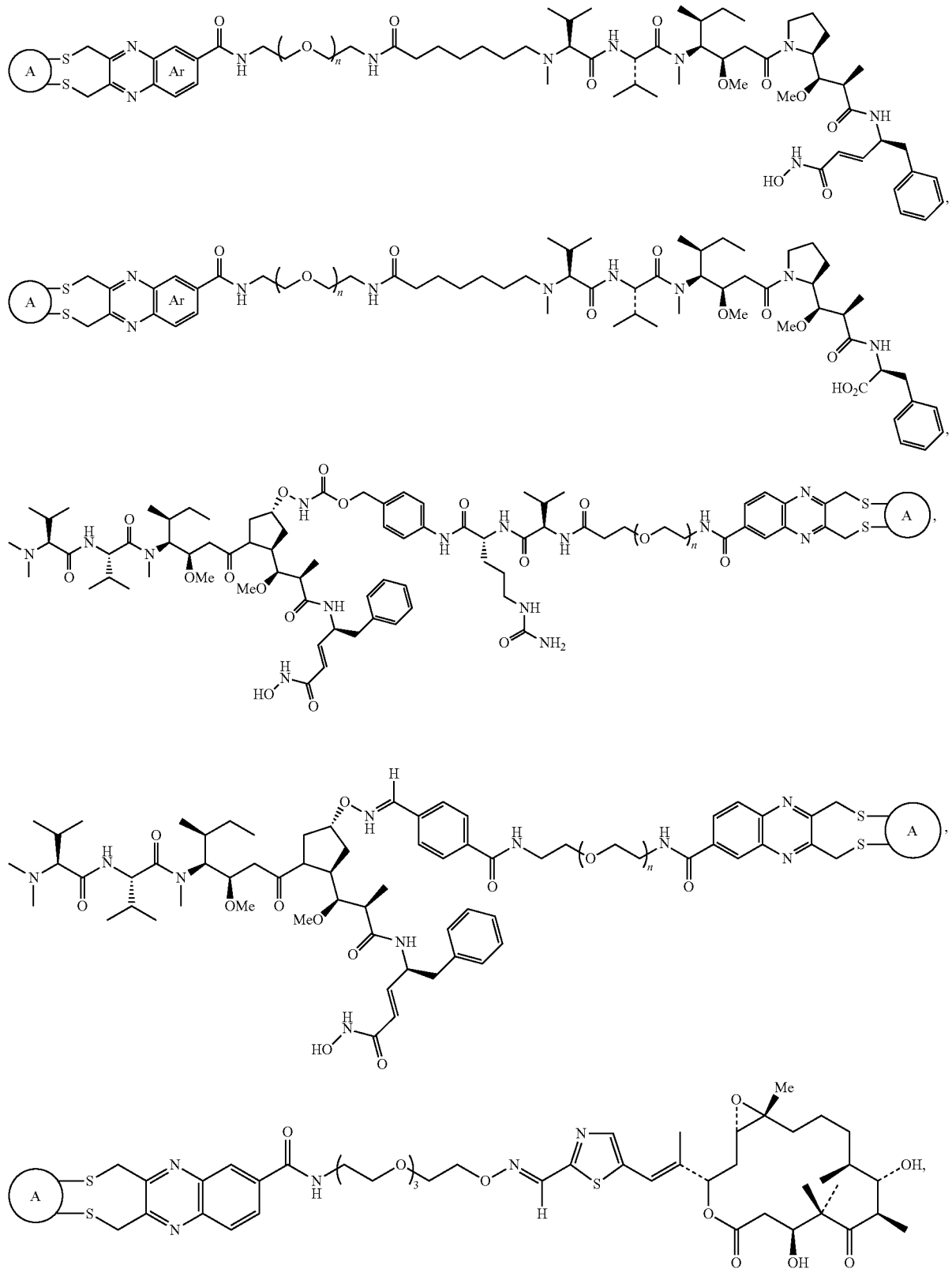

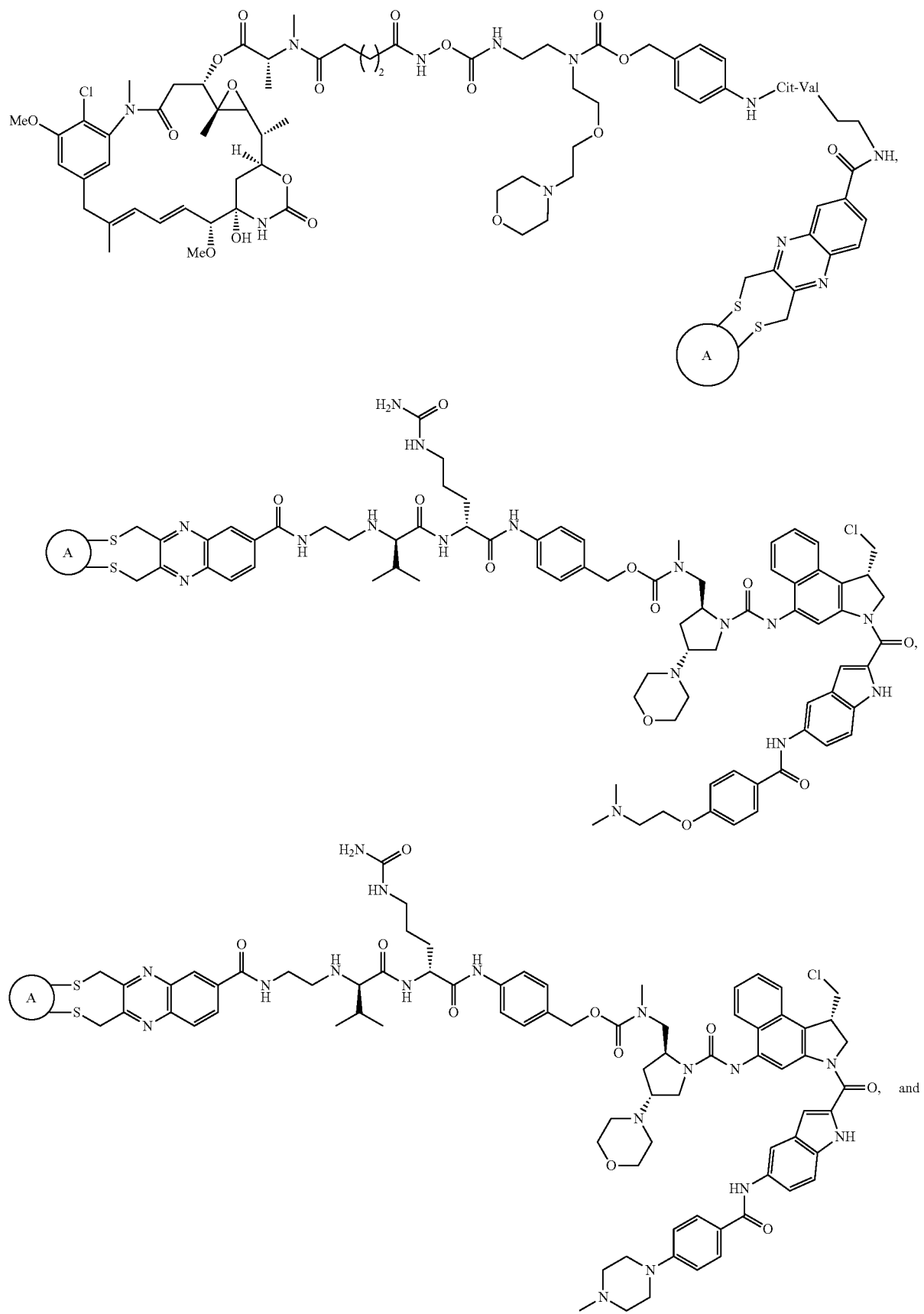

-continued
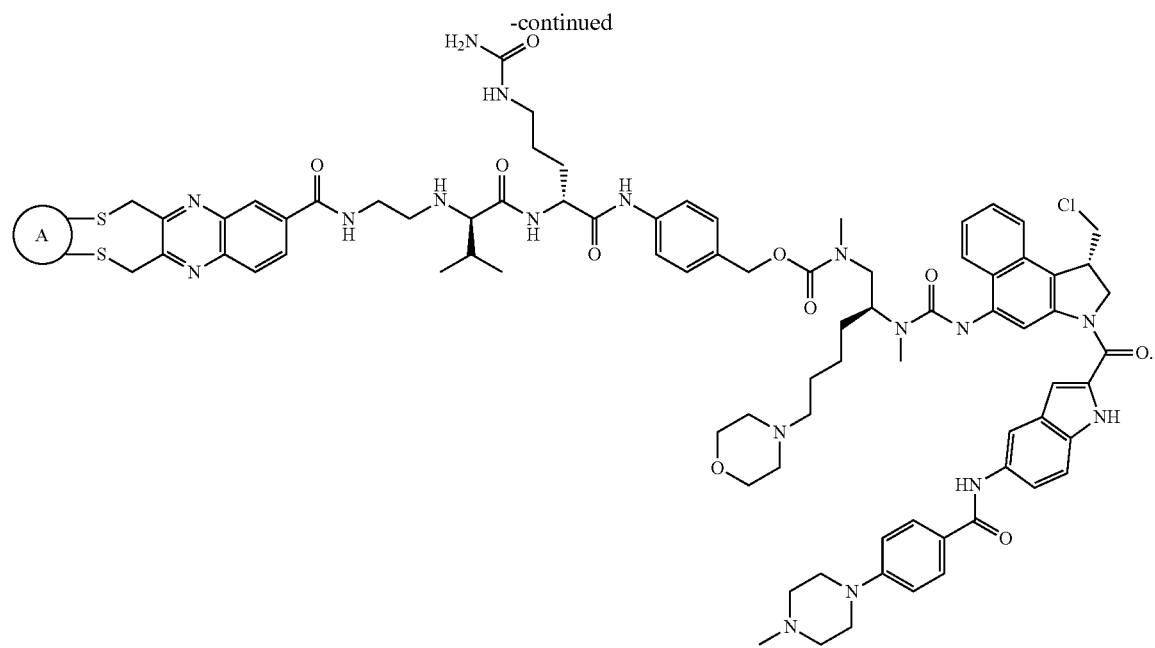
Examples Include, but are not Limited, the Following

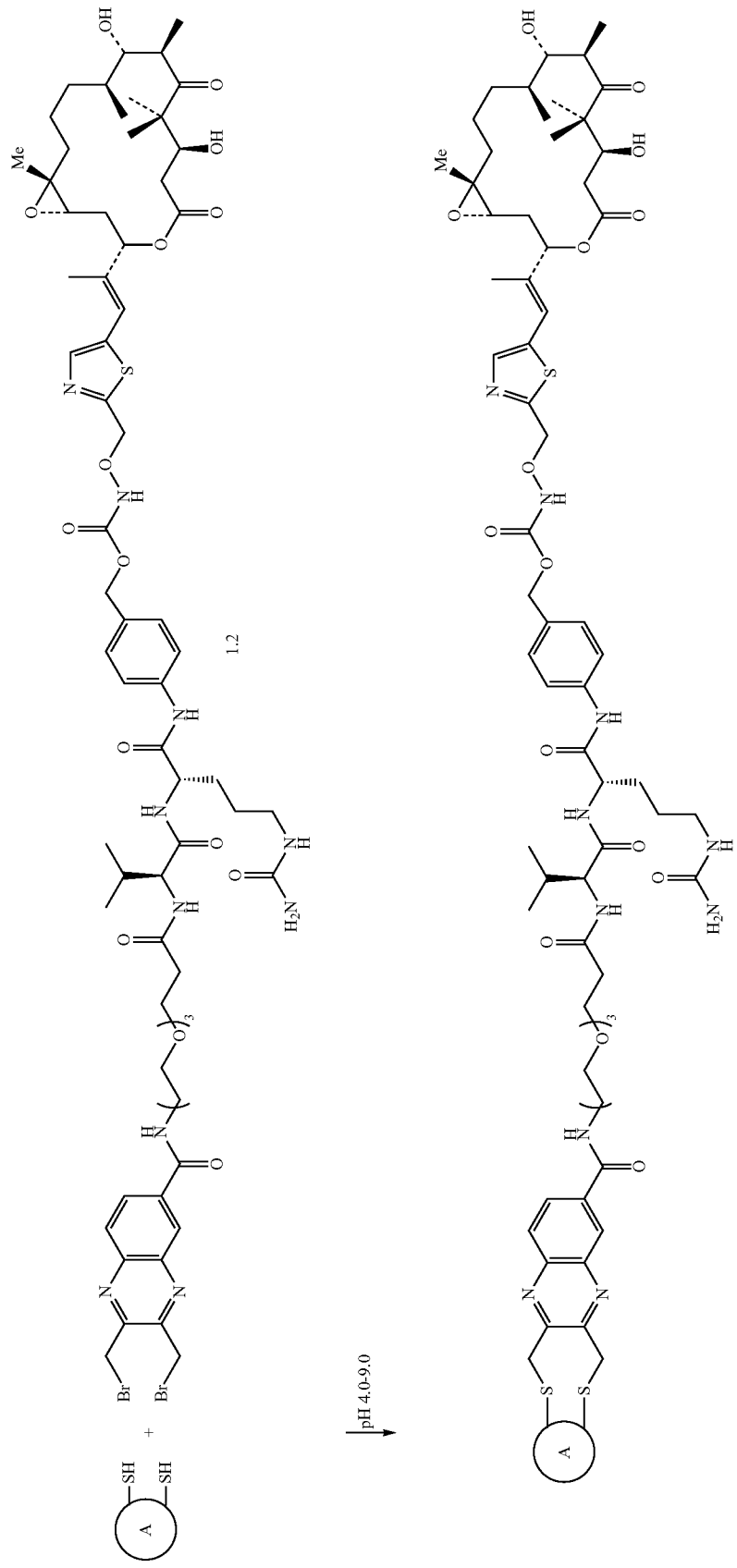

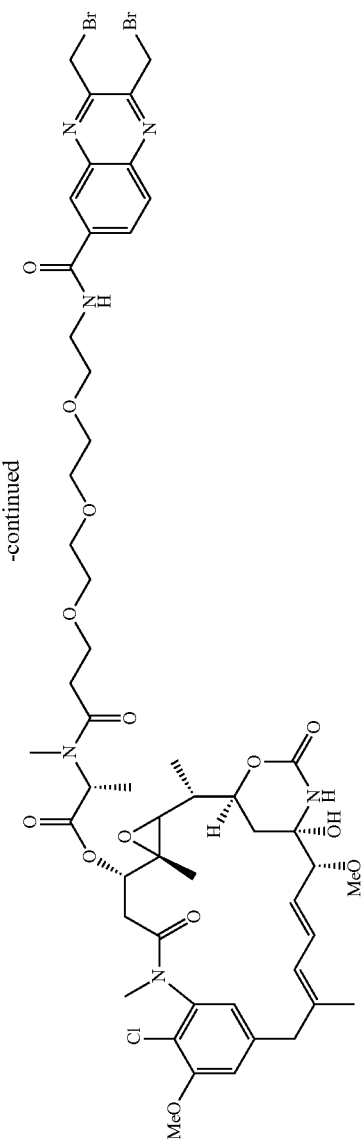
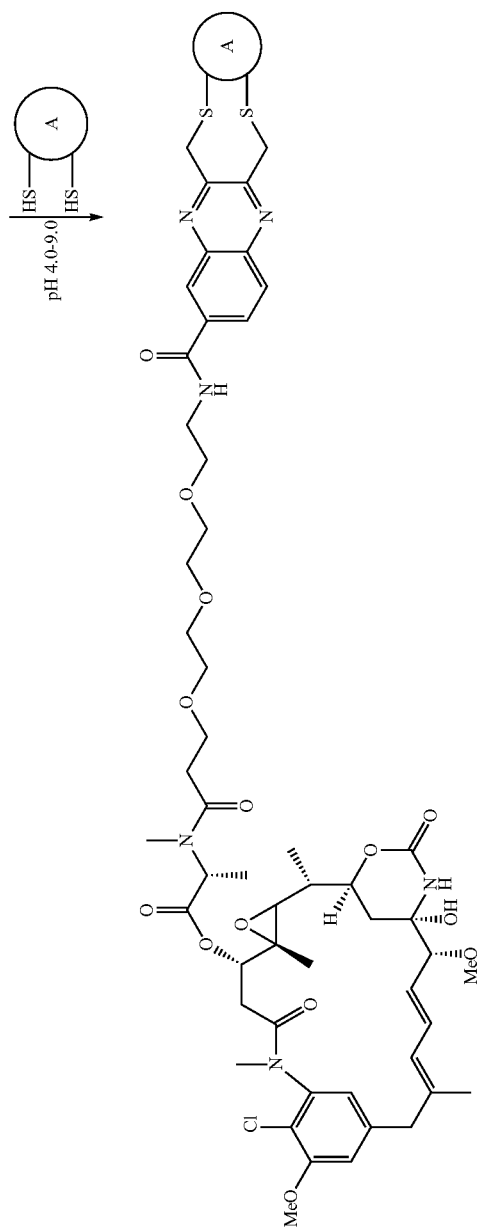

Two-Step Conjugation, Drugs Preloaded Approach:
Conjugation Method
General Scheme II
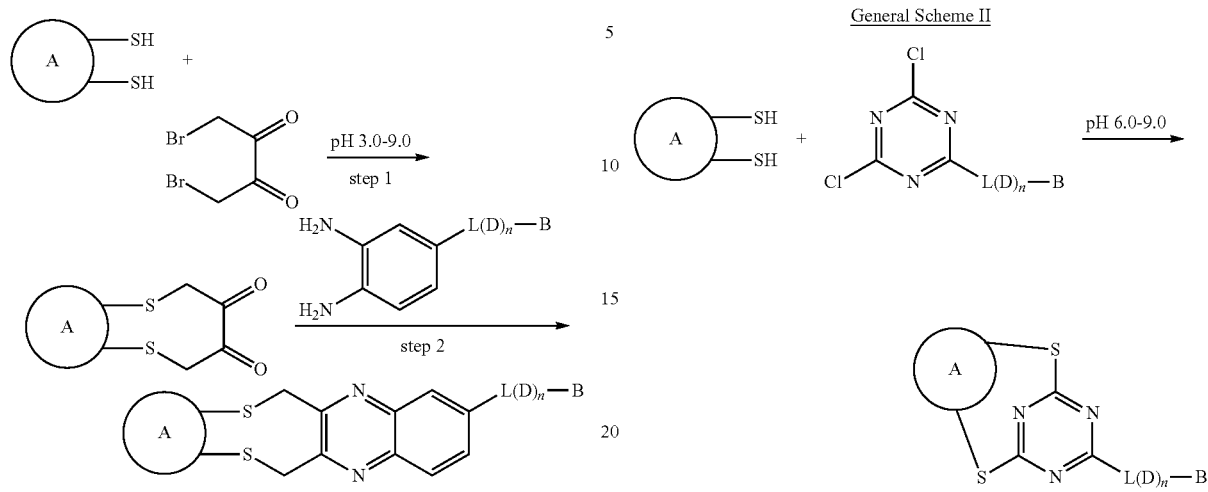
Examples Include, but are not Limited to, the Following
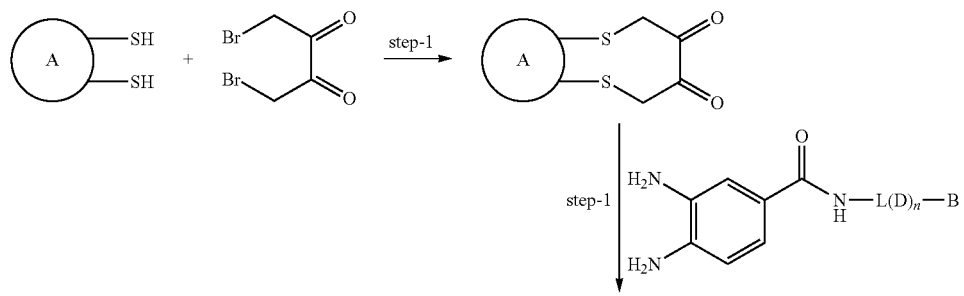
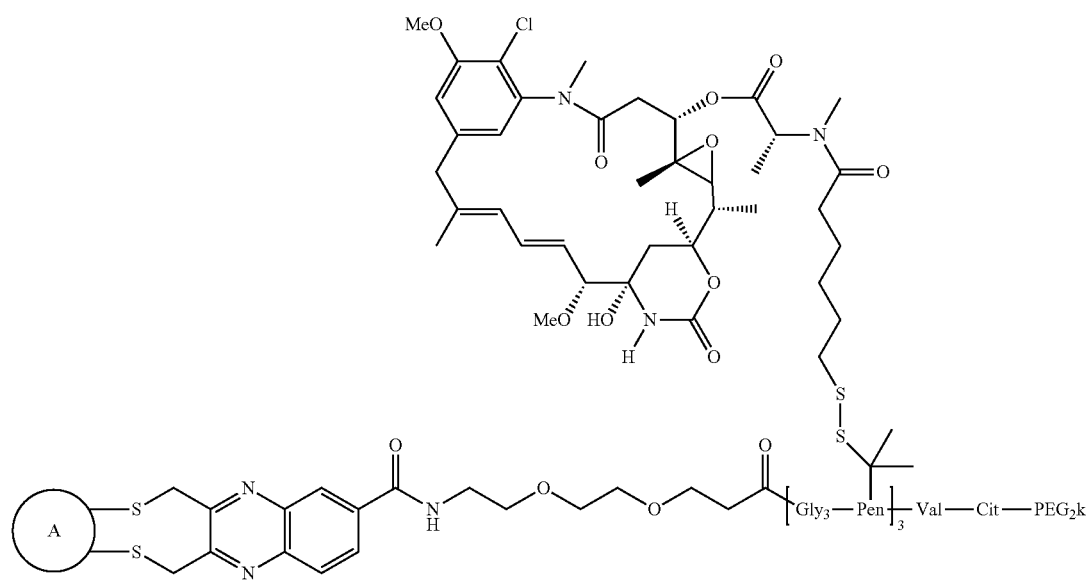

Examples Include, but are not Limited to the Following

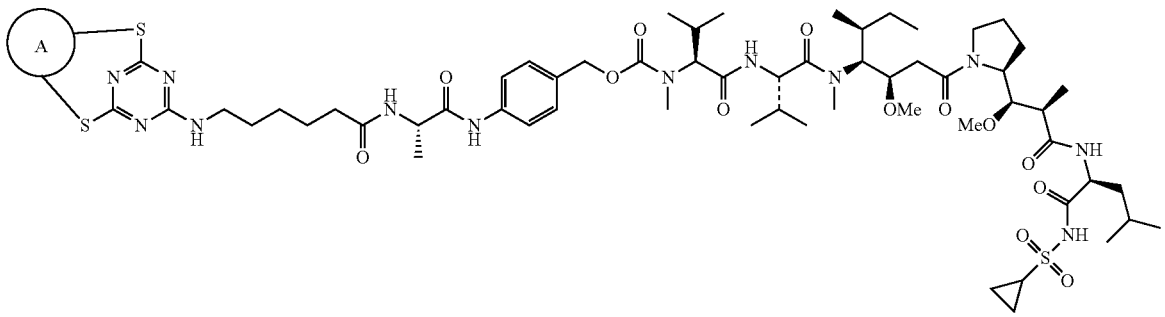

Conjugation Method

General Scheme III

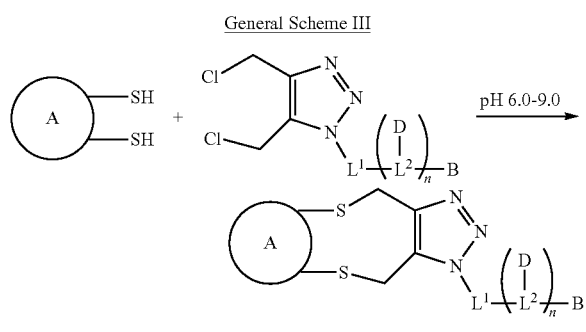

Examples Include, but are not Limited to, the Following

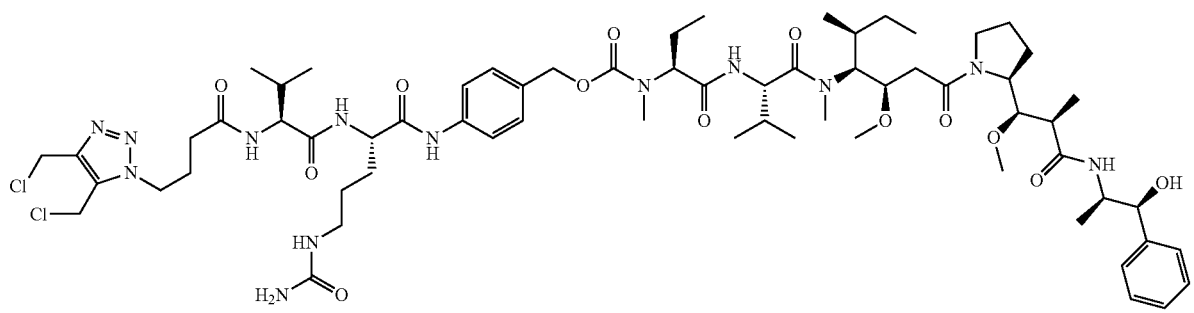 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](CC)N(C)C(=O)OCc1ccc(NC(=O)[C@H](CCCNC(N)=O)NC(=O)[C@@H](NC(=O)CCCn2nnc(CCl)c2CCl)C(C)C)cc1)C(C)C]

Examples

Antibody-Drug Conjugation

General Conjugation Procedure

To a target antibody, 0.5-50 mgs/mL, in a certain buffet at pH 5.0-9.0, such as PBS, was added 0.5-100 eq of reducing agent such as TCEP and DTT. The reduction was performed at 0-40° C. for 0.5-40 hours with gentle stirring or shaking, and then the reducing agent was removed by column or ultrafiltration. To the partially reduced antibody, 0.5-50 mgs/mL, in a certain buffet at pH 5.0-9.0, such as PBS, with 0-30% of organic co-solvent such as DMA, was added 0.5-10 eq of the activated drug-linker bearing a dibromo or dichloro-functionality. The reaction was conducted at 0-40° C. for 0.5-40 hours with gentle stirring or shaking, monitored by HIC-HPLC. The resultant crude ADC product underwent necessary down-stream steps of desalt, buffet changes/formulation, and optionally, purification, using the state-of-art procedures. The final ADC product was characterized by HIC-HPLC, SEC, RP-HPLC, and optionally LC-MS. The average DAR was calculated by UV absorption and/or MS spectroscopy.

General Synthetic Procedures

General Procedure A—HATU Mediated Amide Bond Formation

To an acid (1.1 eq with respect to amine) in anhydrous DMF was added HATU (1 eq with respect to acid) and DIEA (2 eq with respect to acid) and the mixture was stirred at room temperature for 1 minute. The mixture was then added to a solution of amine in DMF and the reaction mixture was stirred at room temperature till the completion of the reaction (monitored by LC/MS). The solvent was removed under reduced pressure and the residue was optionally purified by reverse phase HPLC to give final pure product.

General Procedure B—DIC/HOAt Mediated Amide Bond Formation

To a stirred solution of carboxylic acid (1.1 eq), amine and HOAt (1.1 eq) in anhydrous DMF was added DIC (1.1 eq) and the reaction mixture was stirred at room temperature. Upon completion (monitored by LC/MS), the solvent was removed under reduced pressure and the residue was optionally purified by reverse phase HPLC to give final pure product.

General Procedure C—Removal of Acid Sensitive Protecting Groups (Boc, THP, t-Bu) Using HCl/Dioxane The acid sensitive protecting groups containing compound was dissolved in 4N HCl/dioxane and the mixture was stirred at room temperature for 2 h. The solution was then concentrated under reduced pressure and the residue was washed twice with cold ether. Purification was carried out on reverse phase HPLC if necessary.

General Procedure D—Removal of Fmoc Group

The Fmoc containing compound was dissolved in 2-5% piperidine in DMF. The mixture was stirred at room temperature for 1 h. The solvents were removed under reduced pressure. Purification was carried out on reverse phase HPLC if necessary.

General Procedure E—Reductive Alkylation

An amine was dissolved in DMF and aldehyde (5 eq) was added, followed by addition of sodium cyanoborohydride (5 eq). HOAc was added to adjust the pH of the reaction mixture to 4-5. The mixture was stirred at room temperature till completion (1-4 h, monitored by HPLC). Purification was carried out on reverse phase HPLC if necessary.

General Procedure F—Saponification—Removal of Me/et from Esters

To a stirred solution of an ester in MeOH was added 1M aq. solution of LiOH till pH of the mixture was about 13-14 and the reaction mixture was stirred at room temperature till completion (~16 h, monitored by HPLC). Citric acid (~10% aq,) was added to neutralize the reaction and the solvents were removed under reduced pressure. The crude product was optionally purified by RP-HPLC or used directly in the next step.

General Procedure G—Activation of a Hydroxyl/Phenol Group with Bis(p-Nitrophenyl)Carbonate To a stirred solution of an alcohol/phenol in THF/DMF (2/1) was added bis(p-nitrophenyl) carbonate (3-5 eq), followed by DIEA (2-4 eq) and the reaction mixture was stirred at room temperature until most of the starting material was consumed. The progress of the reaction was monitored by LC/MS. The crude product was optionally purified by flash column chromatography or by precipitation and washing.

General Procedure H—Reaction of an Amine with a Cyclic Anhydride (Glutaric Anhydride or Succinic Anhydride)

An amine containing compound was dissolved in DMF. Glutaric anhydride (3 eq) was added, followed by addition of DIEA (4 eq). The reaction mixture was stirred at room temperature until most of the starting material was consumed. The progress of the reaction was monitored by LC/MS. The crude product was purified by RP-HPLC to yield the pure carboxylic acid.

General Procedure I—Formation of Carbamate with p-Nitrophenyl Carbonate (e.g. FmocVC-PAB-PNP)

An amine containing compound was dissolved in DMF and alkyl/aryl p-nitrophenyl carbonate (1.5 eq) was added, followed by addition of DIEA (2 eq) and HOBt (cat., 5%). The reaction mixture was stirred at room temperature until most of the amine was consumed. The progress of the reaction was monitored by LC/MS. The crude product was optionally purified by RP-HPLC to yield the pure carbamate.

General Procedure J—Formation of an Activated Ester (e.g. NHS) from an Acid

An acid was dissolved in DCM and DMF was added to aid dissolution if necessary. N-hydroxysuccinimide (1.5 eq) was added, followed by EDC.HCl (1.5 eq). The reaction mixture was stirred at room temperature for 1 h until most of the acid was consumed. The progress of the reaction was monitored by RP-HPLC. The mixture was then diluted with DCM and washed successively with citric acid (aq. 10%) and brine. The organic layer was dried and concentrated to dryness. The crude product was optionally purified by RP-HPLC or silica gel column chromatography.

Conjugation Method

Conjugation on two Cys residues by forming a cyclic structure

Two-Step Method

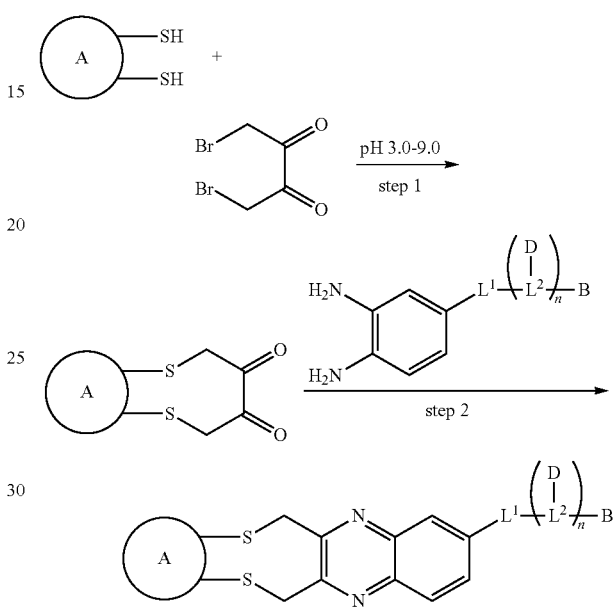

One-Step Method

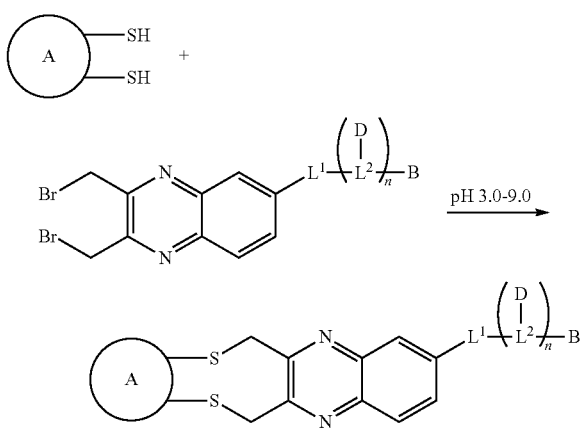

Triazole One Step Method

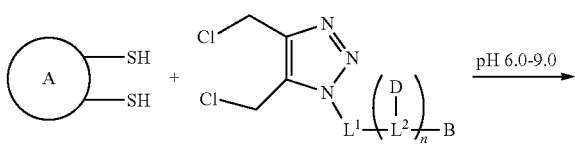

61
-continued

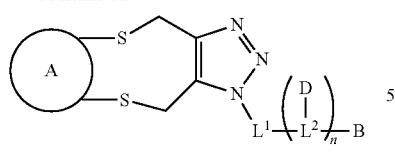

62
-continued

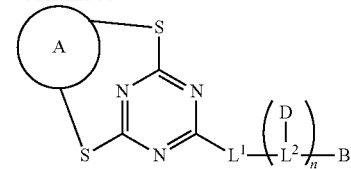

Triazine One Step Method

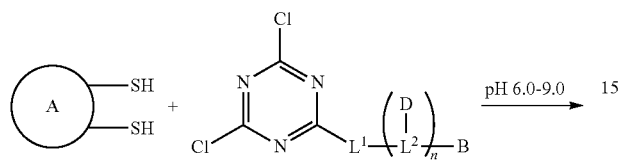

Experimental Description

Step 1. Drug-Linker Construct Synthesis (-L²-D)
Methods of Drug-Linker Construct Synthesis, but No Limited to:
Method 1-1: Linker and Drug Connected Via a Carbamate Bond Using General Procedure G or I for Activation and Carbamate Formation and General Procedure C, D, or F for Removal of Protective Groups.

GENERAL PROCEDURE SCHEME I

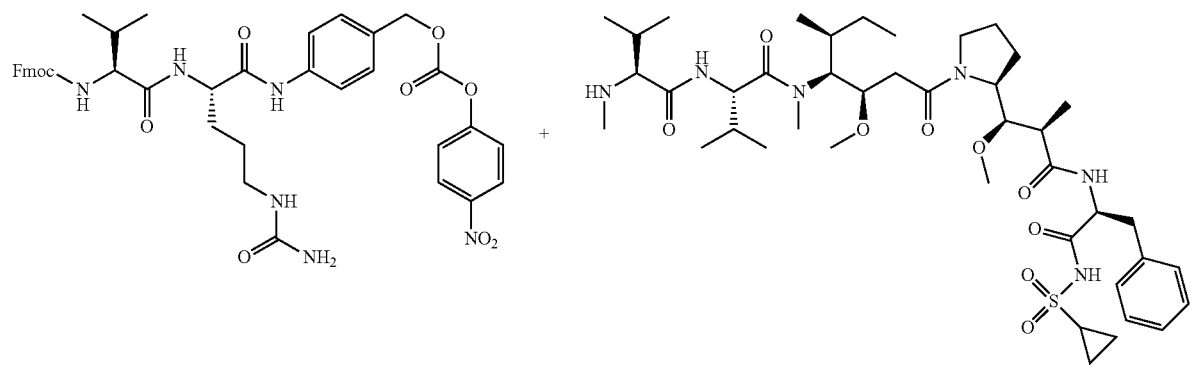

| HOBt, DIEA

| Piperidine, DMF

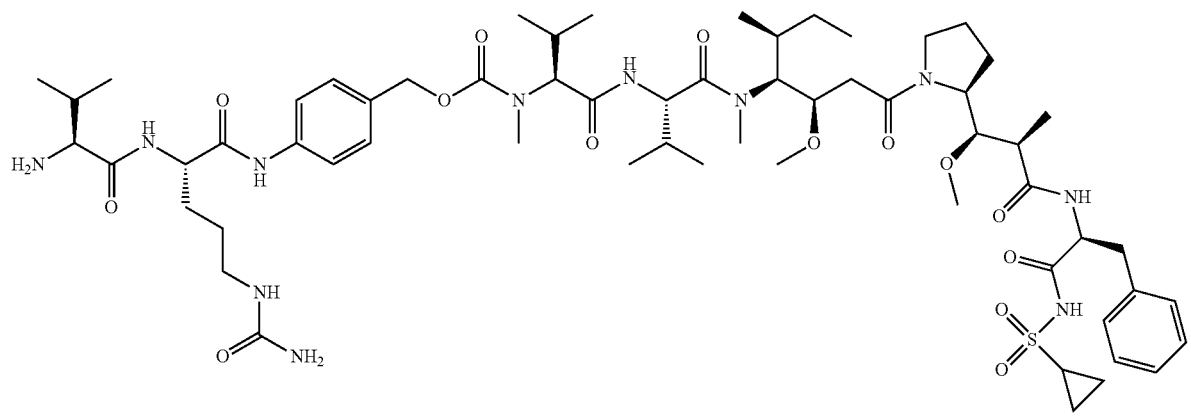

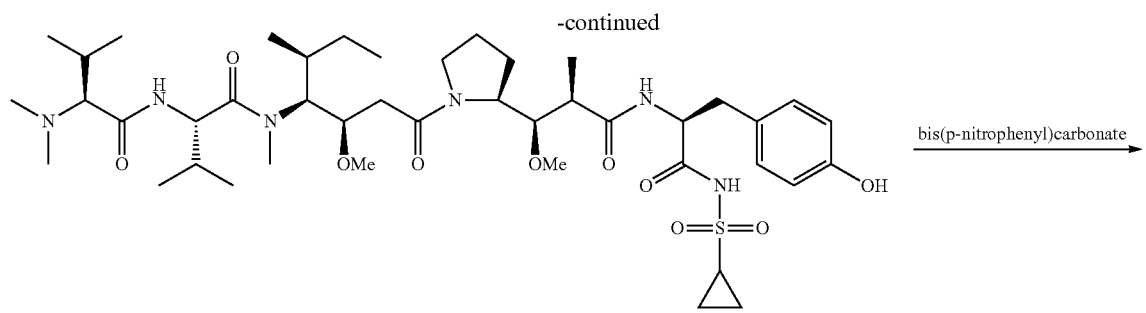
-continued
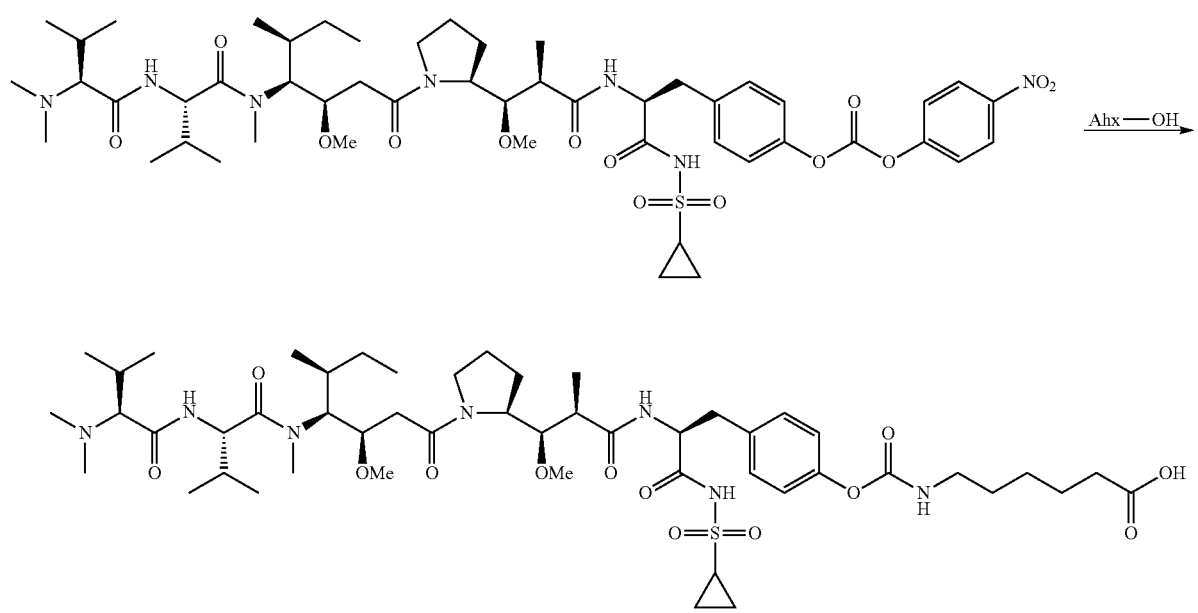
Method 1-2: Linker and Drug Connected Via Reductive Alkylation Reaction (General Procedure E)
GENERAL PROCEDURE SCHEME II
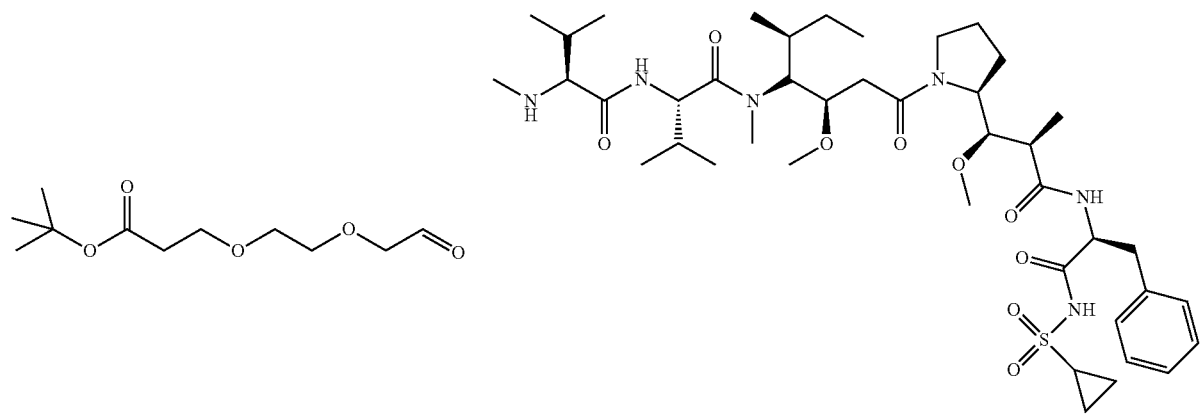
NaCNBH$_3$

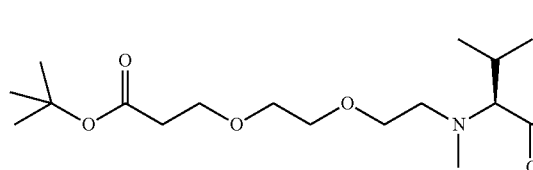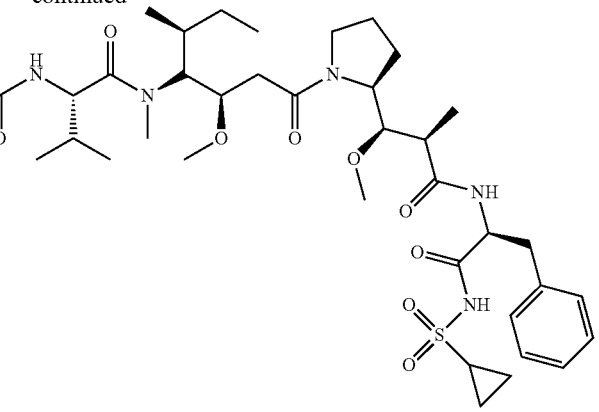
Method 1-3. Active Molecule Containing a Carboxylic Acid Moiety Connected to an Alkoxyamino Linker Via Formation of Hydoxamate (General Procedure A or B), Followed by Removal of Protective Groups.
GENERAL PROCEDURE SCHEME III
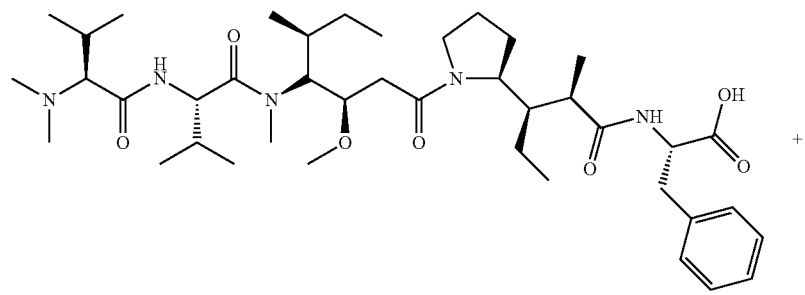
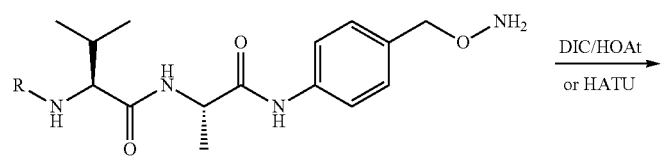
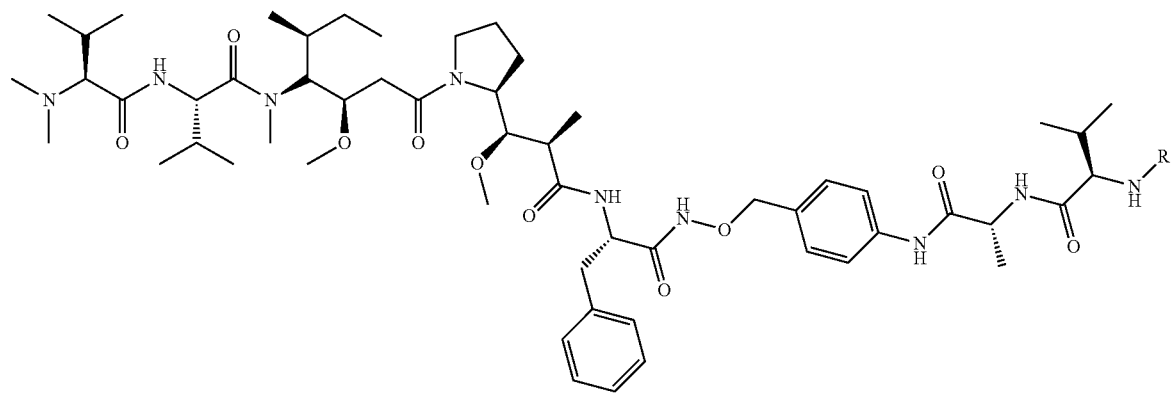

For active molecules that are hydoxamic acids, the above method still can be employed since the construct will release hydroxamic acid under enzymatic cleavage conditions. The reaction needs to start from its corresponding carboxylic acid.
GENERAL PROCEDURE SCHEME IV
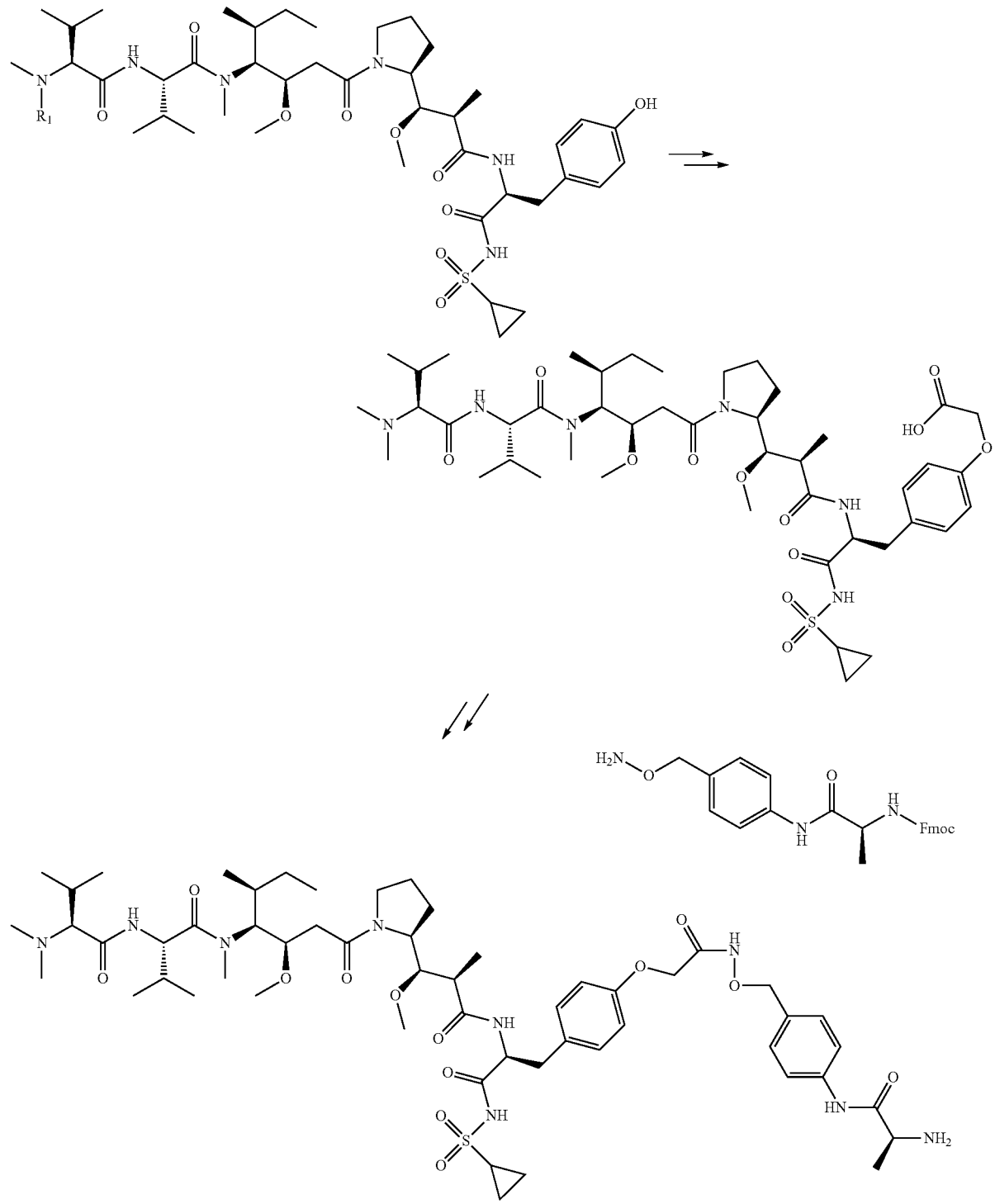

Step 2. Introducing Functional Groups to L1-(L2-D)
Method 2. Introduction of o-Phenylenediamine Moiety
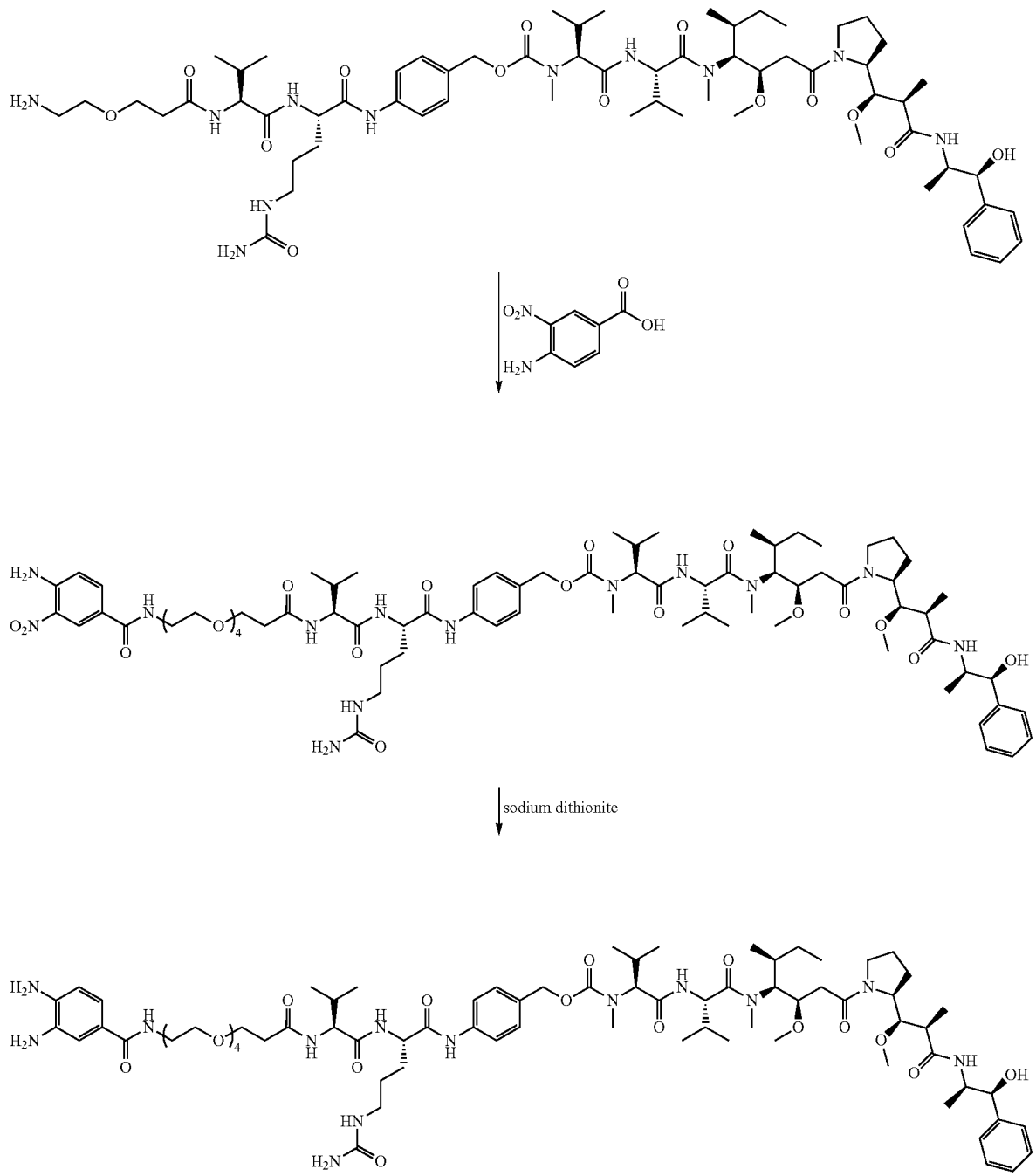
The 3-nitro-4-amino benzoic acid was incorporated using standard amidation reaction (General procedure B). The nitro group was reduced using sodium dithionite (3 eq) in acetonitrile/water to give the desired o-phenylene diamine. MS found: 1504.8 (M+H)$^+$.

Step 3. Introducing the Final Functional Groups Prior to Conjugation

Methods of Introduction of Final Reactive Group Prior to Conjugation Reaction, but not Limited to:

Method 3-1. Formation of Dibromomethyl Quinoxaline

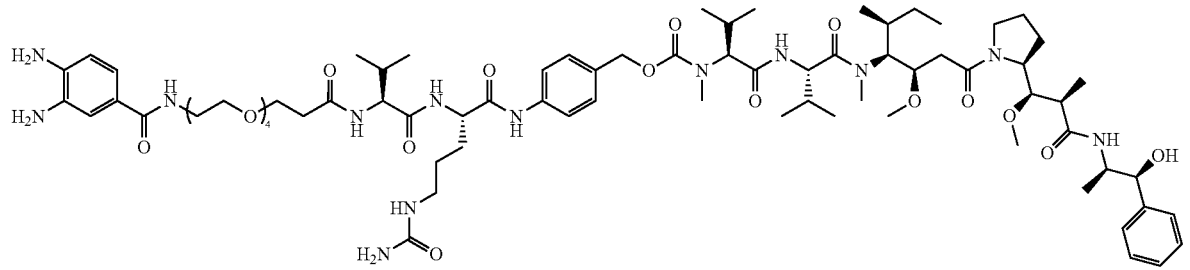

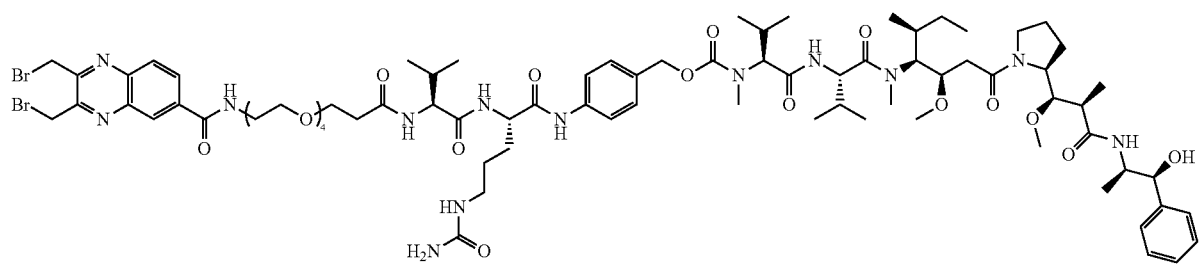

The o-phenylenediamine compound was dissolved in acetonitrile/water. Dibromomethyl diketone was added. The mixture was stirred at room temperature and purified directly by RP-HPLC to give the desired quinoxaline.

Method 3-2. Formation of Dichlorotriazine

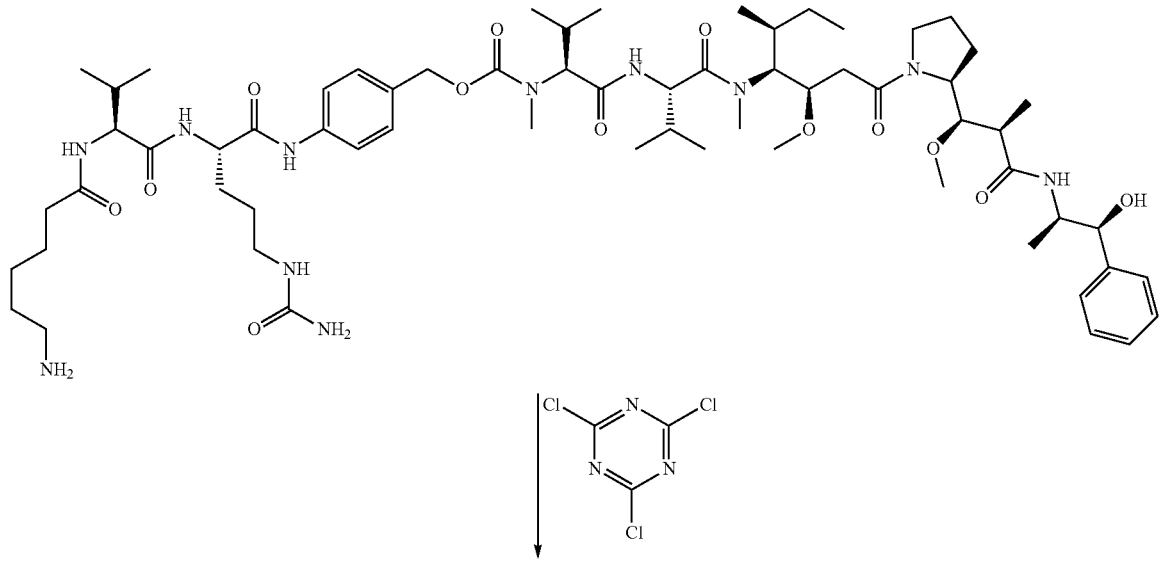

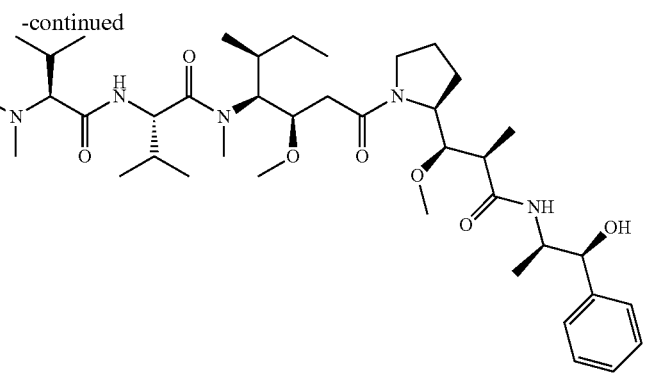

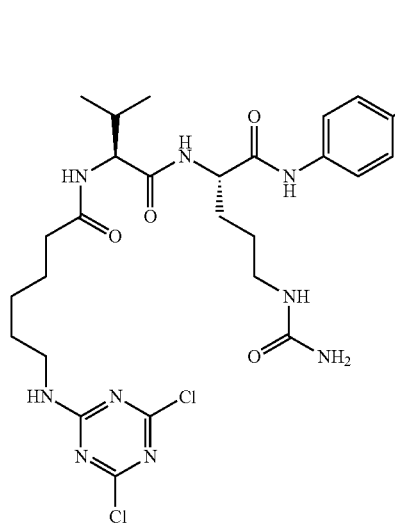

To a stirred and cooled (ice bath) solution of amine compound (12 mg) in DMF (1 mL) was added a solution of cyanuric chloride (10 mg) in THF (0.5 mL) and DIEA (5 μL). The reaction mixture was stirred at room temperature for 10 mins, and then concentrated under reduced pressure.

The residue was purified by RP-HPLC to give the desired dichlorotraizine (11 mg) as a white powder after lyophilization. MS found 1383.9 (M+H)$^+$.

Method 3-3. Formation of Dichloromethyltriazole

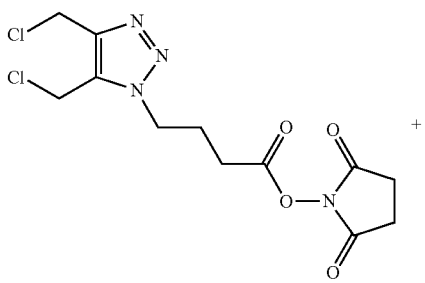

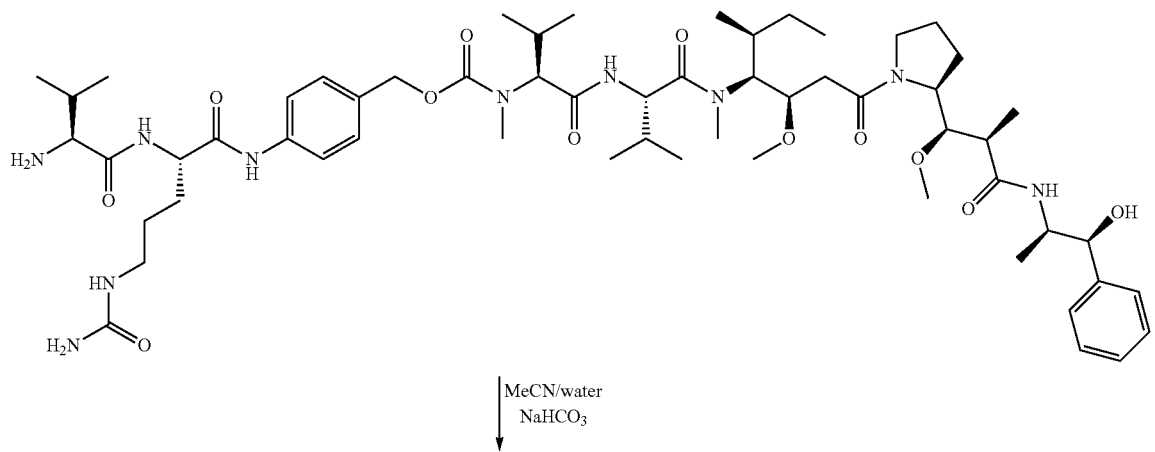

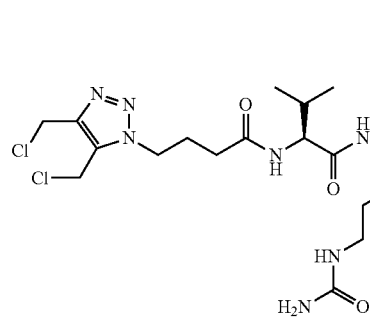
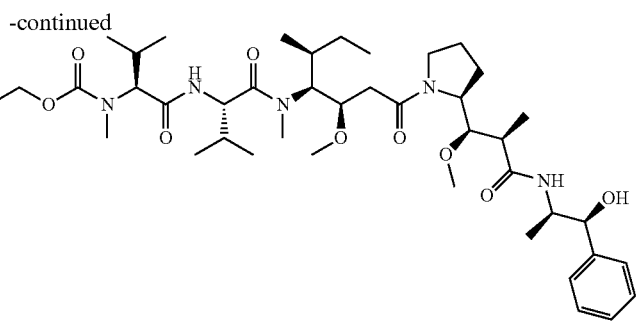
To a stirred solution of VC-PAB-MMAE (30 mg) in acetonitrile/water (2 mL, 6/4, v/v) was added a solution of trizole NHS ester (15 mg) in acetonitrile (0.5 mL) and sat. aq. NaHCO₃ (0.1 mL). The reaction mixture was purified by RP-HPLC to give the desired product as a white powder after lyophilization (28 mg). MS found: 1356.9 (M+H)⁺
Example I. Synthesis of Compound 10
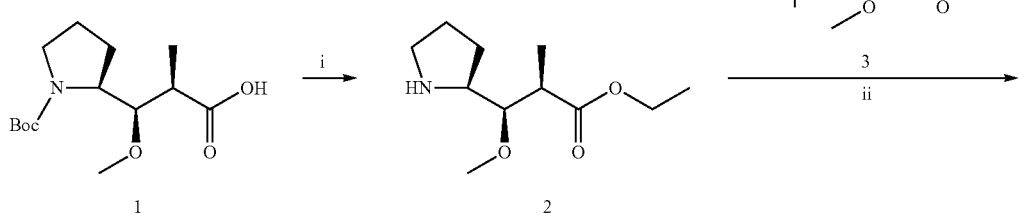
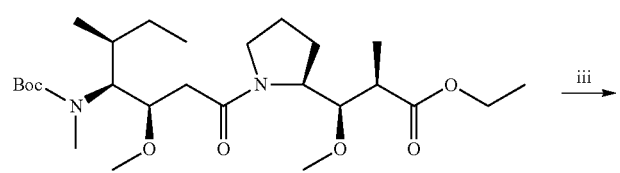
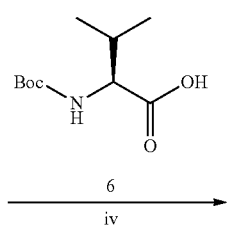
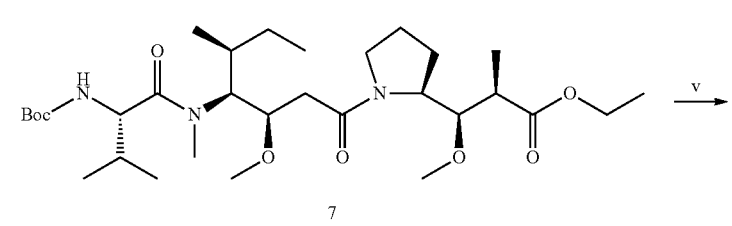

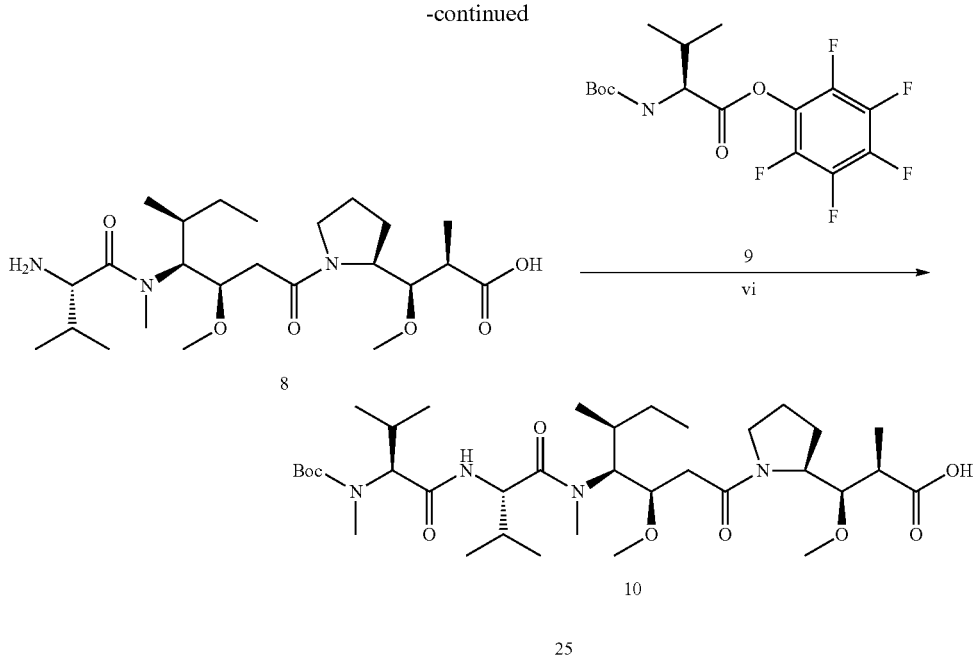

Scheme I.

Reagents and conditions: i. SOCl₂, EtOH; ii. DEPC, TEA, DCM; iii. TFA, DCM; iv. BrOP, DCM, DIEA; v. TFA, DCM; iv. DIEA, DCM, HOBt.

To a solution of compound 1 (23.4 g, 81.53 mmol) in dry EtOH (200 ml) was added SOCl₂ (100 mL) at 0° C. The mixture was stirred for overnight and the solvent was removed by evaporation in vacuo. The residue was immediately used for the next step without further purification. To a solution of compound 2 (81.53 mmol), compound 3 (50 g, 163.1 mmol) in dry DMF (150 mL) was added DEPC (15.9 g, 97.8 mmol), TEA (41 g, 0.408 mol) at 0° C. The mixture was stirred for 2 h at 0° C. Then the mixture was stirred overnight at room temperature. Solvent was removed by evaporation in vacuo. The residue was diluted with ethyl acetate-toluene (2:1, 900 ml) and washed with 1M KHSO₄, water, sat. NaHCO₃, and brine. The organic layer was dried and concentrated to give a residue, which was purified by column (hexanes:ethyl acetate:DCM=5:1:1) to give 38 g of compound 4.

To a solution of Boc-Val-OH (30.6 g, 0.142 mol), compound 5 (from 25 g of compound 4) in DCM (400 mL) was added BrOP (28 g, 70.87 mmol), DIEA (30 g, 0.236 mol) at 0° C. The mixture was shielded from light and stirred for 0.5 h at 0° C. Then the mixture was stirred for 48 h at room temperature. The solvent was removed by evaporation in vacuo. The residue was diluted with ethyl acetate-toluene (3:1, 900 mL) and washed with 1M KHSO₄, water, sat. NaHCO₃, and brine. The organic layer was dried and concentrated to give a residue, which was purified by silica gel column (hexanes:ethyl acetate:DCM=3:1:1) to give 22 g of compound 7.

To a solution of compound 7 (40 g, 66.7 mmol) in THF (600 mL) was added a mixture of LiOH (14 g, 0.33 mol) in water (300 mL) below 10° C. The mixture was stirred for 5 days at 25° C. THF was removed by evaporation. The aqueous layer was washed with Et₂O (200 mL×3). The aqueous layer was acidified to pH 2 with 1N HCl at 0° C., the mixture was extracted with ethyl acetate and the organic layer was washed with water and brine. The organic layer was dried and concentrated to give a residue, which was purified by Prep-HPLC to give 14 g of compound 8.

To a solution of compound 8 (3 g) in DCM (100 mL) was added compound 9 (3 g, prepared according to General procedure J from Boc-N-Me-Val-OH using EDC and pentafluorophenol). DIEA (2.6 mL) was added, followed by HOBt (cat. 100 mg) and the reaction mixture was stirred at room temperature for 16 h. The solvents were removed under reduced pressure and the residue was purified on a silica gel column to give compound 10 as a white powder (3.1 g). MS m/z Calcd for $C_{35}H_{64}N_4O_9$ 684.5. Found 707.6 ([M+Na]⁺).

Example II-1. Synthesis of Compound 13

SCHEME II-1

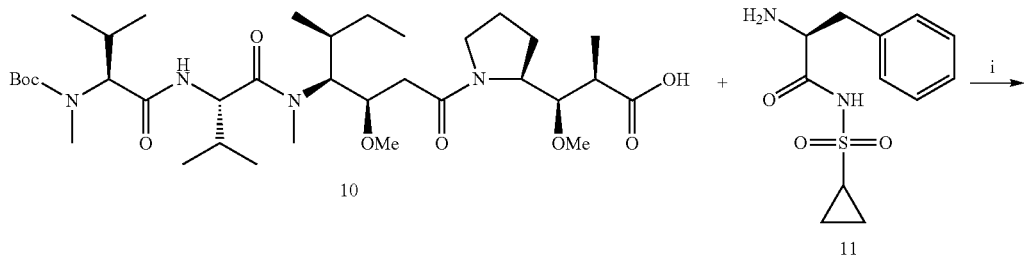

-continued

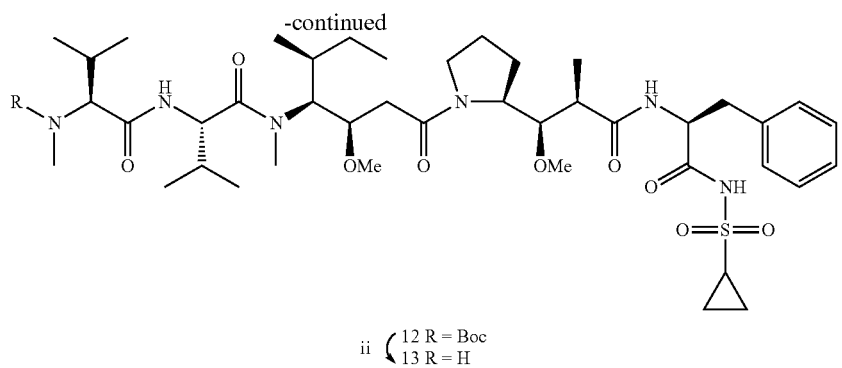

ii { 12 R = Boc
     13 R = H

Scheme II-1.

Reagents and conditions: i. DIC/HOAt, DMF, rt, 16 h; ii. HCl/Dioxane

The amino acid sulfonamide derivatives 11 were synthesized according to previously reported procedure (ARKIVOC 2004 (xii) 14-22, or WO 2007146695) using Boc protected amino acid and cyclopropyl/methyl sulfonamide, followed by removal of Boc (General procedure C)

Compound 13 was synthesized using the general procedures described above as following: DIC/HOAt mediated amide bond formation (General procedure B) between Boc-N-Me-Val-Val-Dil-Dap-OH (compound 1) and amine 11, followed by removal of Boc (General procedure C). The final compound was purified by reverse phase HPLC to give compound 13 as a white powder after lyophilization. MS m/z Calcd for $C_{42}H_{70}N_6O_9S$, 834.5. Found 835.6 ([M+H]$^+$).

Example II-2. Synthesis of Compounds 16

Scheme II-2.

Reagents and conditions: i. DIC/HOAt, DMF, rt, 16 h; ii. HCl/Dioxane

The amino acid sulfonamide derivatives 14 were synthesized according to previously reported procedure (ARKIVOC 2004 (xii) 14-22, or WO 2007146695) using Boc protected amino acid and cyclopropyl/methyl sulfonamide, followed by removal of Boc (General procedure C).

Compound 16 was synthesized using the general procedures described above as following: DIC/HOAt mediated amide bond formation (General procedure B) between Boc-N-Me-Val-Val-Dil-Dap-OH (compound 10) and amine 14, followed by removal of Boc (General procedure C). The final compound was purified by reverse phase HPLC to give compound 16 as a white powder after lyophilization. MS m/z Calcd for $C_{41}H_{70}N_6O_{10}S$, 838.5. Found 839.6 ([M+H]$^+$).

SCHEME II-2

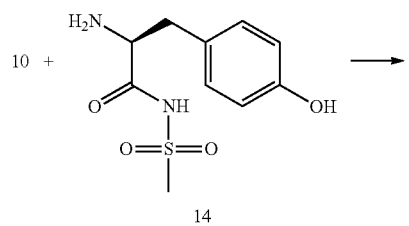

10 +

14

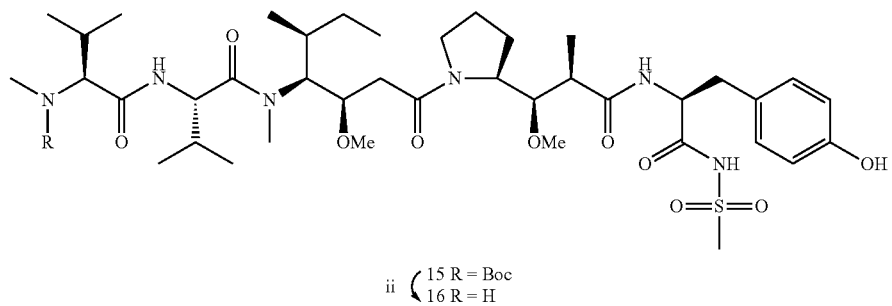

ii { 15 R = Boc
     16 R = H

Example II-3. Synthesis of Compound 20

SCHEME IIc

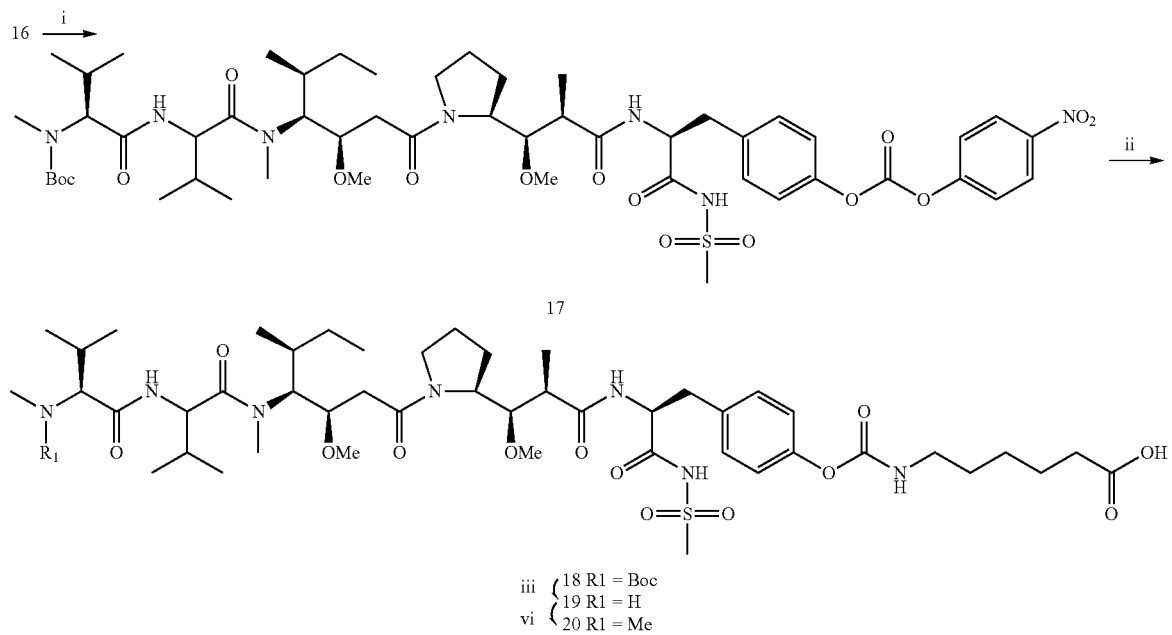

iii { 18 R1 = Boc
     19 R1 = H
vi { 20 R1 = Me

Scheme IIc.

Reagents and conditions: i. bis(nitrophenyl) carbonate, DIEA, THF/DMF, r.t.; ii. 6-aminohexanoic acid, NaHCO₃ (aq.); iii. HCl/Dixoane (4N); iv. HCHO, NaCNBH₃, DMF, HOAc.

The phenol 16 (1 mmol) was treated with 3 eq of bis(p-nitrophenyl)carbonate to form the activated carbonate 17 (general procedure G). The crude product was used directly without further purification. 6-Aminohexanoic acid (5 eq) was dissolved in sat. aq. NaHCO₃ (5 mL) and the solution was added. The reaction mixture was stirred at room temperature for 16 h. Citric acid (aq. 10%) was added to acidify the reaction (pH=4-5) and then diluted with EtOAc (150 mL). Organic layer was dried (over Na₂SO₄) and concentrated to give the crude product 18 which underwent the following procedures: removal of Boc (General procedure C), reductive alkylation using HCHO. The final product was purified by RP-HPLC to give compound 20 as a white powder after lyophilization. MS m/z Calcd for $C_{48}H_{81}N_7O_{13}S$, 995.6. Found 996.4 ([M+H]⁺).

Example III. Synthesis of Alkoxylamine Linkers 24, 25, 26, and 27

| ID | Structure |
|---|---|
| 24 | *Fmoc-Val-Ala-NH-C₆H₄-CH₂-O-NH₂* |
| 25 | *Fmoc-Val-Cit-NH-C₆H₄-CH₂-O-NH₂* |
| 26 | *Fmoc-Ala-NH-C₆H₄-CH₂-O-NH₂* |
| 27 | *Fmoc-NH-(CH₂)₅-C(O)-NH-C₆H₄-CH₂-O-NH₂* |

SCHEME III

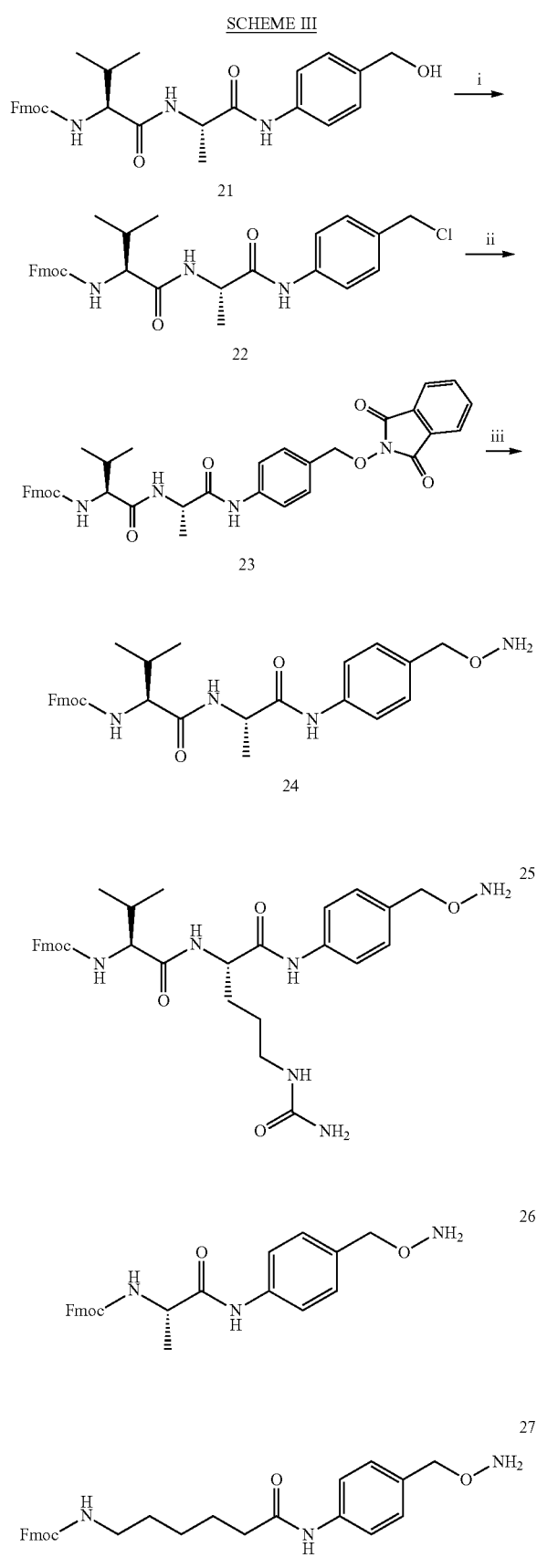

Scheme III.

Reagents and conditions: i. SOCl$_2$, THF, 1 h; ii. N-hydroxyphthalimide, NaHCO$_3$, DMF, rt, 48 h; iii. NH$_2$NH$_2$.H$_2$O, HOAc, DMF.

Example III-1. Synthesis of Compound 24

To a stirred solution of Fmoc-VA-PAB (21) (*Bioconjugate Chem.*, 2002, 13, 855-859) (9 g, 15 mmol) in THF (200 mL) was added thionyl chloride (18 mmol) dropwise. After the addition was complete, the reaction mixture was stirred at room temperature for 1 h. TLC analysis (ethyl acetate/hexane, 1/1, v/v) showed the completion of the reaction. The solvents were removed under reduced pressure and the residue was washed with hexanes (100 mL) to give compound 22 as a slightly yellowish solid (8.8 g).

Compound 22 (6.2 g, 10 mmol) was dissolved in anhydrous DMF (100 mL). N-Hydroxy-phthalimide (3.2 g, 20 mmol) was added, followed by solid NaHCO$_3$ (3.4 g, 40 mmol). The reaction mixture was stirred at room temperature for 48 h. TLC analysis showed that most of compound 61 was consumed. The reaction was then diluted with ethyl acetate (500 mL) and washed successively with sat. aq. NaHCO$_3$ (3×200 mL) and brine (200 mL). The organic layer was dried and concentrated to give compound 23 as a tan solid, which was used directly without further purification.

The crude compound 23 from previous step was dissolved in DMF (100 mL). HOAc (6 mL) was added, followed by hydrazine hydrate (5 mL). The reaction was stirred at room temperature for 1 h. LC/MS showed the completion of the reaction. The reaction mixture was then poured into a beaker containing 1 L of water under stirring. The precipitated solid was collected via filtration and washed twice with water to give compound 24 as a white solid (purity>85%, can be used directly). Pure compound 63 was obtained after RP-HPLC purification. MS m/z Calcd for C$_{30}$H$_{34}$N$_4$O$_5$ 530.3. Found 531.4 ([M+H]$^+$).

Example III-2. Synthesis of Compound 25

Compound 25 was synthesized starting from compound Fmoc-VC-PAB (*Bioconjugate Chem.*, 2002, 13, 855-859) using the procedures described above for the synthesis of compound 25. MS m/z Calcd for C$_{33}$H$_{40}$N$_6$O$_6$ 616.3. Found 617.5 ([M+H]$^+$).

Example III-3. Synthesis of Compound 26

Compound 26 was synthesized starting from compound Fmoc-A-PAB (synthesized according to the procedure reported: *Bioconjugate Chem.*, 2002, 13, 855-859) using the procedures described above for the synthesis of compound 26. MS m/z Calcd for C$_{25}$H$_{25}$N$_3$O$_4$ 431.2. Found 432.6 ([M+H]$^+$).

Example III-4. Synthesis of Compound 27

Compound 27 was synthesized starting from compound Fmoc-Ahx-PAB using the procedures described above for the synthesis of compound 27. MS m/z Calcd for C$_{28}$H$_{31}$N$_3$O$_4$ 473.2. Found 474.3 ([M+H]$^+$).

Example IV. Synthesis of -L1-(L2-D)
SCHEME IV
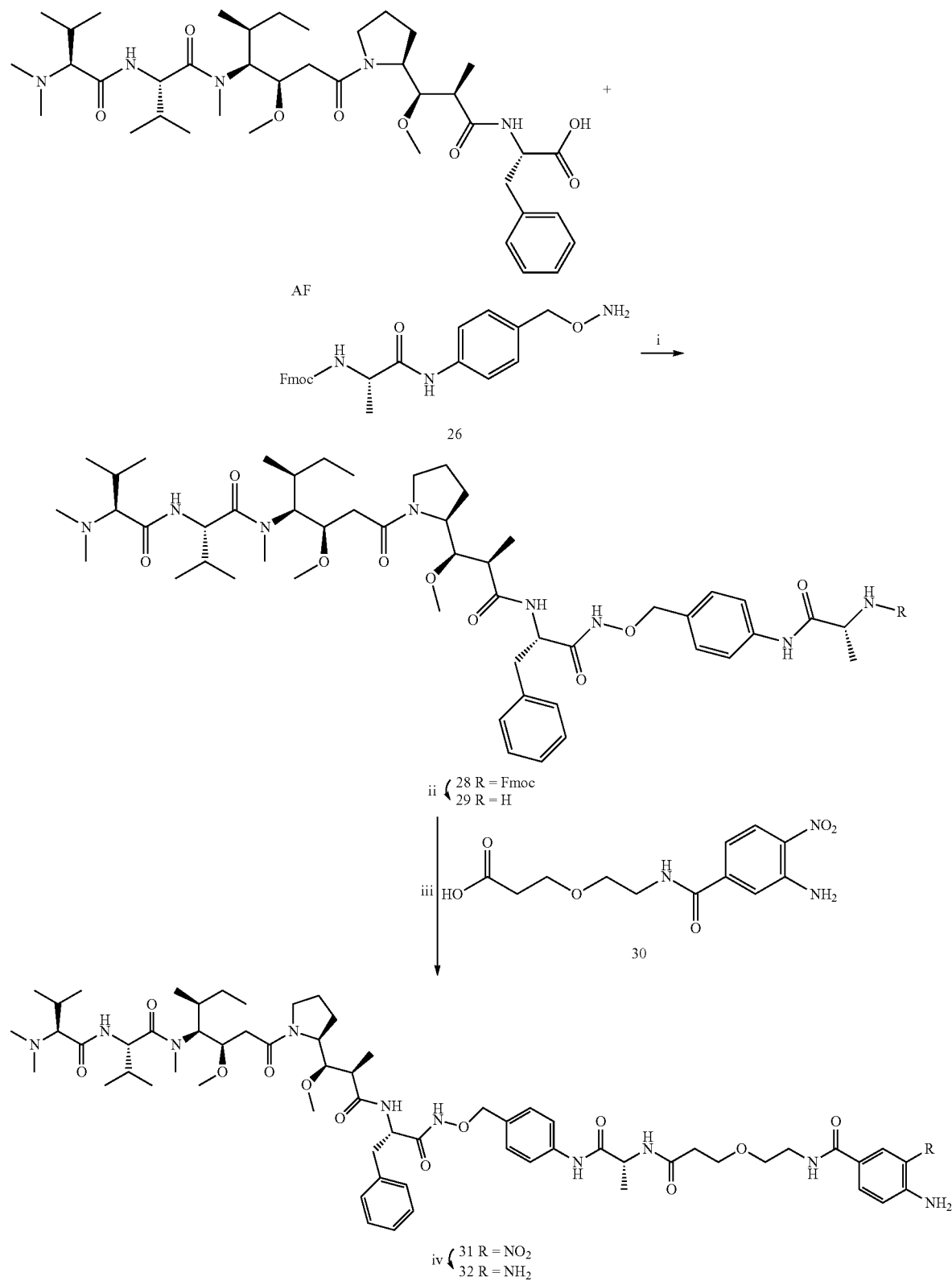

Scheme IV.

Reagents and conditions: i. DIC, HOAt, DMF, r.t.; ii. Piperidine, DMF; iii. HATU, DIEA, DMF; iv. Na$_2$S$_2$O$_4$, MeCN, H$_2$O, pH=6.

Example IV-1. Synthesis of Compound 32

Compound 32 was synthesized using the general procedures described above as following: DIC/HOAt mediated amide bond formation (General procedure B) between Auristatin F and compound 26, followed by removal of Fmoc (General procedure D), reaction with acid 30 (General procedure A), and reduction of the nitro group to amino group.

The nitro compound 31 (32 mg) was dissolved in acetonitrile/water (6/4, v/v) and a solution of sodium dithionite (1M in water, 0.2 mL) was added. The pH of the reaction was controlled at 6-6.5 by addition of MES buffer. The mixture was stirred at room temperature for 2 h and purified directly by RP-HPLC to give the desired product as a white solid after lyophilization (18 mg). MS found 1319.0 (M+H)$^+$.

Example V. Introduction of the Final Functional Group Prior to Conjugation Reaction

| ID | Structure of —L$^1$—(L$^2$—D) | MS |
|---|---|---|
| 34 | | 1713.0 |
| 40 | | 1526.4 |

-continued
| ID | Structure of —L¹—(L²—D) | MS |
|---|---|---|
| 36 | 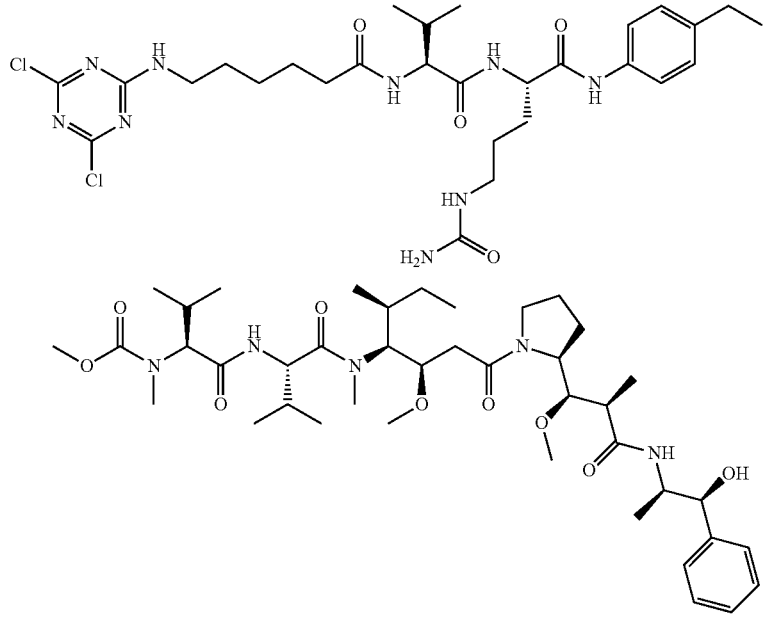 | 1383.9 |
| 39 | 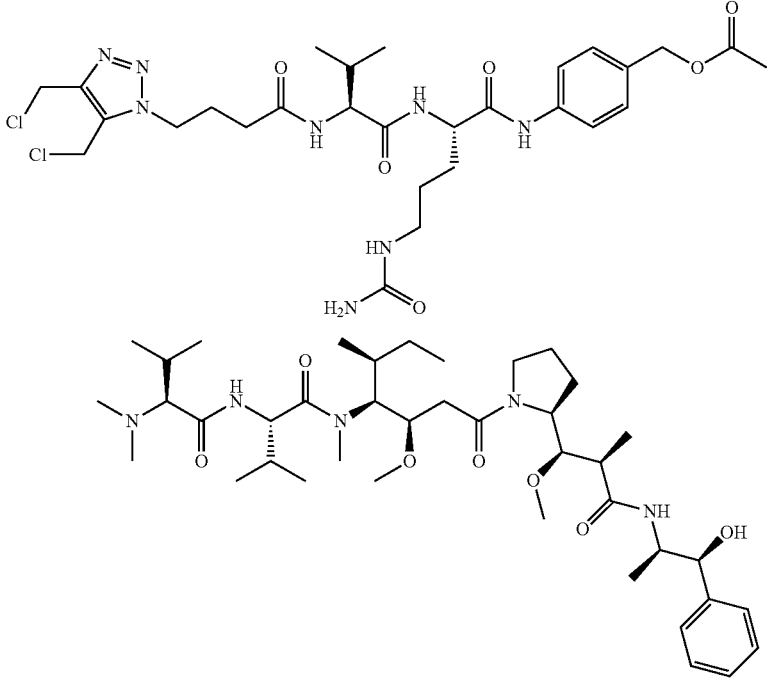 | 1356.9 |
| 41 | 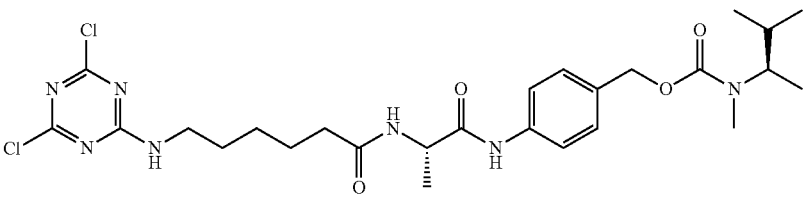 | 1281.2 |

| ID | Structure of —L¹—(L²—D) | MS |
|---|---|---|
| | 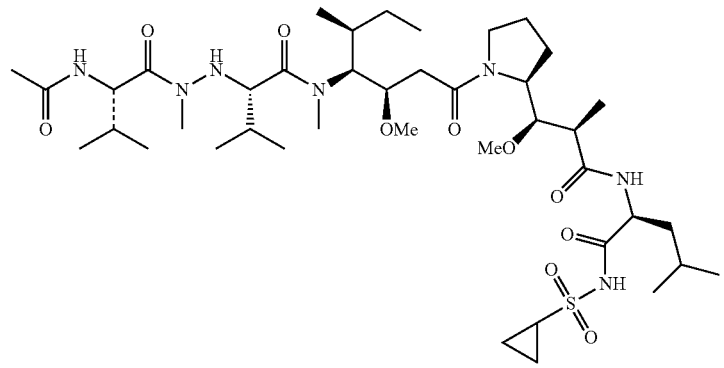 | |
| 42 | 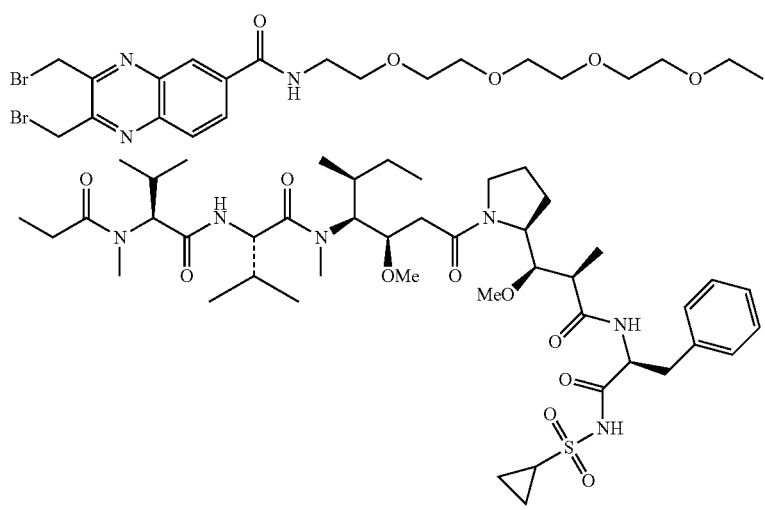 | 1424.5 |
| 43 | 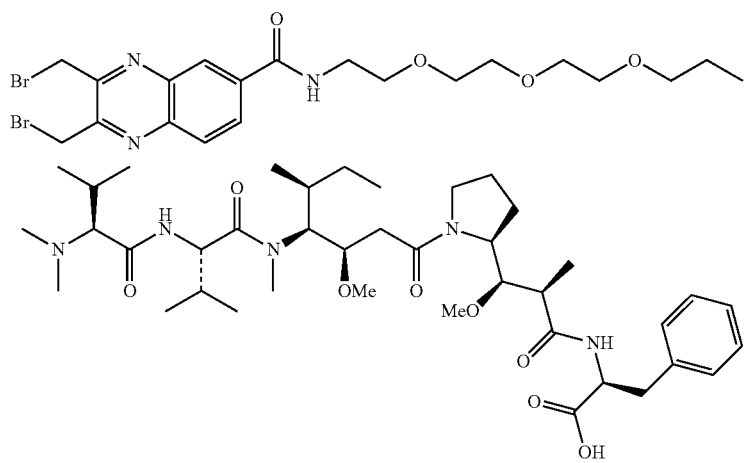 | 1249.5 |
| 44 | 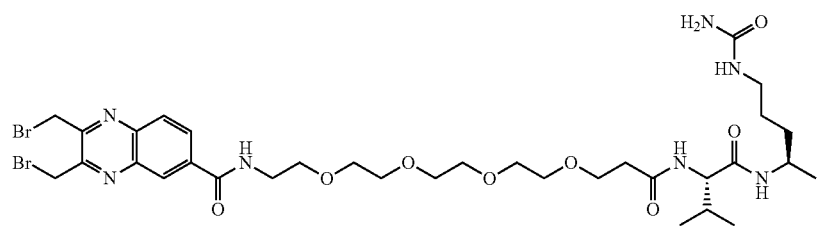 | 1621.7 |

| ID | Structure of —L¹—(L²—D) | MS |
|---|---|---|
| | 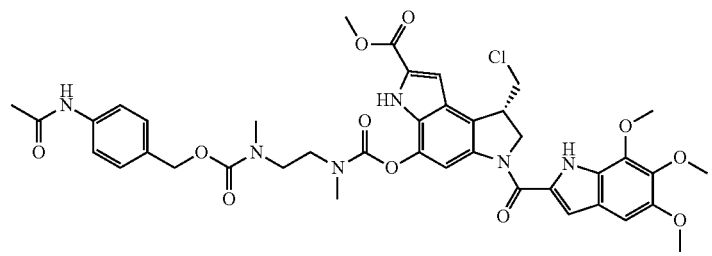 | |
| 45 | 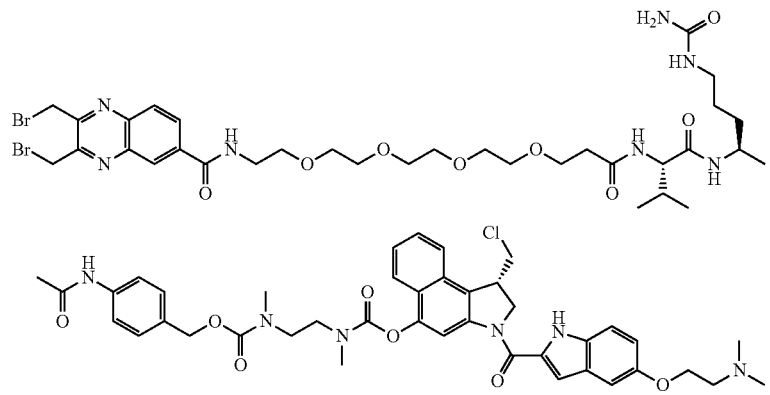 | 1572.7 |
| 46 | 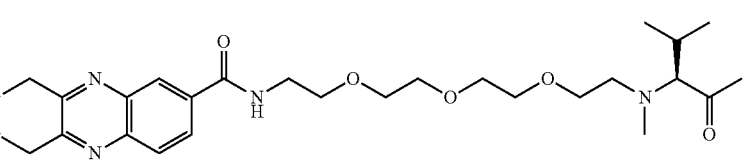 | 1288.3 |
| | 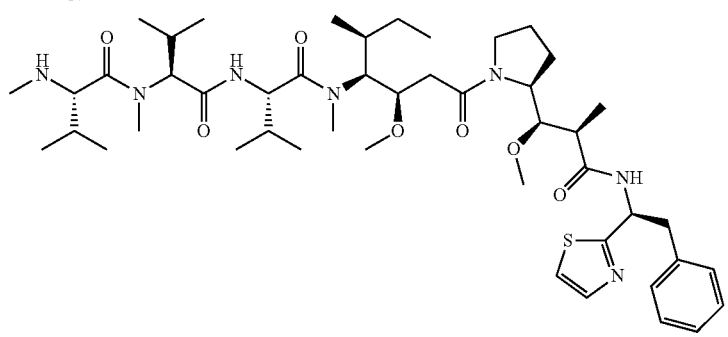 | |
| 47 | 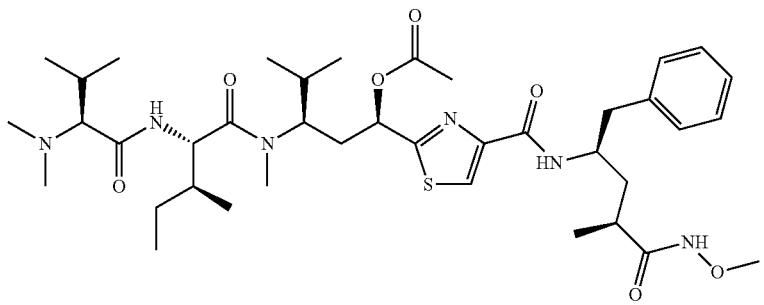 | 1510.8 |

| ID | Structure of —L¹—(L²—D) | MS |
|---|---|---|
| | 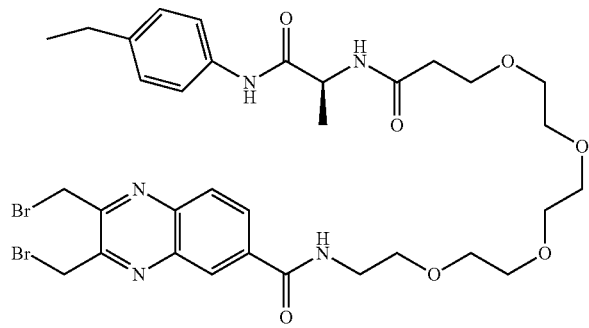 | |
| 48 | 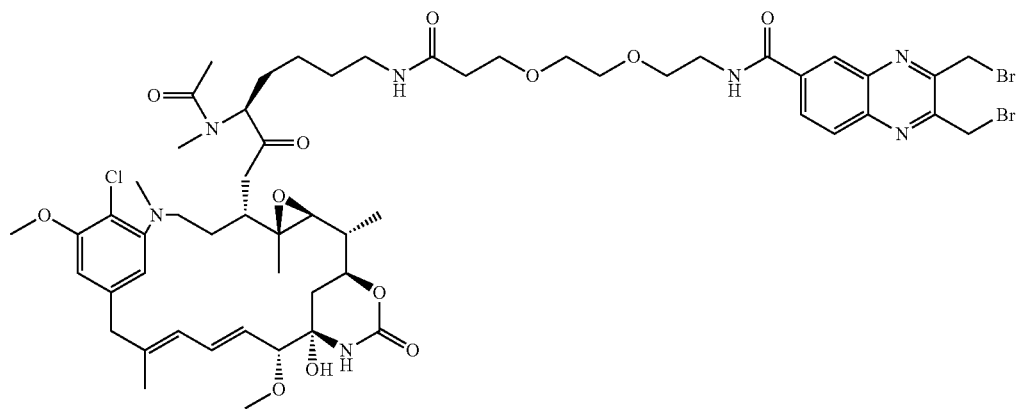 [SMILES: COc1cc2cc(c1Cl)N(C)CC[C@H](CC(=O)[C@H](CCCCNC(=O)CCOCCOCCNC(=O)c1ccc3nc(CBr)c(CBr)nc3c1)N(C)C(C)=O)[C@]1(C)O[C@H]1[C@H](C)[C@@H]1C[C@@](O)(NC(=O)O1)[C@H](OC)/C=C/C=C(\C)C2] | 1250.6 |
| 49 | 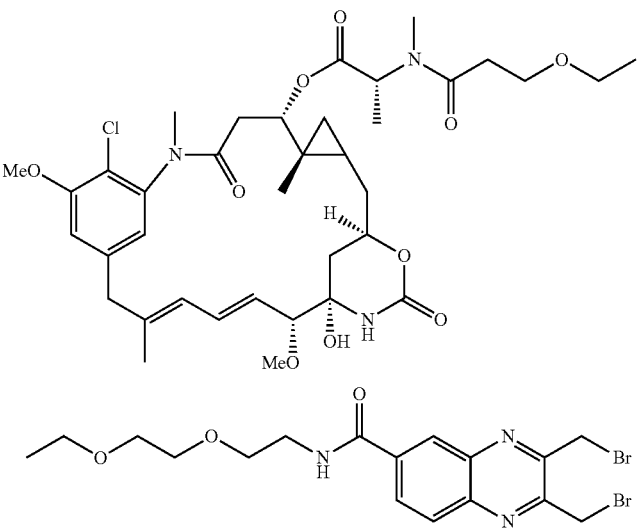 | 1195.4 |

| ID | Structure of —L¹—(L²—D) | MS |
|---|---|---|
| 50 | 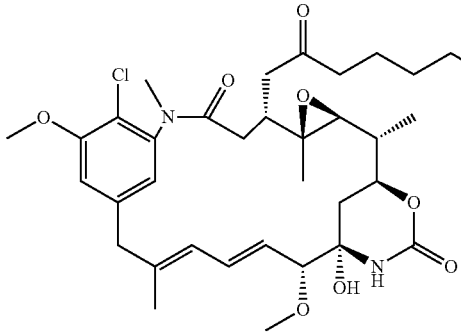 | 1020.4 |
Example V-1. Formation of Dibromomethyl Quinoxaline

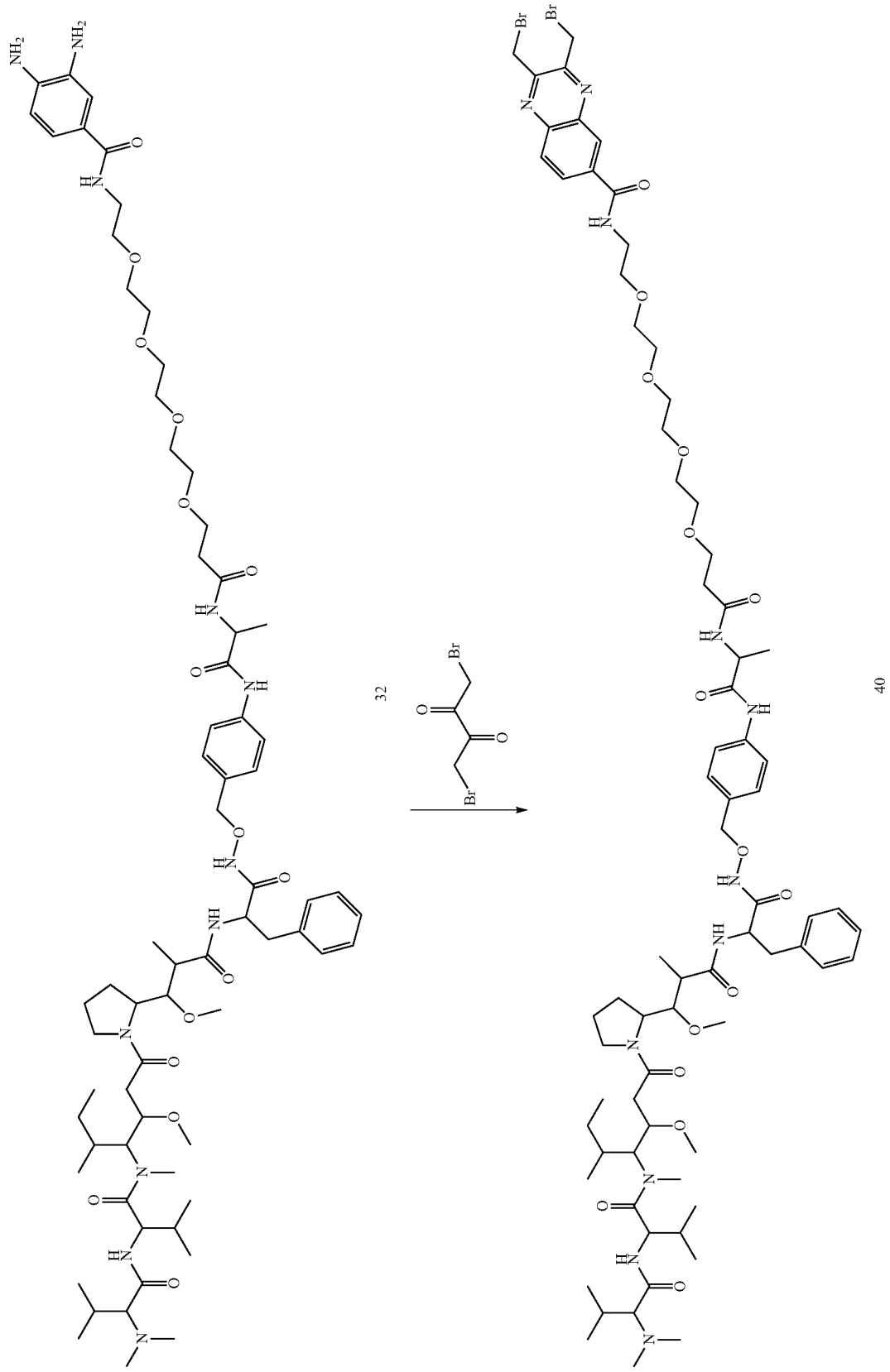

The o-phenylenediamine compound 32 (12 mg) was dissolved in acetonitrile/water (1 mL). Dibromomethyl diketone (10 mg) was added. The mixture was stirred at room temperature and purified directly by RP-HPLC to give the desired quinoxaline 40 as a white powder (12 mg) after lyophilization. MS found 1526.4 (M+H)$^+$.

Compound 34, 42, 43, 44, 45, 46, and 47 were synthesized from the corresponding o-phenylenediamines using the synthetic procedure described above for the synthesis of compound 40.

Example V-2. Formation of Dichlorotriazine

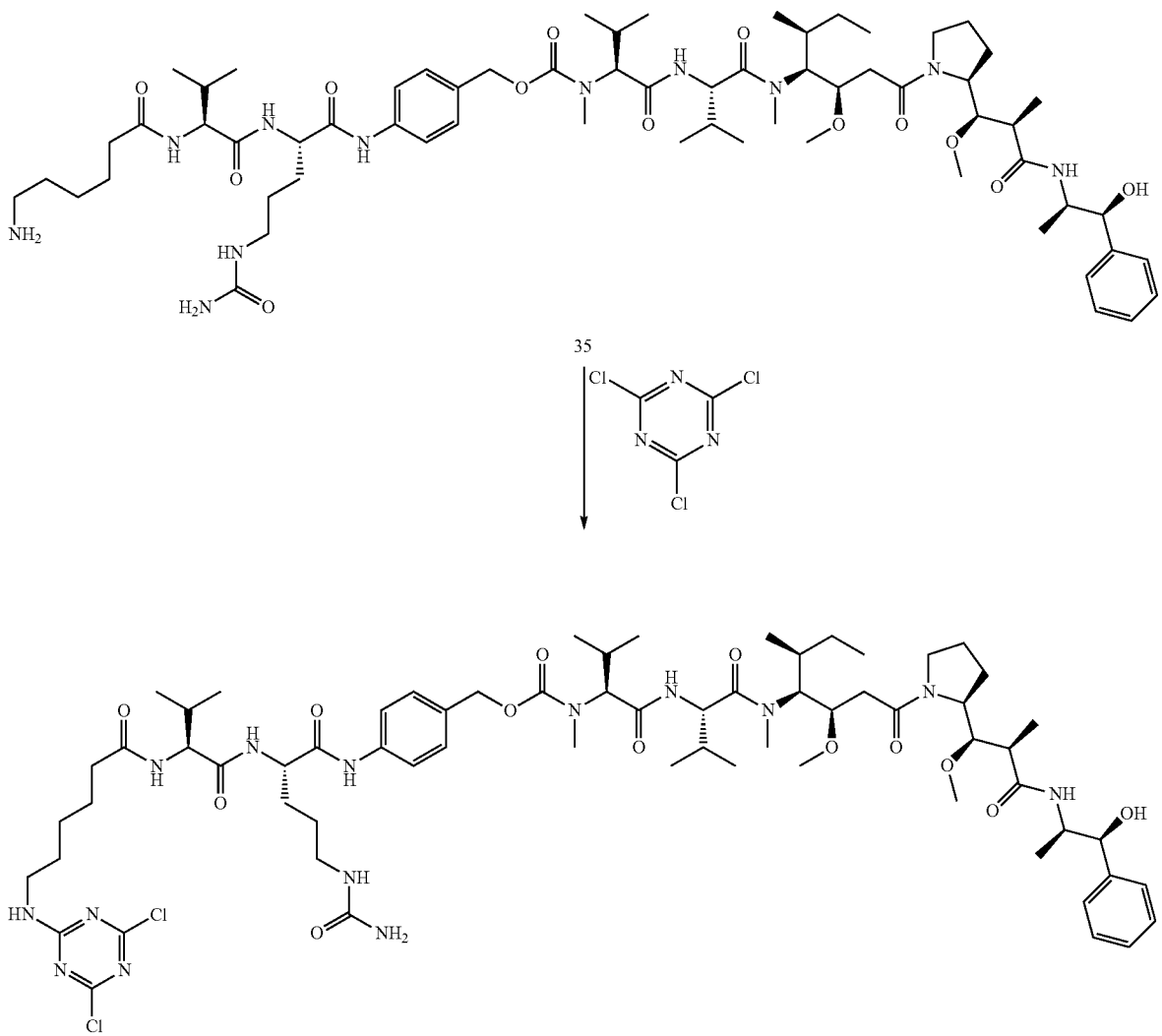

To a stirred and cooled solution of amine compound 35 (12 mg) in DMF (1 mL) was added a solution of cyanuric chloride (10 mg) in THF (0.5 mL) and DIEA (5 μL). The reaction mixture was stirred at room temperature for 10 mins, and then concentrated under reduced pressure. The residue was purified by RP-HPLC to give the desired dichlorotraizine 36 (11 mg) as a white powder after lyophilization. MS found 1383.9 (M+H)$^+$.

Compound 41 was synthesized using the same procedure described above for the synthesis of compound 36. MS found 1281.2 (M+H)$^+$.

Example V-3. Formation of Dichloromethyltriazole
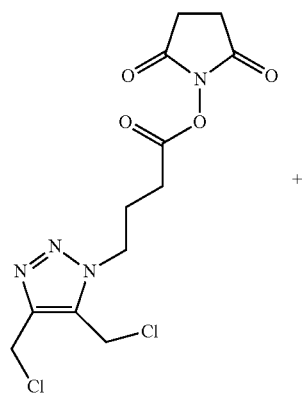
37
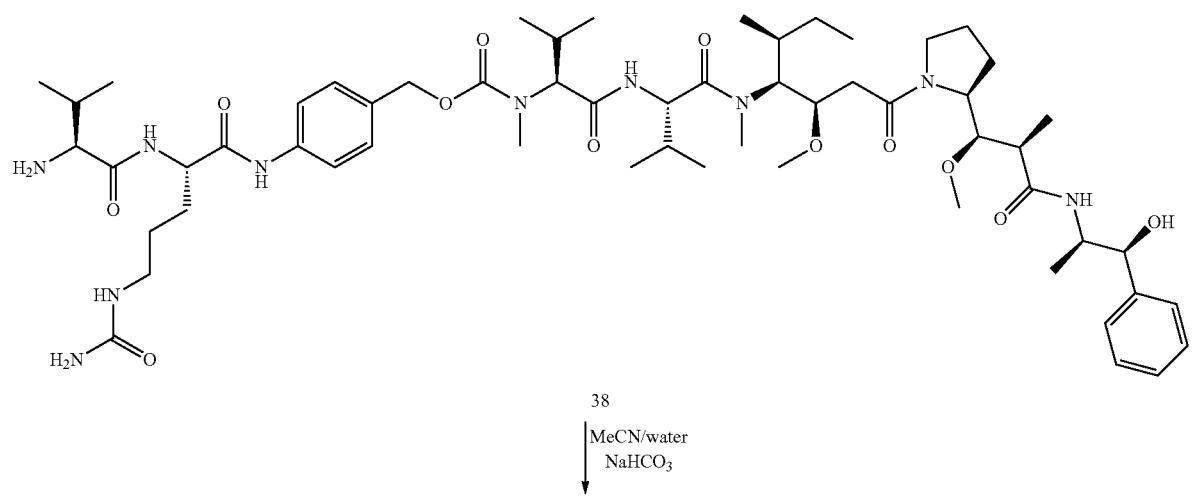
38
MeCN/water
NaHCO₃
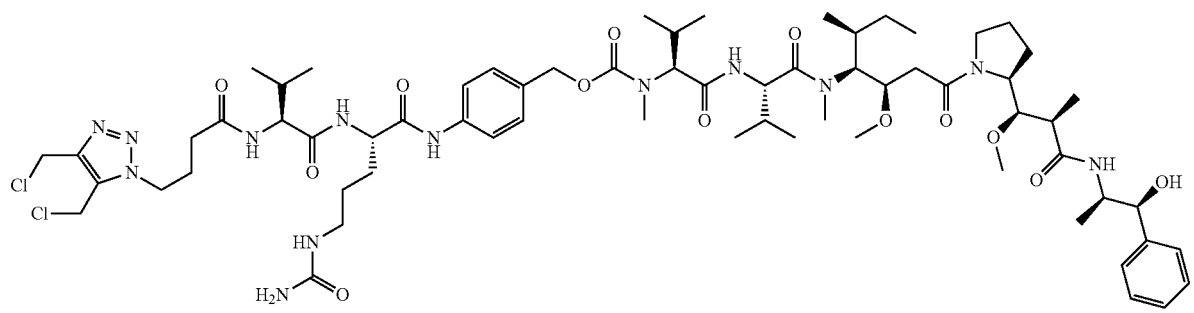
39

To a stirred solution of VC-PAB-MMAE (38, 30 mg) in acetonitrile/water (2 mL, 6/4, v/v) was added a solution of trizole NHS ester (37, 15 mg) in acetonitrile (0.5 mL) and sat. aq. NaHCO$_3$ (0.1 mL). The reaction mixture was purified by RP-HPLC to give the desired product 39 as a white powder after lyophilization (28 mg). MS found: 1356.9 (M+H)$^+$.

Example V-4. Synthesis of Compound 50

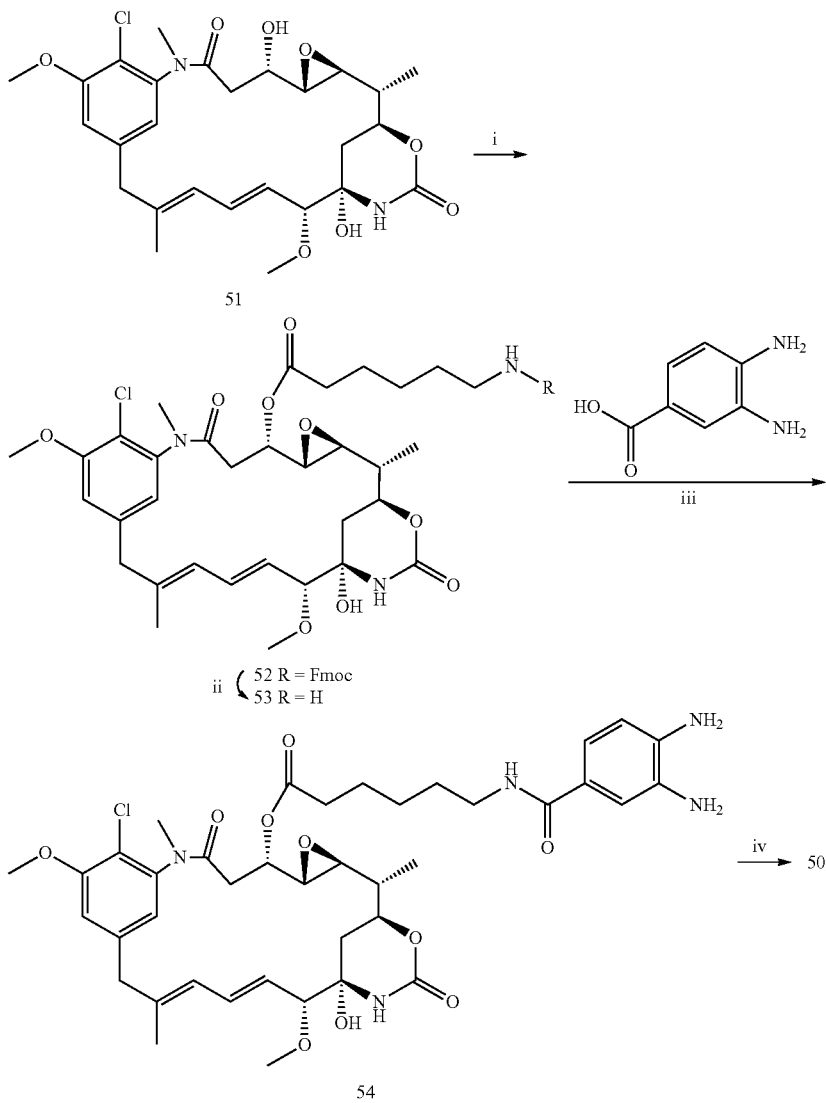

Scheme V-4.

Reagents and conditions: i. Fmoc-Ahx-OH (aminohexanoic acid), DIC, DCM, Py, rt, 48 h; ii. Piperidine, DMF; iii. DIC, HOBt; iv. Dibromomethyl diketone.

Fmoc-Ahx-OH (353 mg) was suspended in anhydrous DCM (5 mL) and DIC (0.5 mmol) was added. The mixture was stirred at room temperature for 1 h. Maytansinol (compound 51, 56 mg) was added to the mixture, followed by addition of 0.5 mL of pyridine. The reaction mixture was stirred at room temperature for 48 h. Solvents were removed under reduced pressure and the residue was purified by column chromatography (silica gel, EA/hexanes) to give compound 52 as a white solid (45 mg) which was treated with piperidine to remove Fmoc (General procedure D), followed by amidation reaction with 3,4-diaminobenzoic acid (1 eq) using DIC/HOBt (General procedure B, using HOBt instead of HOAt) to give compound 54 (22 mg) as a slightly yellowish powder after HPLC purification and lyophilization. Compound 54 was then converted to the desired compound 50 using the same procedure described above for the synthesis of compound 40. MS found 1020.4 (M+H)$^+$.

Antibody-Drug Conjugation

General Conjugation Procedure

To a target antibody, 0.5-50 mgs/mL, in a certain buffet at pH 5.0-9.0, such as PBS, was added 0.5-100 eq of reducing agent such as TCEP and DTT. The reduction was performed at 0-40° C. for 0.5-40 hours with gentle stirring or shaking, and then the reducing agent was removed by column or ultrafiltration. To the partially reduced antibody, 0.5-50 mgs/mL, in a certain buffet at pH 5.0-9.0, such as PBS, with 0-30% of organic co-solvent such as DMA, was added 0.5-10 eq of the activated drug-linker bearing a dibromo or dichloro-functionality. The reaction was conducted at 0-40°

C. for 0.5-40 hours with gentle stirring or shaking, monitored by HIC-HPLC. The resultant crude ADC product underwent necessary down-stream steps of desalt, buffet changes/formulation, and optionally, purification, using the state-of-art procedures. The final ADC product was characterized by HIC-HPLC, SEC, RP-HPLC, and optionally LC-MS. The average DAR was calculated by UV absorption and/or MS spectroscopy.

Trastuzumab and compound 34 were combined in various drug/antibody ratios under as described in the General Conjugation Procedure. Trastuzumab was incubated with 10 mM TCEP stock solution at 37° C. for 0.5 to 40 hours. After reduction, the excess of TCEP was removed by a gel filtration column. The reduced trastuzumab was then mixed with compound 34 in drug/antibody ratio range from 1 to 10 at 0 to 40° C. After overnight reaction, excess compound 34 was removed from Trastuzumab-c-34 conjugate by a gel filtration column. Purified Trastuzumab-c-34 conjugates stored at 4 to −20° C. and to be used for in vitro and in vivo tests.

The product of the conjugation reaction was analyzed using HIC-HPLC under conditions: HPLC Column: Tosoh TSKgel Butyl-NPR, 4.6 mm×3.5 cm, 2.5 mm; Buffer A: 20 mM sodium phosphate, 1.5 M Ammonium Sulfate, pH 7.0; Buffer B: 20 mM sodium phosphate, 25% v/v isopronal, pH 7.0; flow rate: 1 mL/min; Gradient: 10 min 10% Buffer B to 80% Buffer B, 4 min 100% Buffer B; 20 μL sample.

Figure 2:
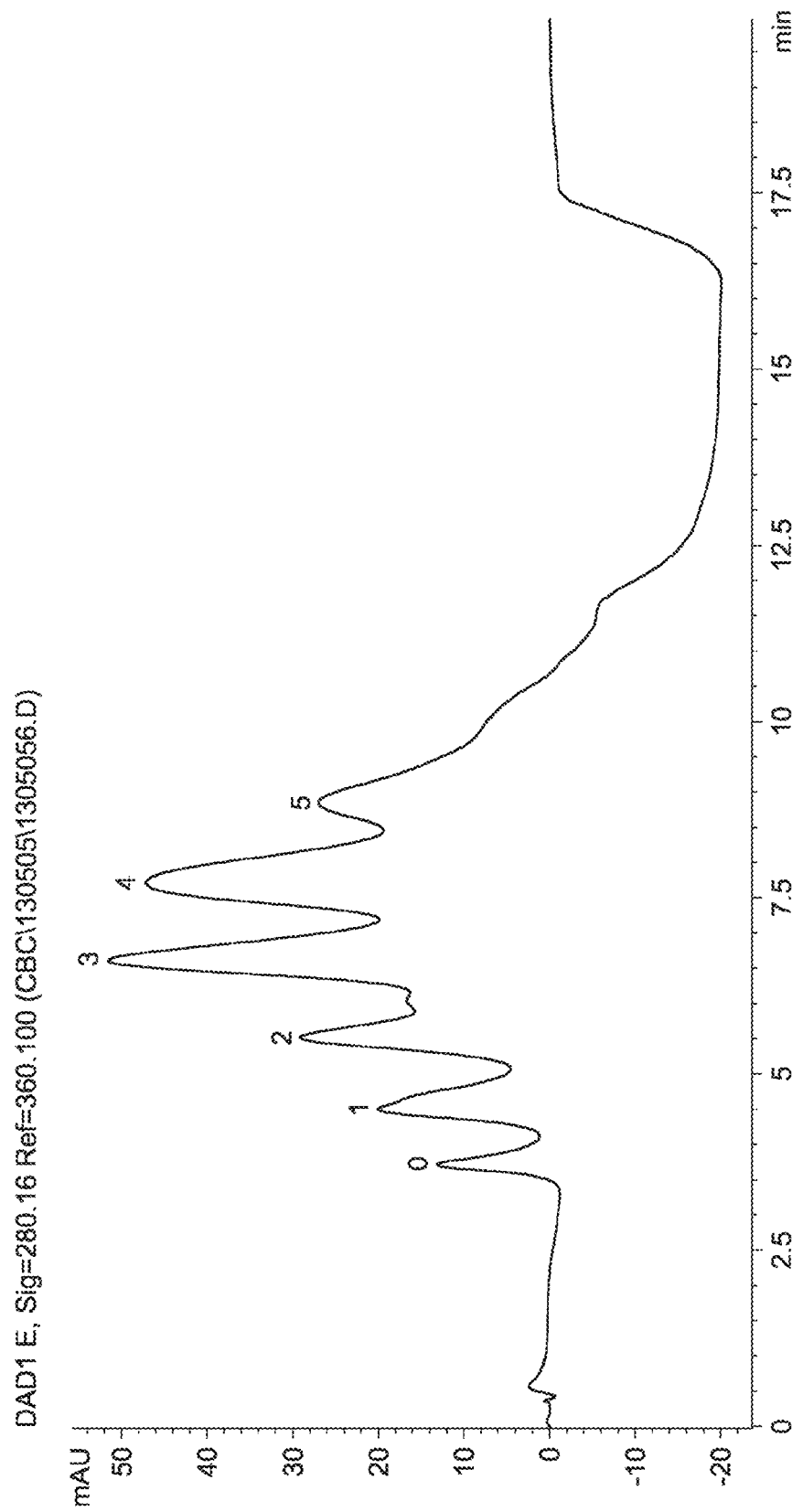
FIG. 2 shows the HIC-HPLC chromatogram product of reacting drug and antibody at a drug/antibody ratio of 6:1.
Figure 3:
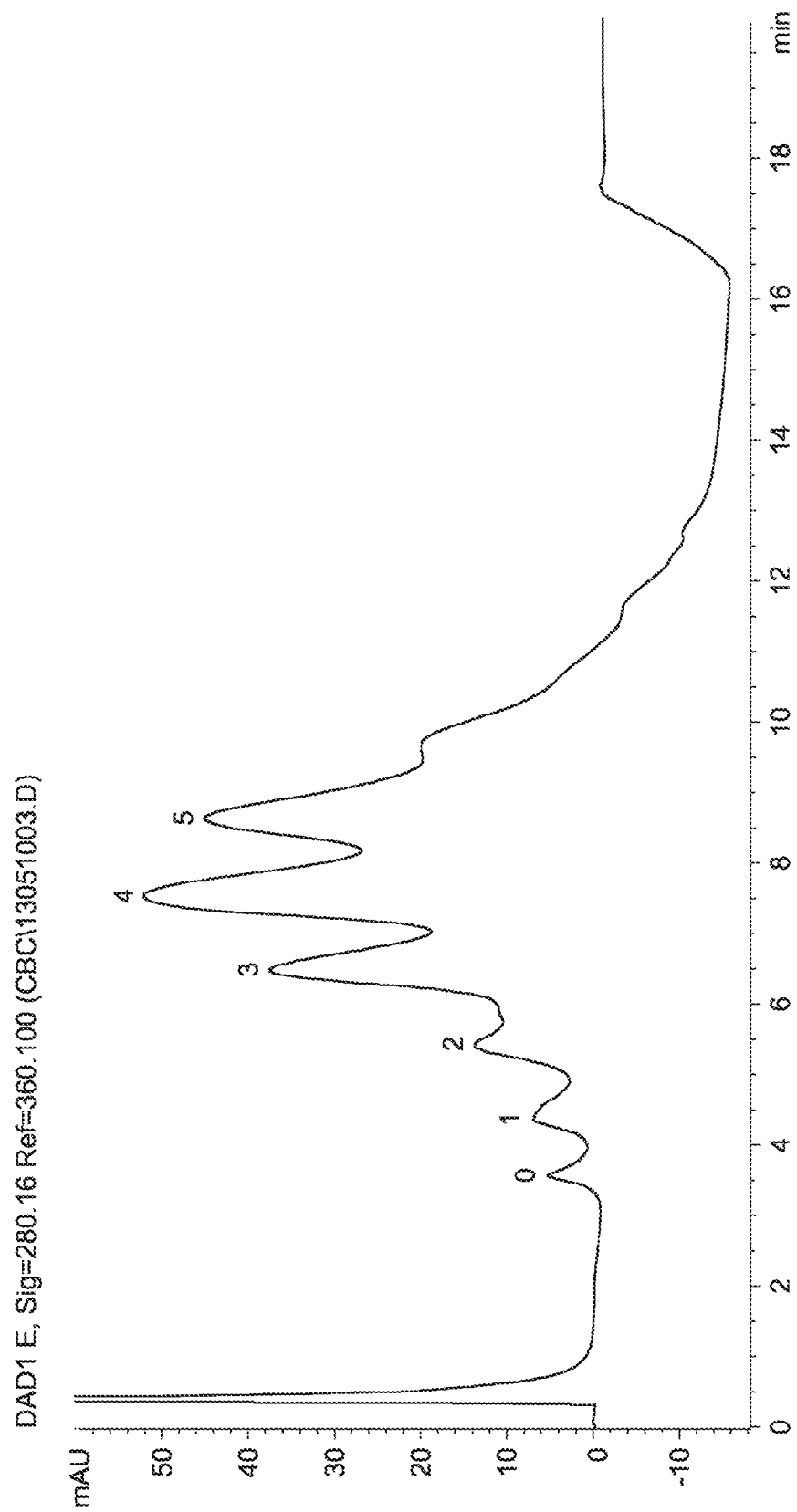
FIG. 3 shows the HIC-HPLC chromatogram product of reacting drug and antibody at a drug/antibody ratio of 1:6.5.
Figure 4:
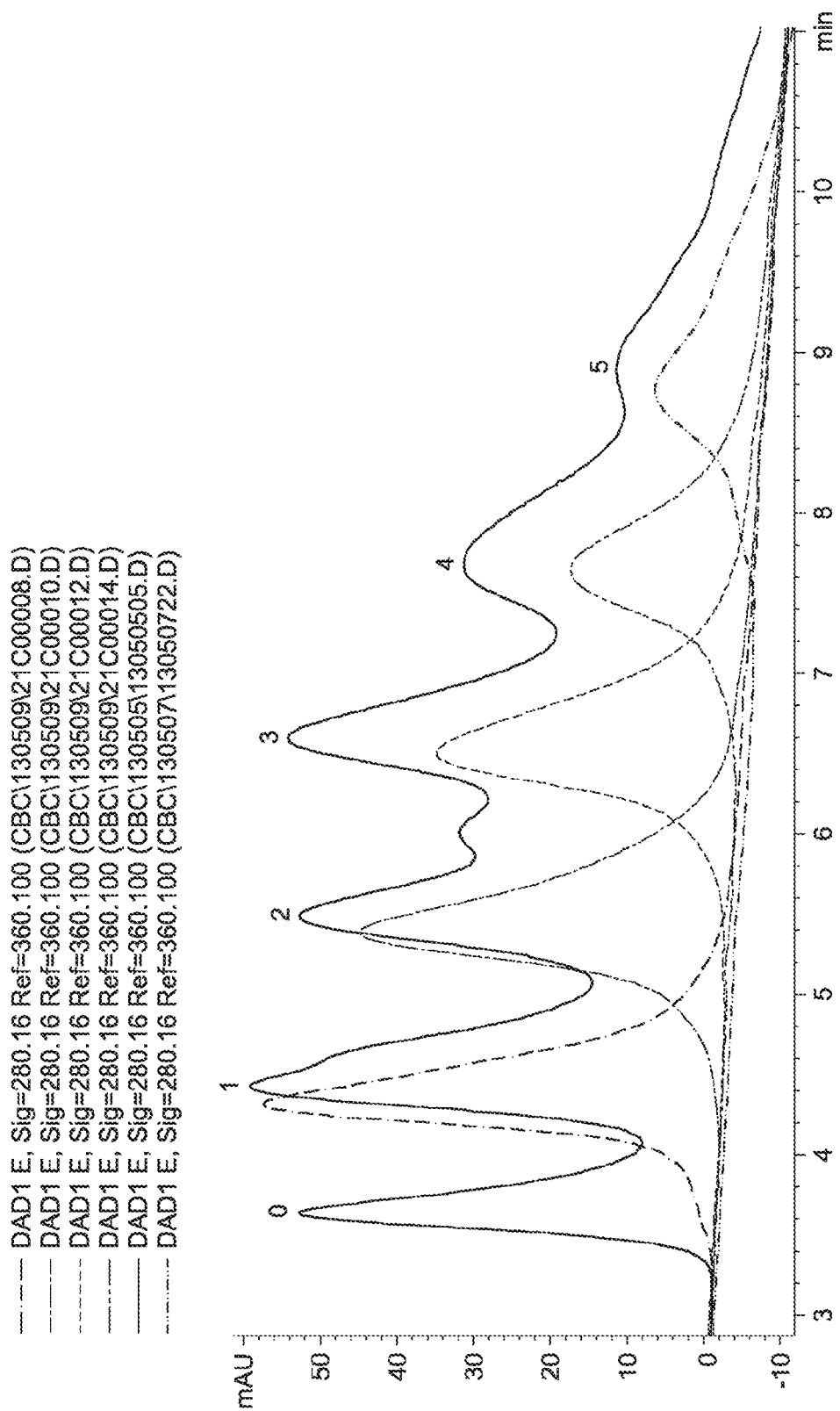
FIG. 4 shows the HIC-HPLC chromatogram product of reacting drug and antibody at a drug/antibody ratio of 1:4.
Figure 5:
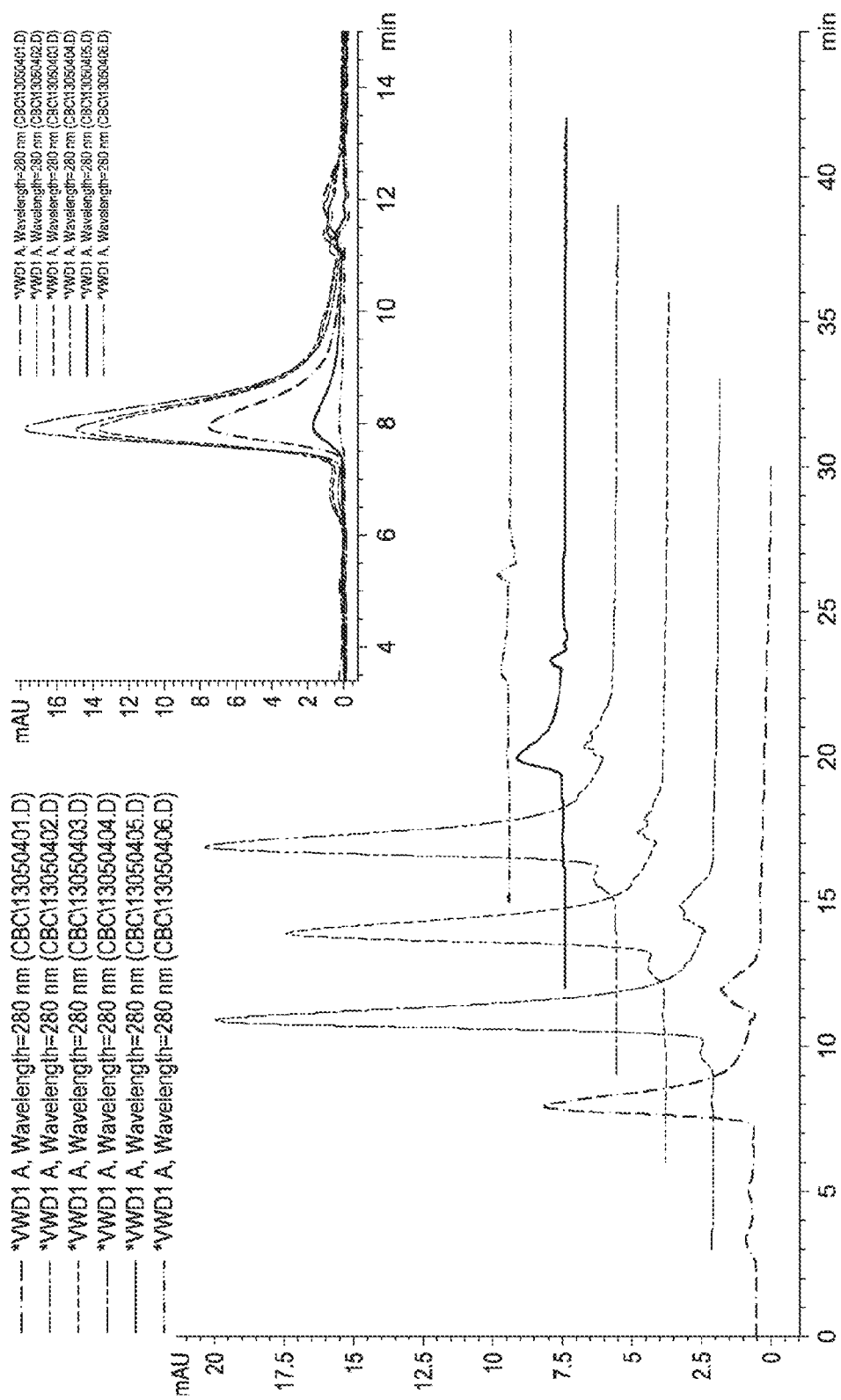
FIG. 5 shows HIC-HPLC chromatograms for each FPLC fraction, and, inset, an overlay of the peaks to demonstrate relative purity of each peak.

FIG. 1 shows the HIC-HPLC chromatogram product of reacting drug and antibody at a drug/antibody ratio of 5.5:1, where DAR represents the number of drugs conjugated per antibody. FIG. 2 shows the HIC-HPLC chromatogram product of reacting drug and antibody at a drug/antibody ratio of 6:1, where DAR represents the number of drugs conjugated per antibody. FIG. 3 shows the HIC-HPLC chromatogram product of reacting drug and antibody at a drug/antibody ratio of 1:6.5, where DAR represents the number of drugs conjugated per antibody. FIG. 4 shows the HIC-HPLC chromatogram product of reacting drug and antibody at a drug/antibody ratio of 1:4, where DAR represents the number of drugs conjugated per antibody. In overlay, FIG. 4 further shows HIC-HPLC chromatograms for individually isolated fractions of DAR 1, DAR 2, DAR 3, DAR 4 and DAR 5 peaks purified using FPLC. FIG. 5 shows HIC-HPLC chromatograms for each FPLC fraction, and, inset, an overlay of the peaks to demonstrate relative purity of each peak.

Figure 6:
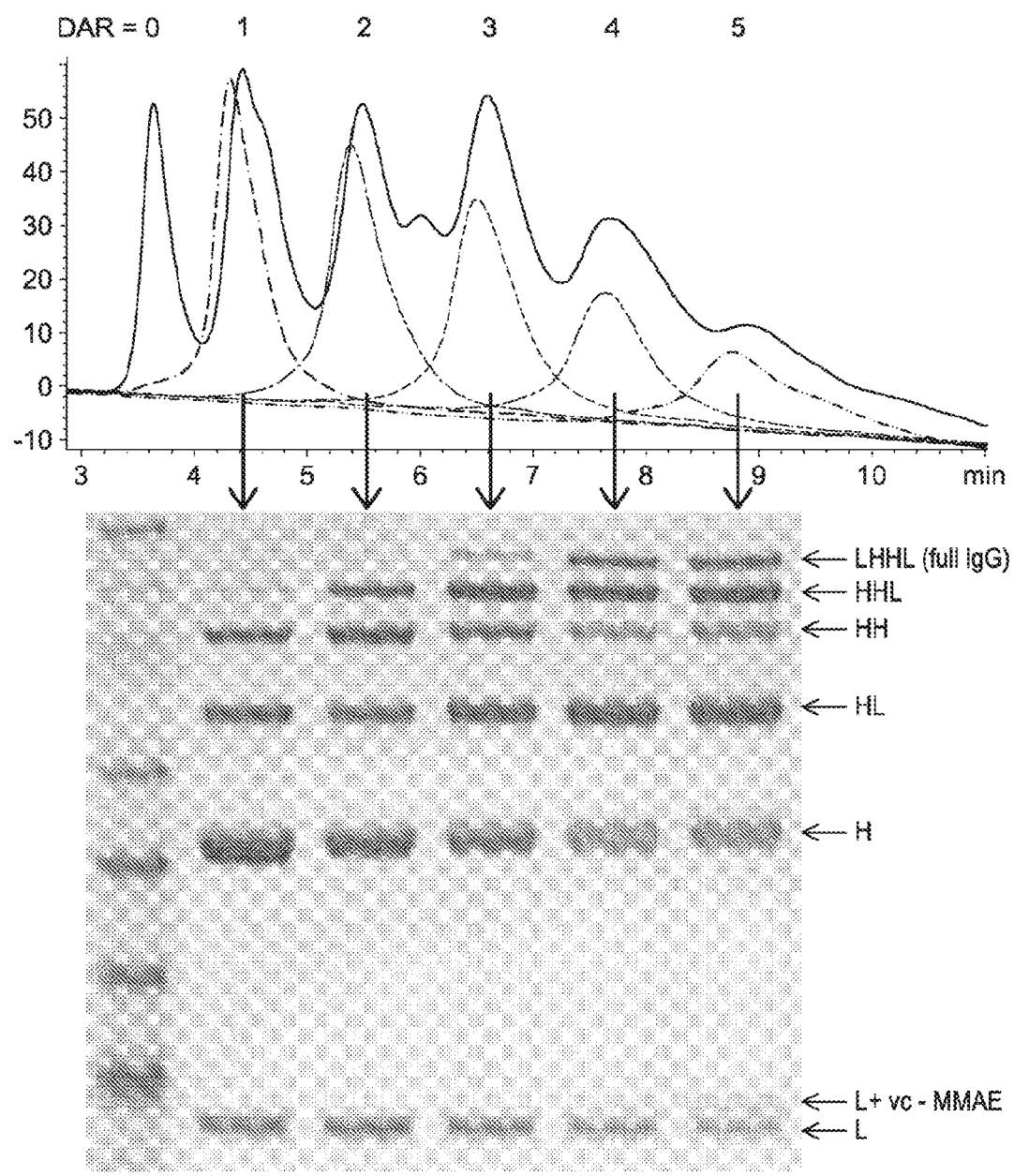
FIG. 6 shows reduced SDS-PAGE analysis for the FPLC fractions depicted in FIGS. 4 and 5.
Figure 7:
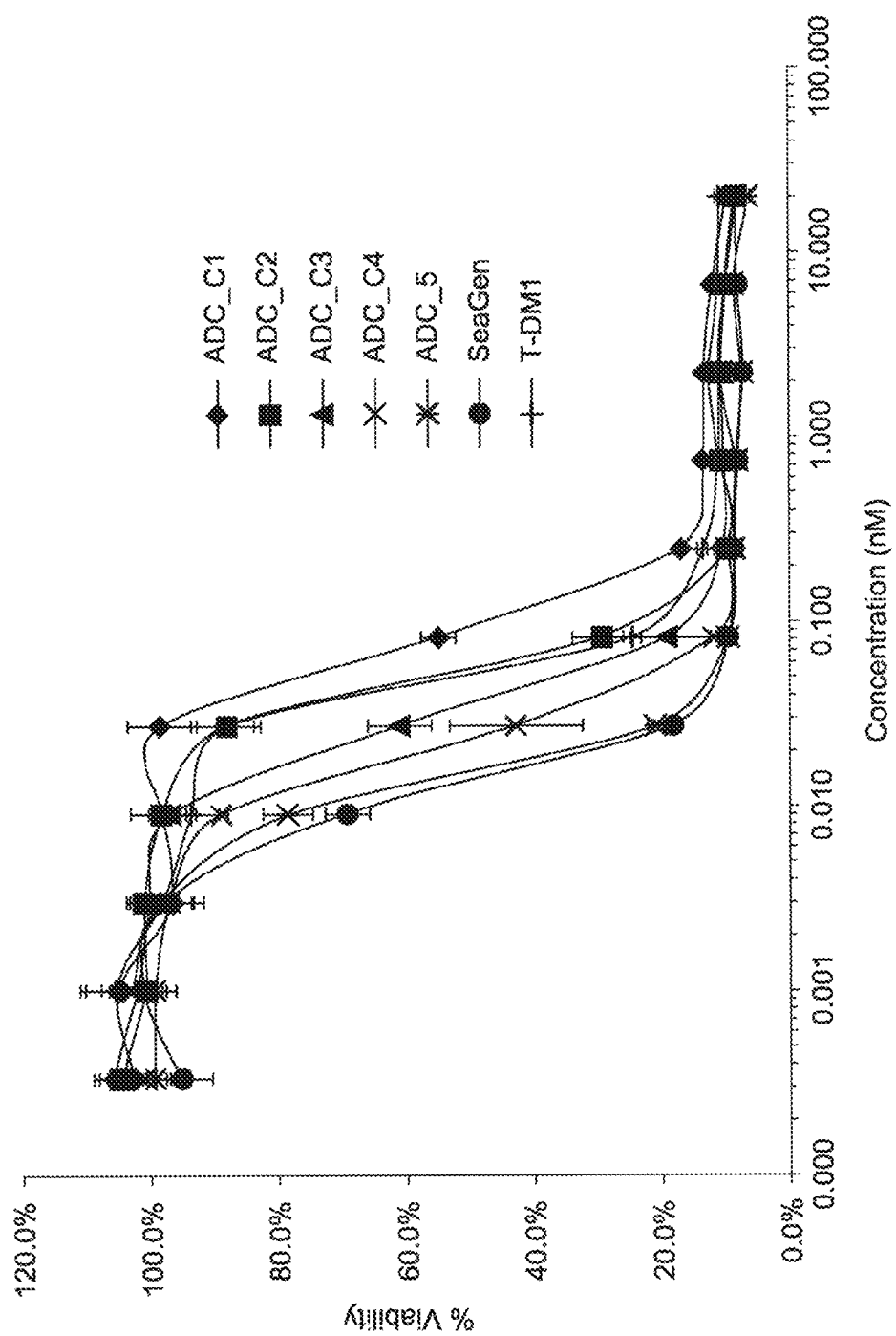
FIG. 7 shows viability of SK-BR-3 cells for seven antibody-drug conjugate samples.

The purified fractions depicted in FIGS. 4 and 5 were further analyzed by reduced SDS-PAGE. The ADC samples were reduced with 20 mM DTT and loaded onto a NuPAGE 4-12% Bis-Tris Gel (Life Technology). The results are shown in FIG. 6, where the abbreviations are as follows:

H-antibody heavy chain
L-antibody light chain
HH-heavy chain dimer
HL-heavy and light chain dimer
HHL-heavy-heavy and light chain trimer
IgG-two heavy-two light chain tetramer In Vitro Cytotoxicity Experiment The antibody drug conjugates were the analyzed for cytotoxicity. The cell lines used were SK-BR-3 human breast adenocarcinoma (HER2 triple positive), HCC1954 human Ductal Carcinoma (HER2 triple positive). These cells were available from ATCC. SK-BR-3 cells were grown in McCoy's 5A medium (Caisson Labs, North Logan, Utah) supplemented with 10% fetal bovine serum. HCC1954 cells were grown in RPMI-1640 medium (Caisson Labs, North Logan, Utah) supplemented with 10% fetal bovine serum. SK-BR-3 cells were plated in 96-well plates at approximately 7,500 cells/well, and HCC1954 cells were plated in 96-well plates at approximately 20,000 cells/well. Antibody-drug conjugates were added in duplicates in the same day. After 72 hour incubation at 37° C., CellTiter-Glo (Promega, Madison, Wis.) were added and cell viability was determined as describe by the manufacture's protocol. The percent viability was determined as following:

% Viability=Average Luminescence Value of the duplicates(treated wells)/Average Luminescence Value of the untreated wells FIG. 7 shows viability of SK-BR-3 cells for seven samples, ADC_C1 (DAR1 from FIGS. 4 and 5), ADC_C2 (DAR2 from FIGS. 4 and 5), ADC_C3 (DAR3 from FIGS. 4 and 5), ADC_C4 (DAR4 from FIGS. 4 and 5), ADC_5 (DAR5 from FIGS. 4 and 5), SeaGen (ADC prepared following published Seattle Genetics method), and T-DM1 (ADC prepared following published Immunogen method).

Figure 8:
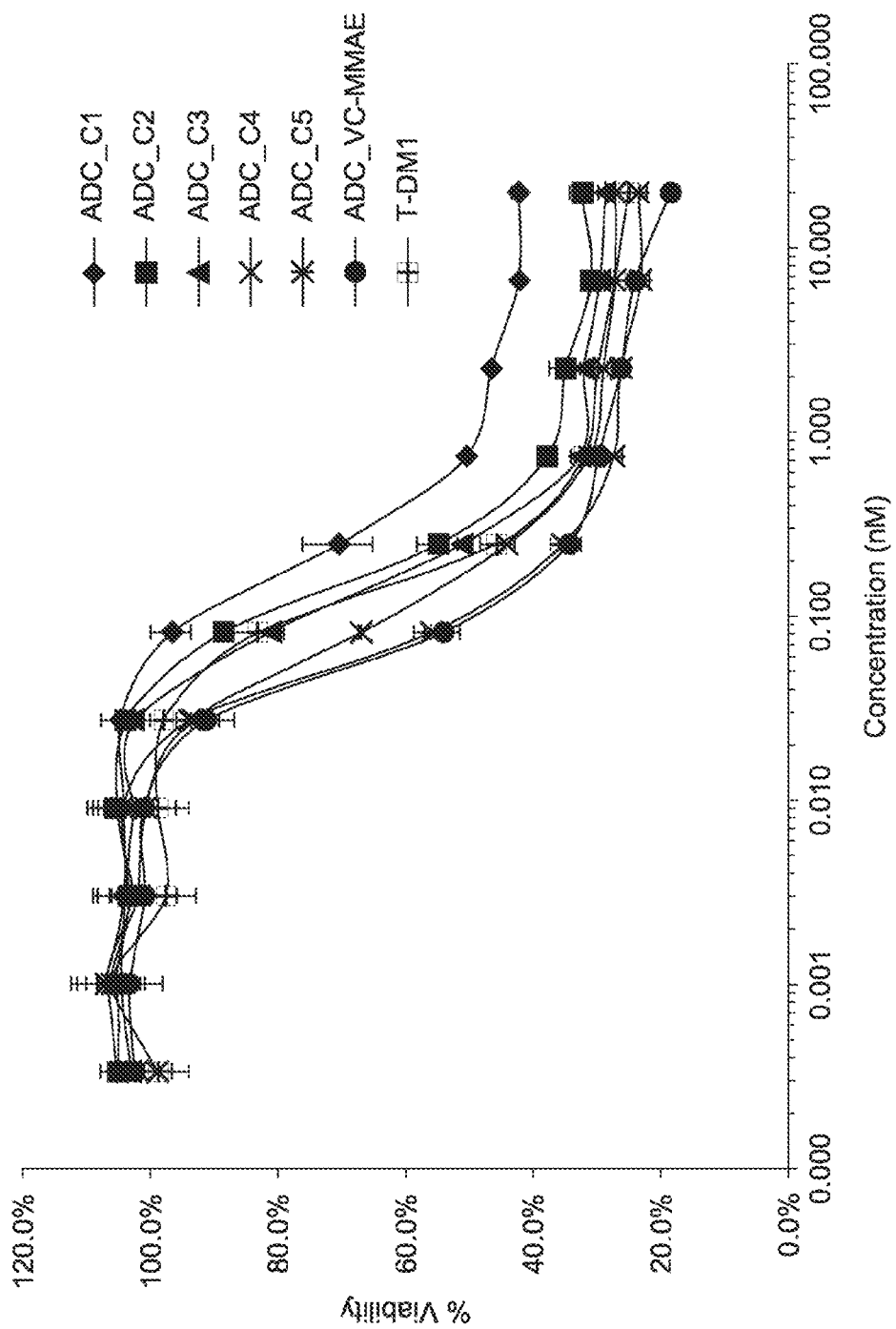
FIG. 8 shows viability of HCC1954 cells for seven antibody-drug conjugate samples.

FIG. 8 shows viability of HCC1954 cells for seven samples, ADC_C1 (DAR1 from FIGS. 4 and 5), ADC_C2 (DAR2 from FIGS. 4 and 5), ADC_C3 (DAR3 from FIGS. 4 and 5), ADC_C4 (DAR4 from FIGS. 4 and 5), ADC_C5 (DAR5 from FIGS. 4 and 5), ADC_VC-M MAE was prepared following published Seattle Genetics method), and T-DM1 (ADC prepared following published Immunogen method).

Figure 10:
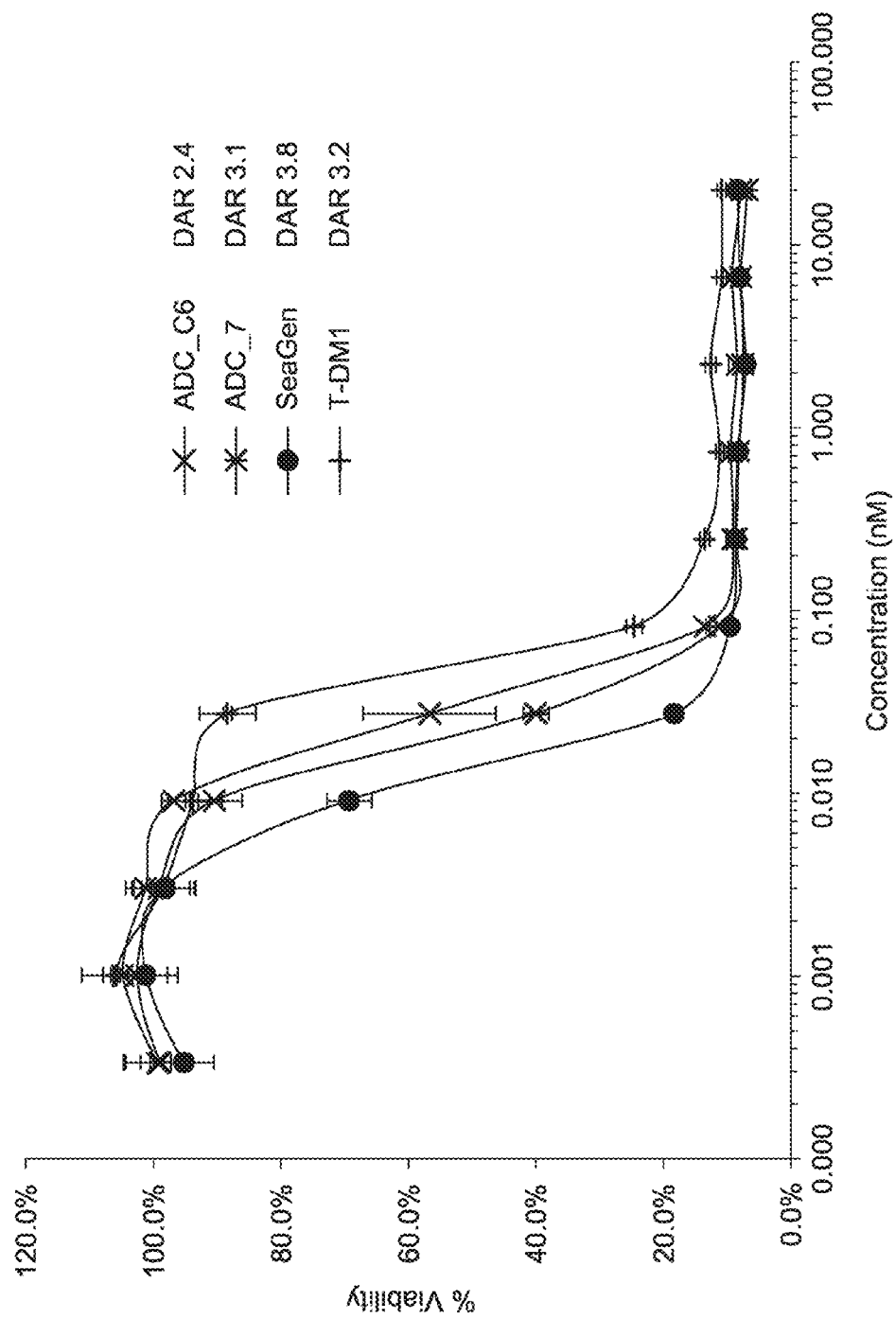
FIG. 10 shows viability of SK-BR-3 cells for four antibody-drug conjugate samples.

FIG. 10 shows viability of SK-BR-3 cells for four samples, both ADC_C6 (DAR2.4) and ADC_C7 (DAR3.1) were prepared using the General Conjugation Procedure and purified by a gel filtration column. SeaGen (ADC prepared following published Seattle Genetics method), and T-DM1 (ADC prepared following published Immunogen method).

Figure 11:
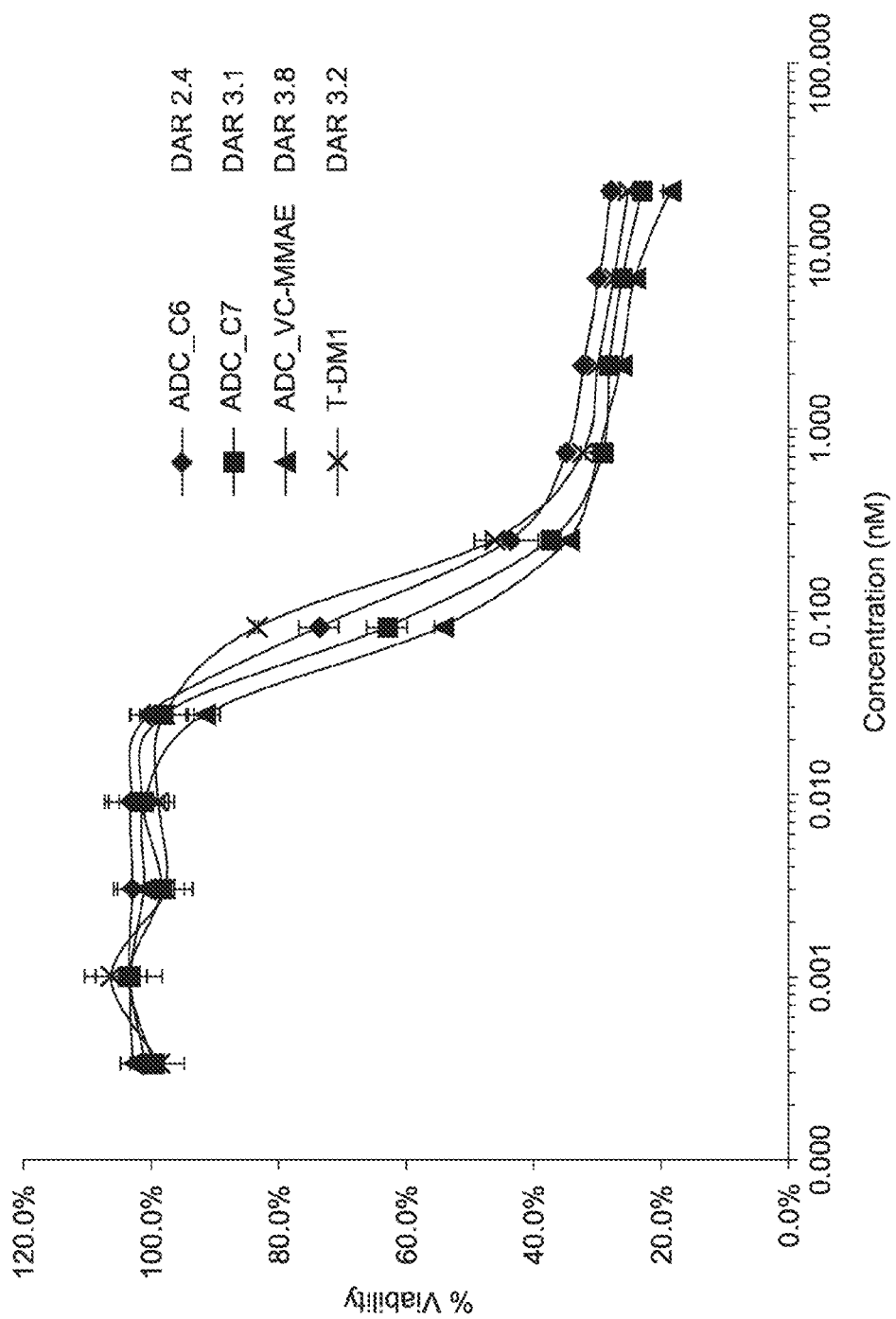
FIG. 11 shows viability of HCC1954 cells for four antibody-drug conjugate samples.

FIG. 11 shows viability of HCC1954 cells for four samples, ADC_C6 (DAR2.4 from FIG. 10), ADC_C7 (DAR3.1 from FIG. 10), ADC_VC-M MAE was prepared following published Seattle Genetics method), and T-DM1 (ADC prepared following published Immunogen method).

Antibody-Drug Conjugation

Trastuzumab and compound 42 were combined in various drug/antibody ratios under conditions where Trastuzumab was incubated with 10 mM TCEP stock solution at 37° C. for 0.5 to 40 hours. After reduction, the excess of TCEP was removed by a gel filtration column. The reduced Trastuzumab was then mixed with compound 42 in drug/antibody ratio range from 1 to 10 at 0 to 40° C. After overnight reaction, excess compound 42 was removed from Trastuzumab-c-34 conjugate by a gel filtration column. Purified Trastuzumab-c-42 conjugates stored at 4 to −20° C. and to be used for in vitro and in vivo tests.

Trastuzumab and compound 40 were combined in various drug/antibody ratios under conditions where Trastuzumab was incubated with 10 mM TCEP stock solution at 37° C. for 0.5 to 40 hours. After reduction, the excess of TCEP was removed by a gel filtration column. The reduced Trastuzumab was then mixed with compound 40 in drug/antibody ratio range from 1 to 10 at 0 to 40° C. After overnight reaction, excess compound 40 was removed from Trastuzumab-c-34 conjugate by a gel filtration column. Purified Trastuzumab-c-40 conjugates stored at 4 to −20° C. and to be used for in vitro and in vivo tests.

Figure 9:
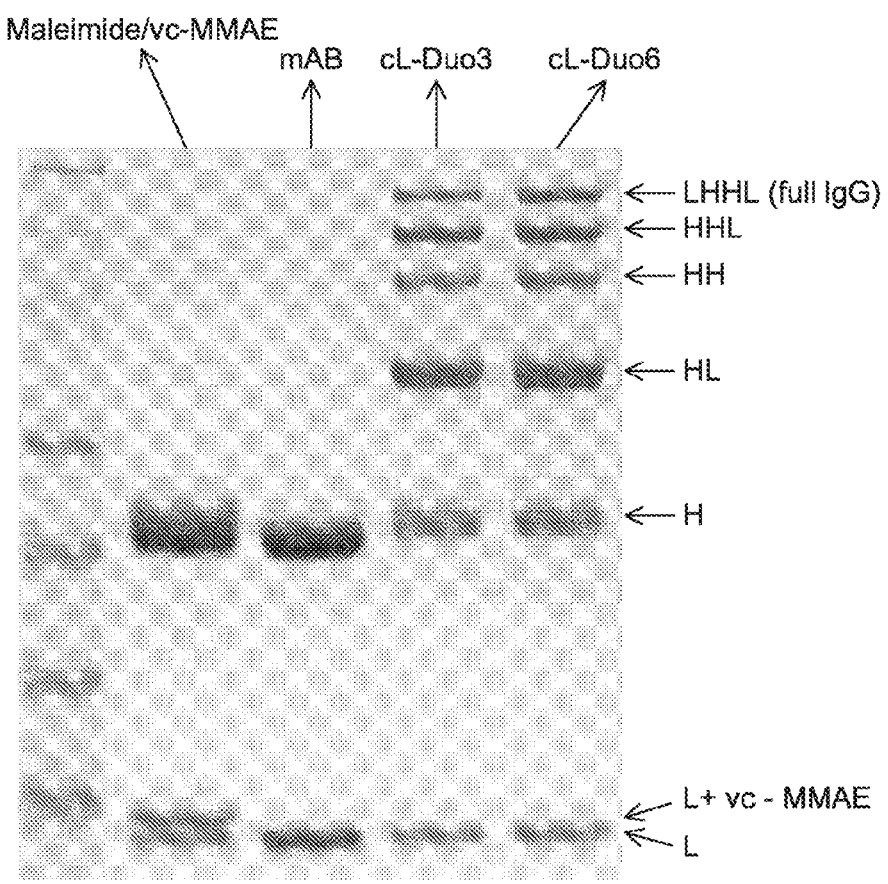
FIG. 9 shows reduced SDS-PAGE analysis for trastuzumab conjugated compound 40.

The product of the conjugation reaction was analyzed using reduced SDS-PAGE. The ADC samples were reduced with 20 mM DTT and loaded onto a NuPAGE 4-12% Bis-Tris Gel (Life Technology). The results are shown in FIG. 9, where the abbreviations are as follows:

H-antibody heavy chain
L+vc-MMAE-antibody light chain-vc-MMAE
L-antibody light chain
HH-heavy chain dimer
HL-heavy and light chain dimer
HHL-heavy-heavy and light chain trimer
IgG-two heavy-two light chain tetramer
cL-Duo3: Trastuzumab—compound 42 conjugate
cL-Duo6: Trastuzumab—compound 40 conjugate In Vitro Cytotoxicity Experiment The Trastuzumab—compound 42 and Trastuzumab—compound 42 conjugates were the analyzed for cytotoxicity. The cytotoxicity methods were performed as described above.

Figure 12:
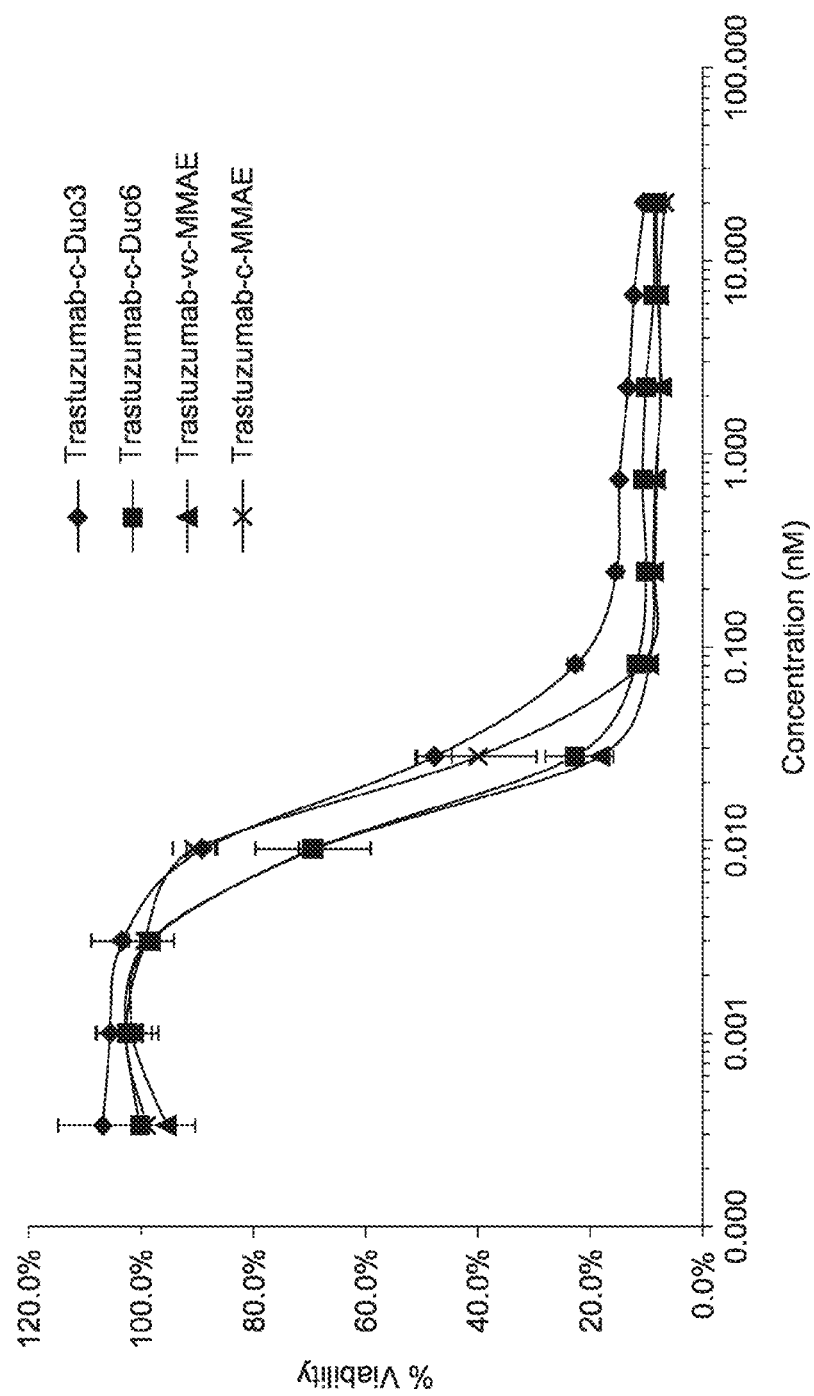
FIG. 12 shows viability of SK-BR-3 cells for four antibody-drug conjugate samples.

FIG. 12 shows viability of SK-BR-3 cells for four samples, Trastuzumab-c-Duo3 (Trastuzumab—compound 42 conjugate), Trastuzumab—c-Duo6 (Trastuzumab—compound 40 conjugate), Trastuzumab-vc-MMAE (prepared following published Seattle Genetics method), and Trastuzumab—c-MMAE (Trastuzumab—compound 34 conjugate, prepared following published Seattle Genetics method).

What is claimed is:

1. An active agent-conjugate composition comprising Formula 1a:

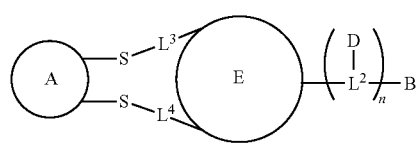

(Ia)

or a pharmaceutically acceptable salt thereof,
wherein:
the A-component is an antibody or an antibody fragment comprising a heavy and light chain;
the E-component is selected from the group consisting of:

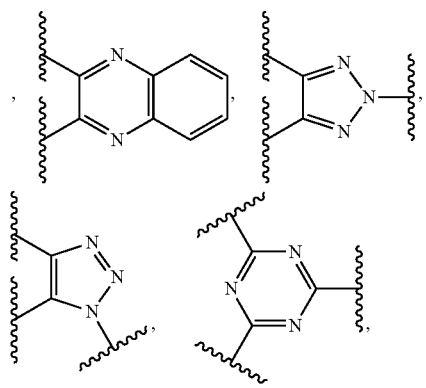

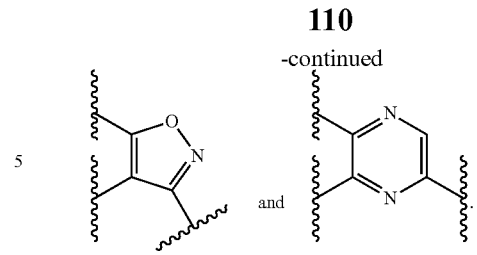

$L^3$ is an optionally substituted $C_1$-$C_6$ alkyl, or $L^3$ is null, when $L^3$ is null the sulfur is directly connected to the E-component;
$L^4$ is an optionally substituted $C_1$-$C_6$ alkyl, or $L^4$ is null, when $L^4$ is null the sulfur is directly connected to the E-component;
B is a monoclonal antibody or peptide;
each D is independently selected, wherein each D includes an active agent;
each $L^2$ is independently a linker, wherein $L^2$ links to E; and
n is 1, 2, 3, 4, 5, 6, 7, 8, 9, or 10.

2. The active agent-conjugate of claim 1, wherein $L^3$ is —(CH$_2$)—; and $L^4$ is —(CH$_2$)—.

3. The active agent-conjugate of claim 1, wherein $L^3$ is null; and $L^4$ is null.

4. The active agent-conjugate of claim 1, wherein:

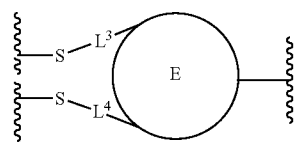

is selected from the group consisting of:

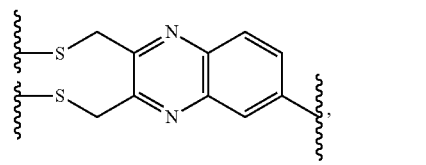

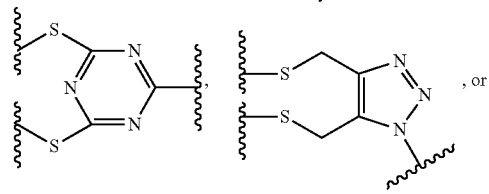

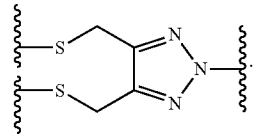

5. The active agent-conjugate of claim 1, wherein said active agent is independently selected from the group consisting of tubulin binders, DNA alkylators, DNA intercalators, enzyme inhibitors, and immune modulators.

6. The active agent-conjugate of claim 1, wherein the structure of Formula Ia has a structure selected from the group consisting of:

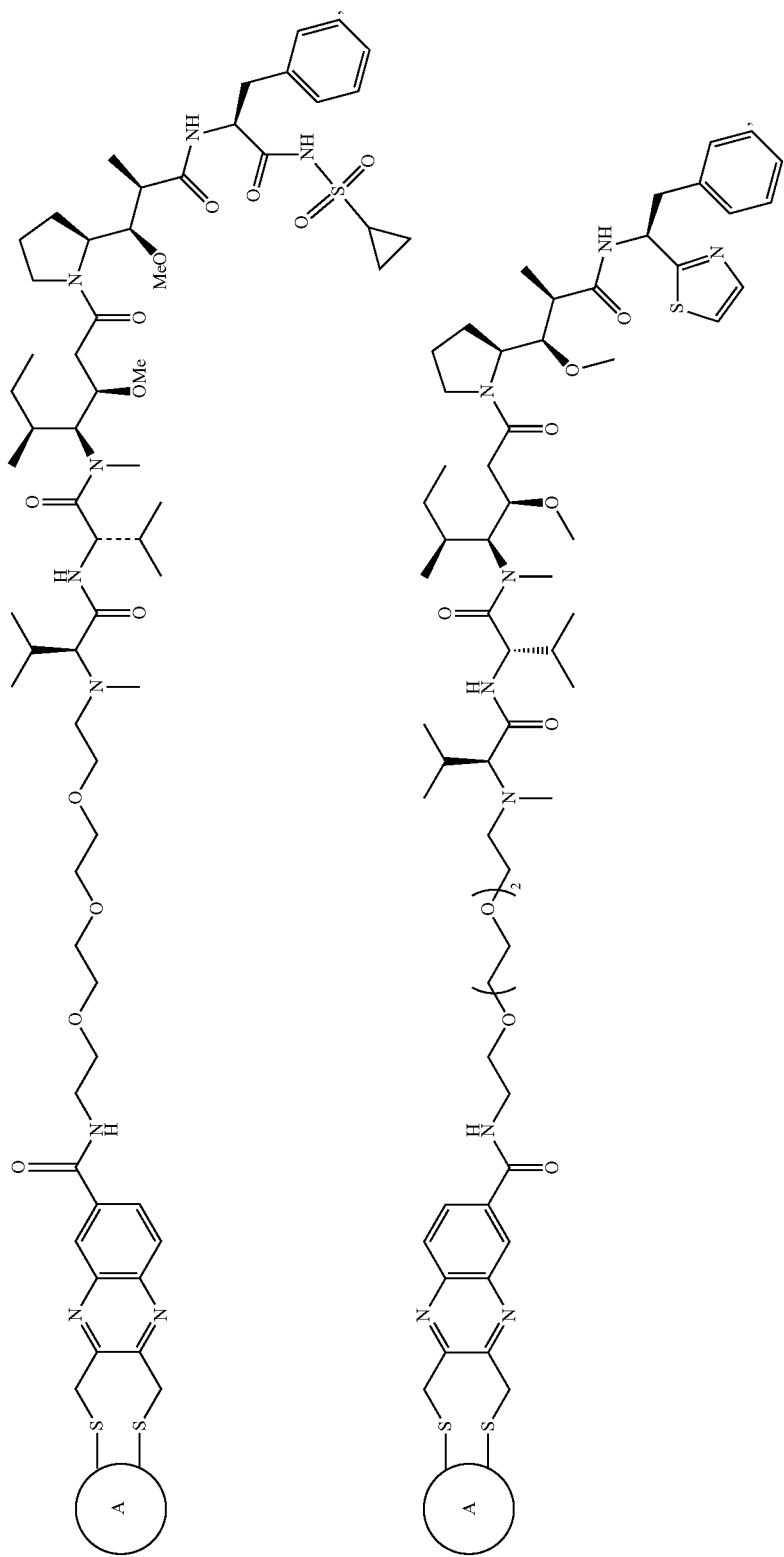

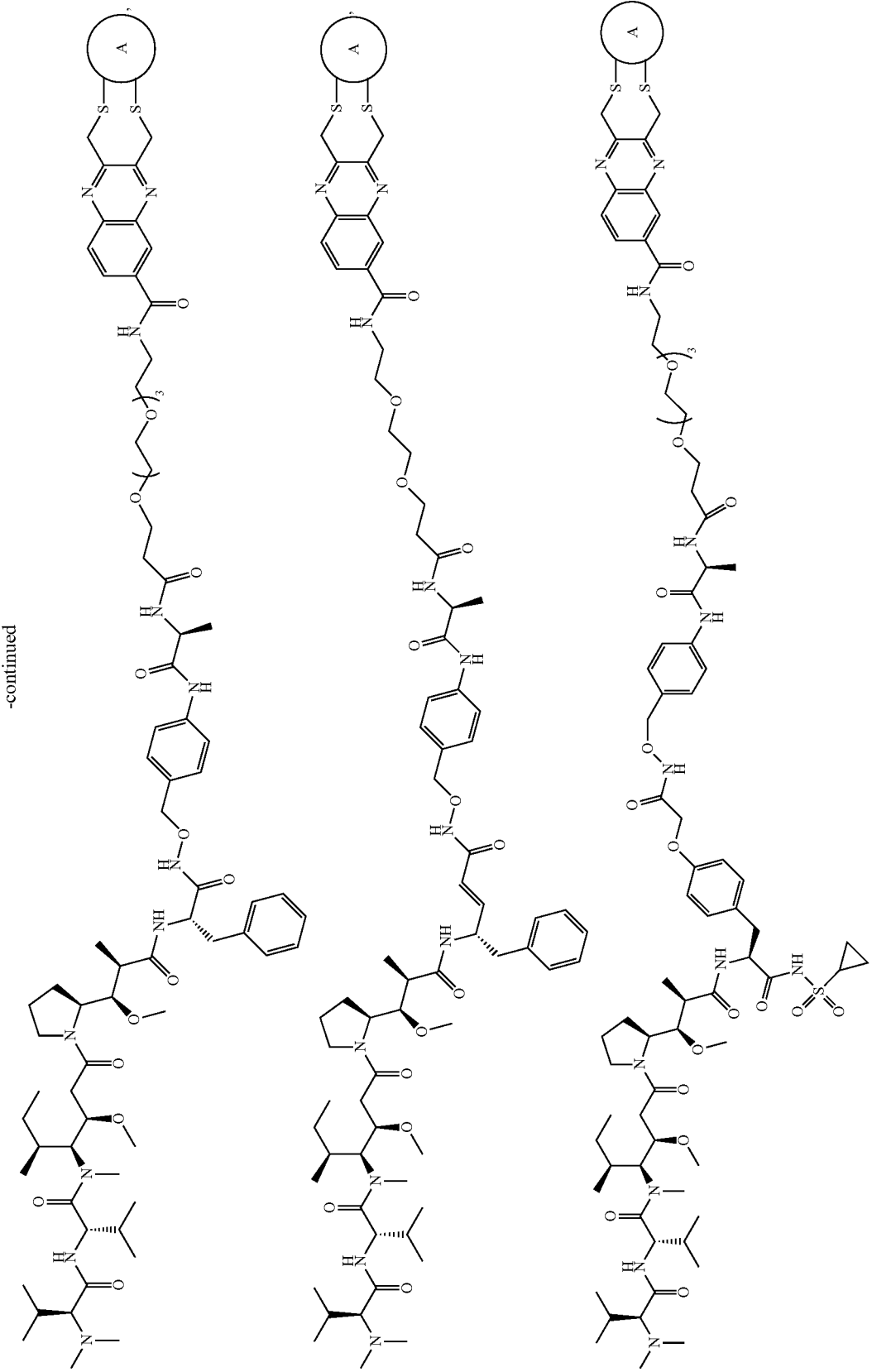

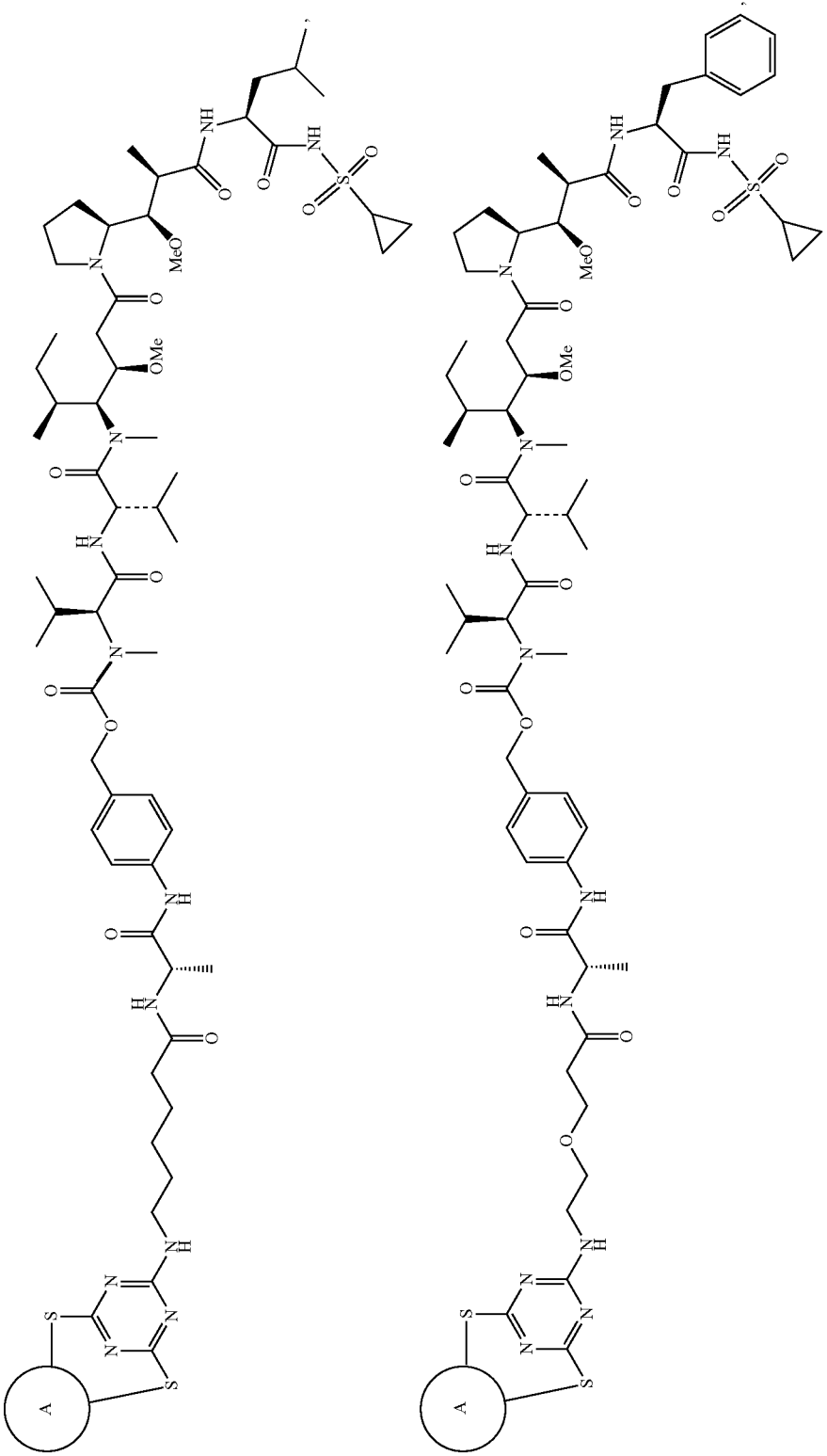

-continued
117
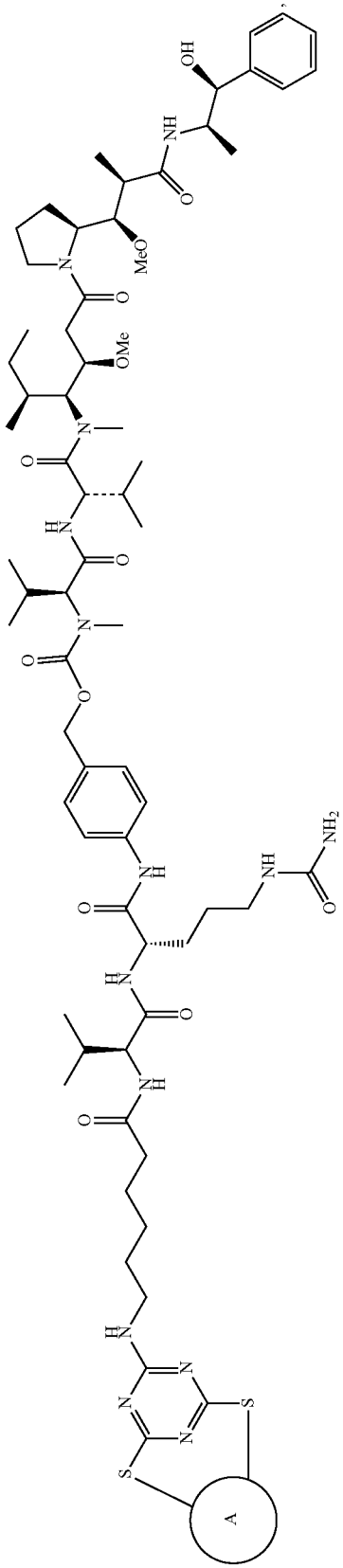
118
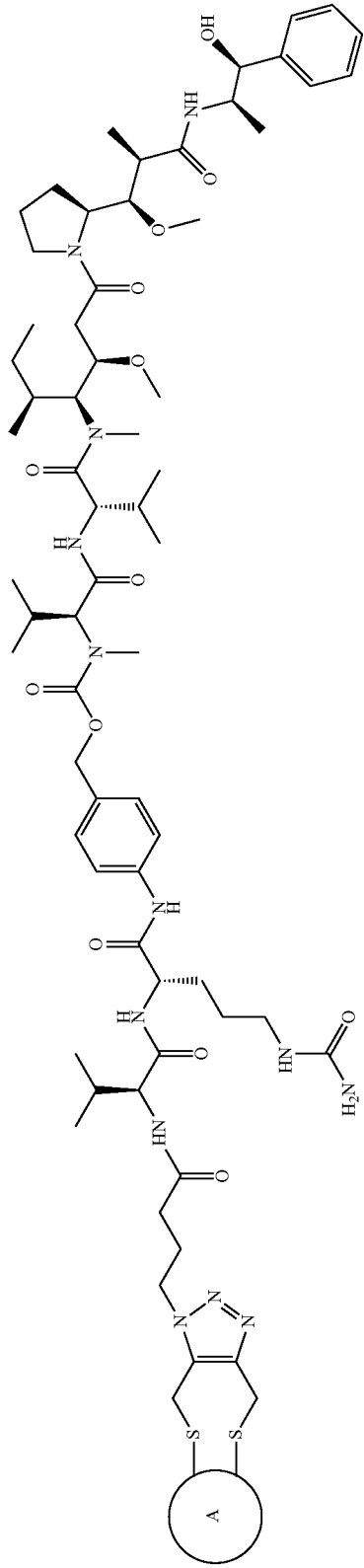
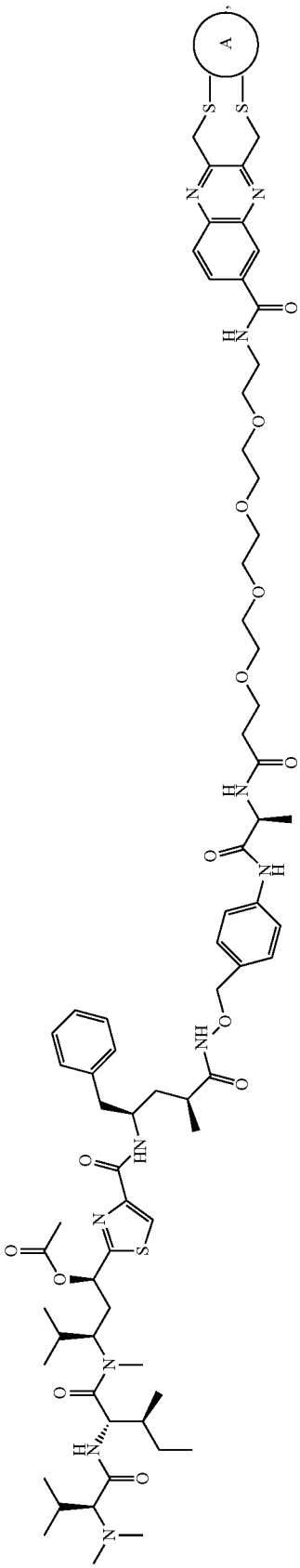

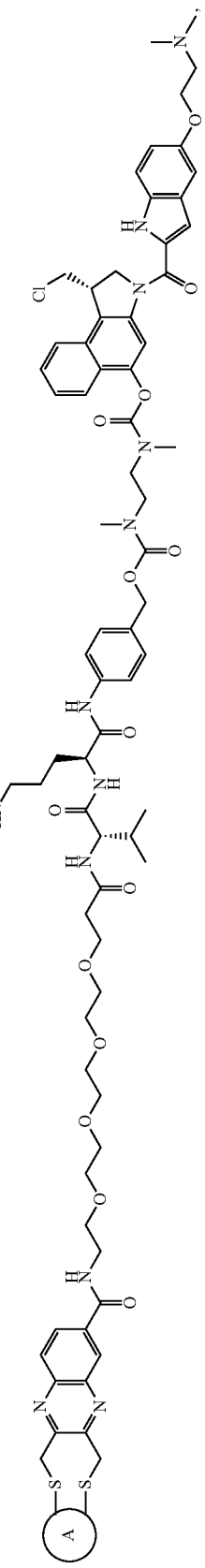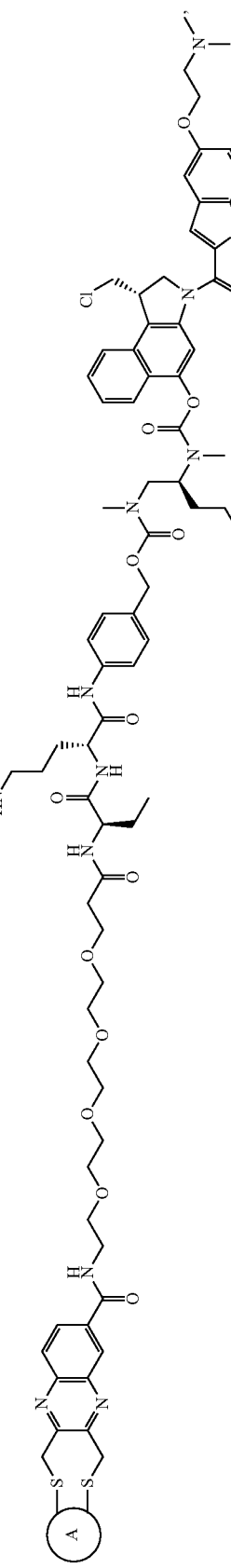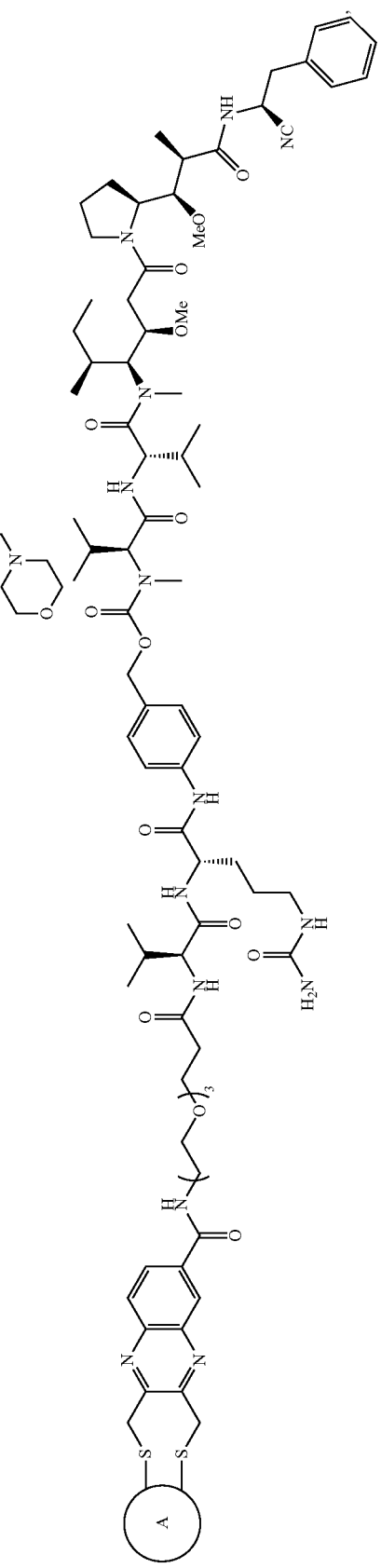

121
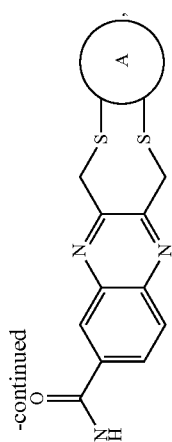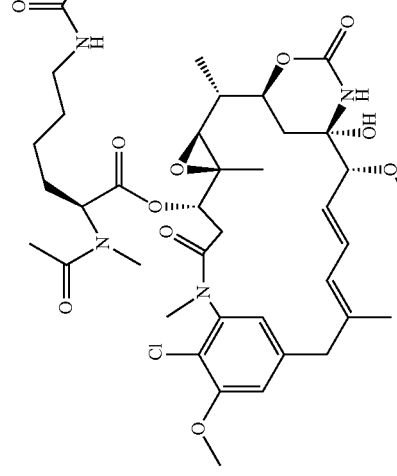
122
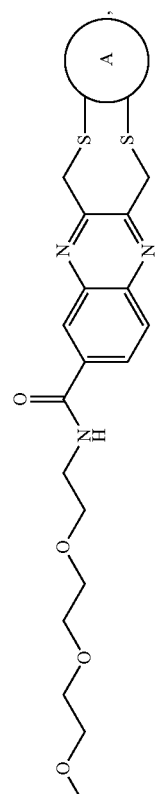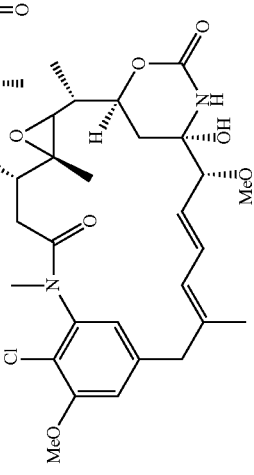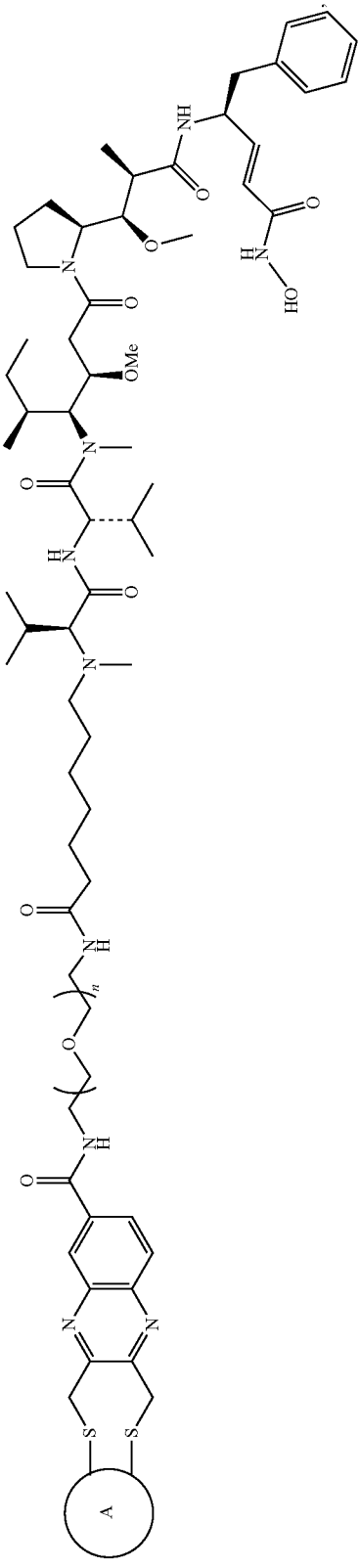

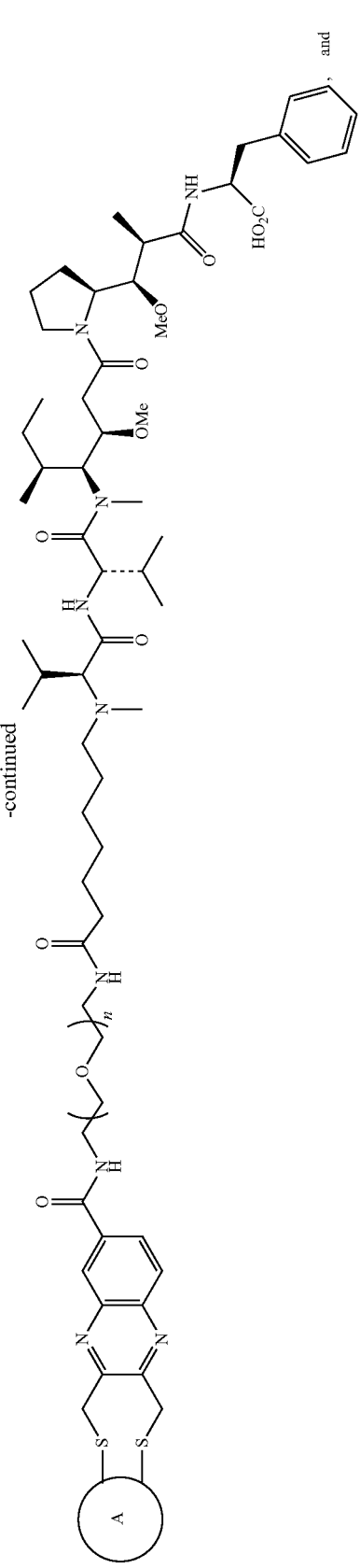
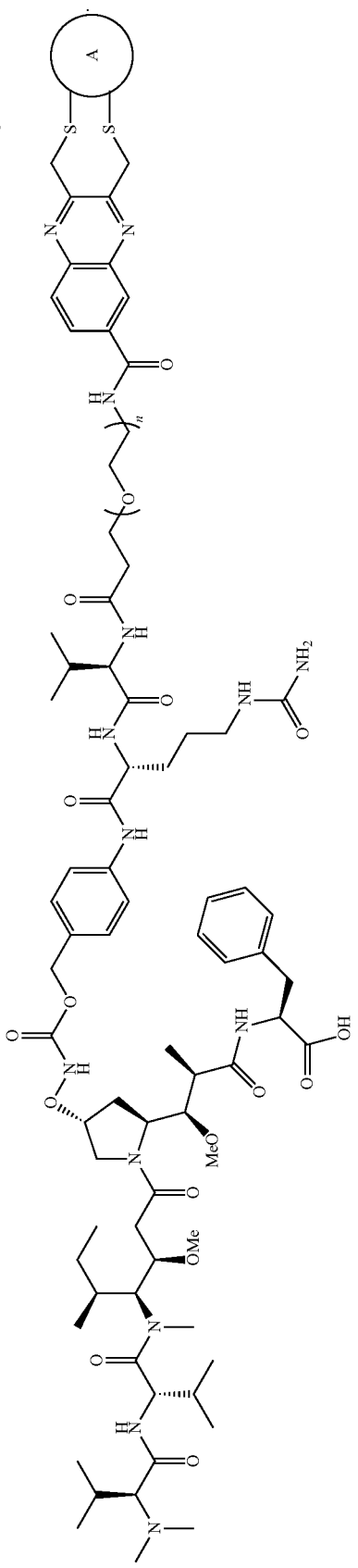

7. The active agent-conjugate of claim 1, wherein $L^2$ is a peptide or an oligosaccharide.

8. The active agent-conjugate of claim 1, wherein the A component comprises at least one modified L-Alanine residue.

9. The active agent-conjugate of claim 1, wherein said active agent is independently selected from peptides and nucleotides.

10. The active agent-conjugate of claim 1, wherein $L^2$ is selected from the group consisting of —$(CH_2)_n$—, —$(CH_2CH_2O)_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, and PAB.

* * * * *